United States Patent
Rennie et al.

(10) Patent No.: US 11,897,887 B2
(45) Date of Patent: Feb. 13, 2024

(54) SGC STIMULATORS

(71) Applicant: Tisento Therapeutics Inc., Cambridge, MA (US)

(72) Inventors: Glen Robert Rennie, Somerville, MA (US); Paul Allan Renhowe, Sudbury, MA (US); Takashi Nakai, Newton, MA (US); Ara Mermerian, Waltham, MA (US); Helen Cumberbatch, Cambridge, MA (US)

(73) Assignee: Tisento Therapeutics Inc., Cambridge, MA (US)

( * ) Notice: Subject to any disclaimer, the term of this patent is extended or adjusted under 35 U.S.C. 154(b) by 823 days.

(21) Appl. No.: 16/955,494

(22) PCT Filed: Dec. 19, 2018

(86) PCT No.: PCT/US2018/066547
§ 371 (c)(1),
(2) Date: Dec. 16, 2020

(87) PCT Pub. No.: WO2019/126354
PCT Pub. Date: Jun. 27, 2019

(65) Prior Publication Data
US 2020/0377508 A1 Dec. 3, 2020

Related U.S. Application Data

(60) Provisional application No. 62/607,619, filed on Dec. 19, 2017.

(51) Int. Cl.
*C07D 487/04* (2006.01)
*C07F 9/09* (2006.01)
*A61K 45/06* (2006.01)

(52) U.S. Cl.
CPC .............. *C07D 487/04* (2013.01); *C07F 9/09* (2013.01); *A61K 45/06* (2013.01)

(58) Field of Classification Search
CPC .................................. C07D 487/04; C07F 9/09
See application file for complete search history.

(56) References Cited

FOREIGN PATENT DOCUMENTS

| | | |
|---|---|---|
| DE | 102011007890 A1 | 10/2012 |
| DE | 102012200356 A1 | 7/2013 |
| JP | 2017-160225 A | 9/2017 |
| WO | 2015/106268 A1 | 7/2015 |
| WO | 2016/081668 A1 | 5/2016 |
| WO | 2017/197555 A1 | 11/2017 |
| WO | 2017/200825 A1 | 11/2017 |

OTHER PUBLICATIONS

International Search Report and Written Opinion for Application No. PCT/US2018/066547, dated Mar. 21, 2019, 10 pages.

*Primary Examiner* — Laura L Stockton
(74) *Attorney, Agent, or Firm* — McCarter & English, LLP; Xin Zhang; James M. Alburger

(57) ABSTRACT

The present disclosure relates to stimulators of soluble guanylate cyclase (sGC), pharmaceutically acceptable salts, pharmaceutical formulations comprising them as well as their phosphate ester prodrugs, and their uses alone or in combination with one or more additional agents, for treating various diseases, wherein an increase in the concentration of nitric oxide (NO) and/or an increase in the concentration of cyclic Guanosine Monophosphate (cGMP), or both, or the upregulation of the NO pathway is desirable. The compounds are of Formula I.

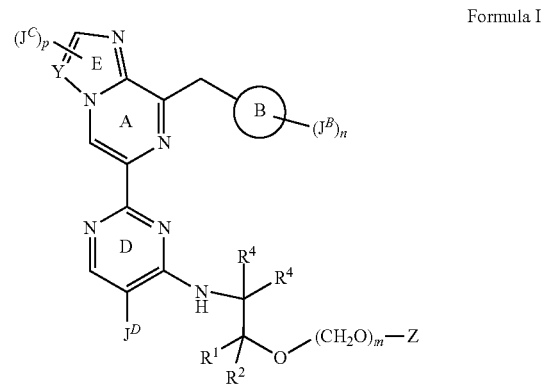

Formula I

24 Claims, No Drawings

SGC STIMULATORS

RELATED APPLICATIONS

This application is a 35 U.S.C. § 371 national stage filing of International Application No. PCT/US2018/066547, filed on Dec. 19, 2018, which in turn claims the benefit of the filing date, under 35 U.S.C. § 119(e), of U.S. Provisional Application No. 62/607,619, filed on Dec. 19, 2017. The entire contents of each of the foregoing applications are incorporated herein by reference.

FIELD OF THE INVENTION

The present disclosure relates to stimulators of soluble guanylate cyclase (sGC) and pharmaceutically acceptable salts thereof. It also relates to pharmaceutical formulations comprising them and their uses thereof, alone or in combination with one or more additional agents, for treating various diseases. The disease are ones that would benefit from sGC stimulation or from an increase in the concentration of nitric oxide (NO) and/or cyclic guanosine monophosphate (cGMP).

BACKGROUND OF THE INVENTION sGC is the primary receptor for NO in vivo. Upon binding to sGC, NO activates its catalytic domain and results in the conversion of guanosine-5'-triphosphate (GTP) into the secondary messenger cGMP. The increased level of cGMP, in turn, modulates the activity of downstream effectors including protein kinases, phosphodiesterases (PDEs) and ion channels. In the body, NO is synthesized from arginine and oxygen by various nitric oxide synthase (NOS) enzymes and by sequential reduction of inorganic nitrate. Experimental and clinical evidence indicates that reduced NO concentrations, reduced NO bioavailability and/or reduced responsiveness to endogenously produced NO contributes to the development of numerous diseases. sGC stimulators are heme-dependent agonists of the sGC enzyme that work synergistically with varying amounts of NO to increase its enzymatic conversion of GTP to cGMP. sGC stimulators are clearly differentiated from and structurally unrelated to another class of NO-independent, heme-independent agonists of sGC known as sGC activators.

Therapies that improve or restore the function of sGC offer considerable advantages over current alternative therapies that either target the pathway or otherwise benefit from the upregulation of the NO-sGC pathway. There is a need to develop novel sGC stimulators.

SUMMARY OF THE INVENTION

The present invention is directed to compounds of Formula I, and pharmaceutically acceptable salts thereof,

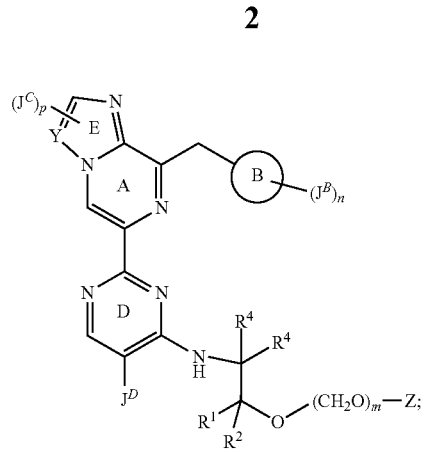

Formula I wherein:
Y is independently N or C;
ring B is a phenyl or a 5 or 6-membered heteroaryl ring, containing 1 or 2 ring heteroatoms independently selected from N, O or S;
n is an integer selected from 0 to 3; and each $J^B$ is independently halogen, —CN, a $C_{1-6}$ aliphatic, —$OR^B$ or a $C_{3-8}$ cycloaliphatic ring;
wherein each $J^B$ that is a $C_{1-6}$ aliphatic and each $J^B$ that is a $C_3$_cycloaliphatic ring is optionally and independently substituted with up to 3 instances of $R^3$;
each $R^B$ is independently hydrogen, a $C_{1-6}$ aliphatic or a $C_{3-8}$ cycloaliphatic ring; said $R^B$ optionally and independently substituted with up to 3 instances of $R^{3a}$;
each $R^3$ and $R^{3a}$ is, in each instance, independently halogen, —CN, $C_{1-4}$ alkyl, $C_{1-4}$ haloalkyl, —$O(C_{1-4}$ alkyl) or —$O(C_{1-4}$ haloalkyl); Z is selected from the group consisting of hydrogen, —P(O)(OH)$_2$, —P(O)(OH)O$^-$ M+, —P(O)(O$^-$)$_2$(M+)$_2$, —P(O)(0-)$_2$D$^{2+}$ and —P(O)(O-Benzyl)$_2$; wherein M+ is a pharmaceutically acceptable monovalent cation and $D^{2+}$ is a pharmaceutically acceptable divalent cation;
m is 0 or 1; R is $C_{1-4}$ alkyl, $C_{1-4}$ fluoroalkyl, —C(O)NH$_2$ or hydrogen; and $R^2$ is $C_{1-4}$ alkyl, $C_{1-4}$ fluoroalkyl or hydrogen;
both instances of $R^4$ are simultaneously hydrogen or both instances of $R^4$, together with the carbon atom to which they are attached form a carbonyl group;
$J^D$ is hydrogen, halogen, methoxy or —CN
p is 1, 2 or 3; and
each $J^C$ is independently hydrogen, halogen, $C_{1-4}$ aliphatic, $C_{1-4}$ alkoxy or —CN; wherein each said $C_{1-4}$ aliphatic and each said $C_{1-4}$ alkoxy is optionally and independently substituted by up to 3 instances of $C_{1-4}$ alkoxy, $C_{1-4}$haloalkoxy, —OH or halogen.

In another embodiment, the invention relates to pharmaceutical compositions comprising a compound of Formula I, or a pharmaceutically acceptable salt thereof and at least one pharmaceutically acceptable excipient or carrier. In another embodiment, the invention relates to pharmaceutical dosage forms comprising said pharmaceutical compositions.

In another embodiment, the invention relates to a method of treating a disease in a subject in need thereof, comprising administering, alone or in combination therapy, a therapeutically effective amount of a compound of Formula I, or a pharmaceutically acceptable salt thereof, or pharmaceutical composition thereof, to the subject; wherein the disease is one that would benefit from sGC stimulation or from an increase in the concentration of NO and/or cGMP. The invention also provides a compound of Formula I, or a pharmaceutically acceptable salt thereof, for use in a method of treating a disease in a subject in need thereof, alone or in combination therapy, wherein the disease is one that would benefit from sGC stimulation or from an increase in the concentration of NO and/or cGMP. Also provided is a use of a compound of Formula I, or a pharmaceutically acceptable salt thereof, for the manufacture of a medicament for treating a disease in a subject in need thereof, alone or in combination therapy, wherein the disease is one that would benefit from sGC stimulation or from an increase in the concentration of NO and/or cGMP.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

In general, the term "substituted" refers to the replacement of one or more hydrogen radicals of a given structure with another specified radical substituent, different from hydrogen (some non-limiting examples would be a hydroxy, a phenyl, or an alkyl radical). If a structure or moiety is "optionally substituted" it may be substituted or unsubstituted. When one or more position(s) of a given chemical structure can be substituted or optionally substituted with one or more than one substituent selected from a specified group or list, the substituent or substituents at each position may be "independently selected" to be equal or the same at each position and for each instance, unless otherwise specified. For example, if a phenyl is substituted with two instances of $R^{100}$, and each $R^{100}$ is independently selected from halogen and methyl, that means that each instance of $R^{100}$ is separately selected from halogen or methyl; for instance, one $R^{100}$ may be fluoro and one may be methyl, or both may be chloro, etc.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. A chemically feasible compound is a compound that can be prepared by a person skilled in the art based on the disclosures herein, supplemented, if necessary, by relevant knowledge of the art.

The phrase "up to", as used herein, refers to zero or any integer number that is equal or less than the number following the phrase. For example, "up to 3" means any one of 0, 1, 2, or 3. As described herein, a specified number range of atoms or of substituents includes any integer therein. For example, a group having from 1-4 atoms could have 1, 2, 3 or 4 atoms. When any variable occurs more than one time at any position, its definition on each occurrence is independent from every other occurrence. When a group is substituted with 0 instances of a certain variable, this means the group is unsubstituted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans isomers. Therefore, single stereochemical isomers as well as racemates, and mixtures of enantiomers, diastereomers, and cis-trans isomers of the present compounds are within the scope of the present disclosure. Unless otherwise stated, all tautomeric forms of the compounds of the present disclosure are also within the scope of the invention.

In one embodiment, the present disclosure may include replacement of hydrogen with deuterium (i.e., $^2$H), which may afford certain therapeutic advantages resulting from greater metabolic stability (e.g., increased in vivo half-life or reduced dosage requirements) and hence may be preferred in some circumstances. Deuterium labeled compounds of the present invention can generally be prepared by following procedures analogous to those disclosed in the Schemes and/or in the Examples herein below, by substituting a deuterated reagent for a non-deuterated reagent.

The term "aliphatic", as in, for example, "aliphatic group" or "aliphatic chain", means an unbranched or branched hydrocarbon (formed by only carbon and hydrogen) chain that is completely saturated or that contains one or more units of unsaturation. Suitable aliphatic groups include, but are not limited to, linear or branched, alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. An aliphatic group will be represented by the term "$C_{x-y}$ aliphatic"; wherein x and y are the minimum and the maximum number of carbon atoms forming the aliphatic chain.

The term "alkyl" as in, for example, "alkyl chain" or "alkyl group", as used herein, refers to a saturated unbranched or branched monovalent hydrocarbon radical. A $C_x$ alkyl is an alkyl chain containing x carbon atoms, wherein x is an integer different from 0. A "$C_{x-y}$ alkyl", wherein x and y are two different integers, both different from 0, is an alkyl chain containing between x and y number of carbon atoms, inclusive. For example, a $C_{1-6}$ alkyl is an alkyl as defined above containing any number of between 1 and 6 carbon atoms. Examples of alkyl groups include, but are not limited to, methyl (i.e., $C_1$ alkyl), ethyl (i.e., $C_2$ alkyl), n-propyl (a $C_3$ alkyl), isopropyl (a different $C_3$ alkyl), n-butyl, isobutyl, s-butyl, t-butyl, pentyl, hexyl, heptyl, octyl and the like.

The term "alkenyl" (as in "alkenyl chain" or "alkenyl group"), refers to an unbranched or branched monovalent hydrocarbon radical with at least one site of unsaturation that is a carbon-carbon, $sp^2$ double bond, wherein the alkenyl radical includes radicals having "cis" and "trans" orientations, or using an alternative nomenclature, "E" and "Z" orientations. Examples of alkenyls include, but are not limited to, vinyl, allyl and the like. A $C_x$ alkenyl is an alkenyl chain containing x carbon atoms, wherein x is an integer different from 0. Alternatively, an alkenyl group will be represented by the term "$C_{x-y}$ alkenyl"; wherein x and y are the minimum and the maximum number of carbon atoms forming the alkenyl chain.

The term "alkynyl" (as in "alkynyl chain" or "alkynyl group"), refers to an unbranched or branched monovalent hydrocarbon radical with at least one site of unsaturation that is a carbon-carbon sp triple bond. Examples include, but are not limited to, ethynyl, propynyl, and the like. A $C_x$ alkynyl is an alkynyl chain containing x carbon atoms, wherein x is an integer different from 0. Alternatively, an alkynyl group will be represented by the term "$C_{x-Y}$ alkynyl"; wherein x and y are the minimum and the maximum number of carbon atoms forming the alkynyl chain.

The term "cycloaliphatic", as in "cycloaliphatic ring" or "cycloaliphatic group" refers to a ring system formed only by carbon and hydrogen atoms that is completely saturated or that contains one or more units of unsaturation but which is not aromatic. A $C_x$ cycloaliphatic is a cycloaliphatic ring containing x carbon atoms, wherein x is an integer different from 0. Alternatively, a cycloaliphatic ring will be represented by the term "$C_{x-y}$ cycloaliphatic"; wherein x and y are the minimum and the maximum number of carbon atoms forming the cycloaliphatic ring. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like. The term "cycloaliphatic" also includes polycyclic ring systems (e.g., bicyclic, tricyclic or tetracyclic)). The polycyclic ring system may be a bridged, a fused, or a spiro system.

"Bridged" ring systems comprise two rings which share two non-adjoining ring atoms.

"Fused" ring systems comprise two rings which share two adjoining ring atoms.

"Spiro" ring systems comprise two rings which share one adjoining ring atom.

The term "cycloalkyl", as in "cycloalkyl ring" or "cycloalkyl group", as used herein, refers to a ring system formed only by carbon and hydrogen atoms which is completely saturated. Suitable cycloalkyl groups include, but are not limited to, cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like. A cycloalkyl ring will be represented by the term "$C_{x-y}$ cycloalkyl"; wherein x and y are the minimum and the maximum number of carbon atoms forming the cycloalkyl ring. The term "cycloalkyl" also includes polycyclic ring systems (e.g., bicyclic, tricyclic or tetracyclic). The polycyclic ring system may be a bridged, a fused, or a spiro system.

As used herein, the term "aryl" (as in "aryl ring" or "aryl group"), refers to a ring system formed only by carbon and hydrogen atoms that is aromatic. The term also includes polycyclic ring systems (e.g., bicyclic, tricyclic, tetracyclic, etc.). Examples of aryl rings include, but are not limited to, phenyl, naphthyl, indenyl, fluorenyl, and anthracenyl.

The term "heteroatom" refers to one or more of oxygen, sulfur, nitrogen, phosphorus, or silicon, including any oxidized form of nitrogen, sulfur, phosphorus, or silicon, and including the quaternized form of any basic nitrogen.

The term "ring atom" refers to an atom such as C, N, O or S that is part of a ring (rings include, for example, a cycloaliphatic ring (e.g. a cycloalkyl ring), a heterocyclic ring, an aryl ring (e.g., a phenyl ring) or a heteroaryl ring.

The term "ring heteroatom" refers to an atom such as N, O or S that is part of a heterocyclic ring or a heteroaryl ring.

A "substitutable ring atom" is a ring carbon or nitrogen atom bonded to at least one hydrogen atom. The hydrogen can be optionally replaced with a suitable substituent group. "Substitutable ring atom" does not include ring carbon or nitrogen atoms wherein the structure depicts that they are already attached to one or more moieties or substituents other than hydrogen and no hydrogens are available for substitution. When a certain ring is optionally substituted, it will be understood that it may be substituted at one or some or all of its substitutable ring atoms, depending on the number of substituents allowed.

The term "heterocycle" (or "heterocyclyl"), as in "heterocyclic group" or "heterocyclic ring"), as used herein, refers to a ring system in which one or more ring atoms are an independently selected heteroatom, wherein said ring is completely saturated or contains one or more units of unsaturation but which is not aromatic. Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, and 5-imidazolidinyl. Examples of bicyclic heterocyclic ring systems include, but are not limited to: 2-oxa-bicyclo[2.2.2]octyl, 1-aza-bicyclo[2.2.2]octyl. As used herein, the term "heterocycle" also includes polycyclic ring systems (e.g., bicyclic, tricyclic or tetracyclic).

The term "heteroaryl" (or "heteroaromatic"), as in "heteroaryl group" or "heteroaryl ring") refers to a ring which is aromatic and contains one or more heteroatoms. Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl. As used herein, the term "heteroaryl" also includes polycyclic ring systems (e.g., bicyclic, tricyclic or tetracyclic). Examples of bicyclic heteroaryl rings include, but are not limited to: indazole, pyrazolopyrimidine, imidazopyridine, etc.

As used herein, the term "alkoxy" refers to an alkyl group, as previously defined, attached to the molecule through an oxygen atom. An alkoxy group may be represented by —O—($C_{x-y}$ alkyl), wherein x and y represent the minimum and maximum number of carbons of the alkyl chain. Examples of "alkoxy" include, but are not limited to, methoxy (-OMe), ethoxy (-OEt), etc.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be, for example —CFHCH$_2$CHF$_2$ and a $C_{1-2}$haloalkoxy could be, for example —OC(Br)HCHF$_2$.

The term "fluoroalkyl" means alkyl substituted with one or more fluorine atoms. This term includes perfluorinated alkyl groups, such as —CF$_3$ and —CF$_2$CF$_3$.

The term "fluoroalkoxy" means alkoxy substituted with one or more fluorine atoms. This term includes perfluorinated alkoxy groups, such as —OCF$_3$ and —OCF$_2$CF$_3$.

As used herein, the term "cyano" refers to —CN or —C≡N.

As used herein, an "amino" group refers to —NH$_2$.

The term "hydroxyl" or "hydroxy" refers to —OH.

As used herein, a "carbonyl", used alone or in connection with another group refers to —C(O)—.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Substituents, such as for example, $R^1$, $R^2$, and $R^3$ are generally defined when introduced and retain that definition throughout the specification and in all independent claims, unless otherwise specified.

When Z is not hydrogen, the compounds of Formula I are phosphate ester prodrugs, and pharmaceutically acceptable salts thereof, of compounds of Formula II, which are useful as sGC stimulators. For Formula II, the definitions of all variables are the same as those presented for Formula I.

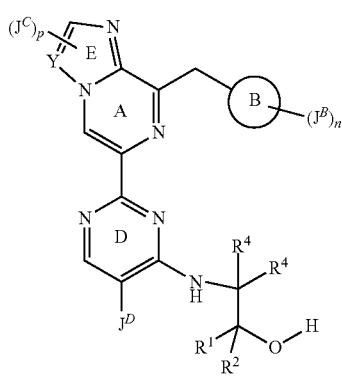

Formula II

The in vivo biological activity exhibited by compounds of Formula I upon administration is mainly due to the presence of the parent compound of Formula II that results from cleavage of the prodrug after administration.

The term "prodrug" refers to compounds which are drug precursors which, following administration and absorption, release the drug in vivo via some metabolic, enzymatic, hydrolytic or rapid chemical conversion process. In general, a prodrug possesses less biological activity than the parent compound against the target by itself, before cleavage to the parent drug. A prodrug may improve the physical properties of the parent drug and/or improve overall drug efficacy, for example through the reduction of toxicity and unwanted side effects of a drug by controlling its absorption, blood levels, metabolic distribution and cellular uptake. Prodrugs may also reduce pharmacokinetic inter-subject variability in vivo. A prodrug may also display more desirable pharmaceutical properties and, as such, a prodrug may also improve the formulability of a drug or facilitate the formulability of the drug for certain modes of administration.

The term "parent drug" or "parent compound" refers to the biologically active entity that is released via a metabolic, enzymatic, hydrolytic or rapid chemical conversion process, following administration of the prodrug. In some embodiments, the parent compound may also be the starting material used for the preparation of the prodrug.

The monovalent cations described by M$^+$ comprise Na$^+$, K$^+$ or the monovalent cation of an organic amine, such as primary, secondary and tertiary amines, cyclic amines, arginine, caffeine, choline, diethylamine, 2-diethylaminoethanol, 2-dimethylaminoethanol, ethanolamine, N-ethylmorpholine, N-ethylpiperidine, glucosamine, histidine, isopropylamine, lysine, morpholine, piperidine, triethylamine, trimethylamine, tripropylamine, diisopropylethylamine and the like.

The divalent cations described by D$^{2+}$ comprise Ca$^{2+}$, Zn$^{2+}$, Cs$^{2+}$, Mg$^{2+}$ or the divalent cation of an organic amine, such as N, N1-dibenzylethylenediamine, ethylenediamine, piperazine, and the like.

Compound Embodiments

In a first embodiment, the compound of the present invention is represented by Formula I or a pharmaceutically acceptable salt thereof. The definitions of the variables of Formula I are as described above. In a specific embodiment, for compounds of Formula I, ring B is a phenyl or a 5 or 6-membered heteroaryl ring, containing 1 or 2 ring heteroatoms selected from N and S; and the definitions for the remaining variables are as described above for Formula I. In another specific embodiment, for compounds of Formula I, ring B is a phenyl or a 5 or 6-membered heteroaryl ring, containing 1 or 2 ring nitrogen atoms.

In a second embodiment, the compound of Formula I is represented by Formula IA, Formula IB, FormulaII, Formula IIA, or Formula IIB or a pharmaceutically acceptable salt thereof:

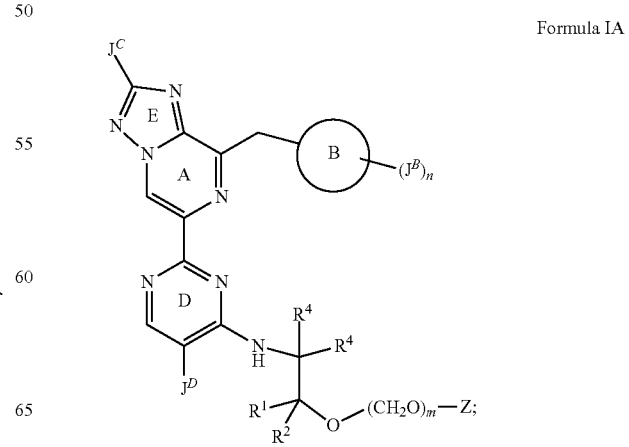

Formula IA

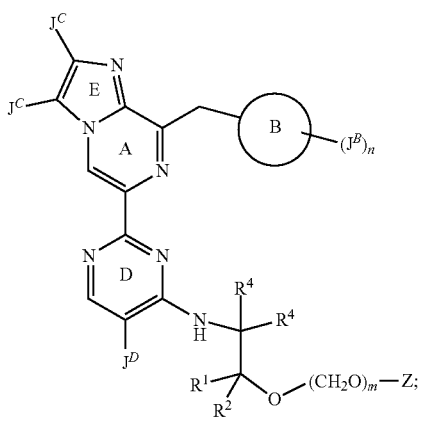

Formula IB

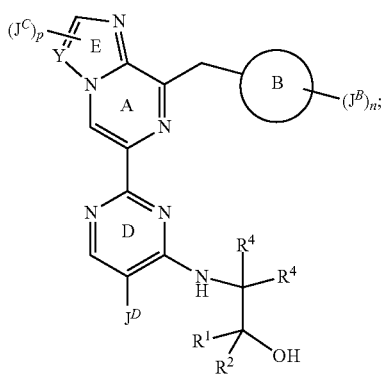

Formula II

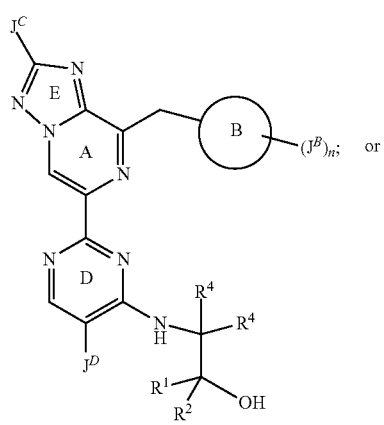

Formula IIA

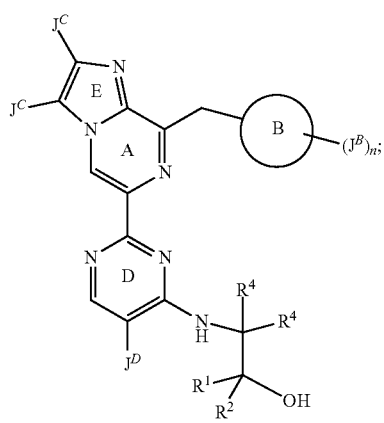

Formula IIB wherein the definitions for the variables of Formula IA, Formula IB, Formula II, Formula IIA, and Formula IIB are the same as those described for Formula I. In a specific embodiment, the compound of Formula I is a compound of Formula IIA or Formula IIB or a pharmaceutically acceptable salt thereof. In another specific embodiment, the compound of Formula I is a compound of Formula IA or Formula IB or a pharmaceutically acceptable salt thereof.

In a third embodiment, for compounds of Formula I, Formula IA, Formula IB, Formula II, Formula IIA, or Formula IIB, or a pharmaceutically acceptable salt thereof, $J^D$ is hydrogen, chloro, fluoro, methoxy or —CN; and the definitions for the remaining variables are as described above for Formula I. In a specific embodiment, $J^D$ is hydrogen, chloro, fluro or —CN. In another specific embodiment, $J^D$ is fluoro, chloro or hydrogen. In another specific embodiment, $J^D$ is hydrogen. In yet another specific embodiment, $J^D$ is fluoro. In another specific embodiment, $J^D$ is cyano. In another specific embodiment, $J^D$ is methoxy. In yet another specific embodiment, $J^D$ is chloro.

In a fourth embodiment, for compounds of Formula I, Formula IA, Formula IB, Formula II Formula IIA or Formula IIB or a pharmaceutically acceptable salt thereof, each $J^C$ is independently selected from the group consisting of hydrogen, $C_{1-2}$ alkyl, $C_{1-2}$ alkoxy, $C_{1-2}$ fluoroalkyl, $C_{1-2}$ fluoroalkoxy, halogen and —CN, wherein each said $C_{1-2}$ alkyl and $C_{1-2}$ alkoxy is optionally and independently substituted by up to 3 instances of $C_{1-4}$ alkoxy, $C_{1-4}$haloalkoxy, —OH or halogen; and the definitions for the remaining variables are as described above in the second or third embodiment. In a specific embodiment, each $J^C$ is independently hydrogen, $C_{1-2}$ alkyl, $C_{1-2}$ alkoxy, $C_{1-2}$ fluoroalkyl, $C_{1-2}$ fluoroalkoxy, halogen or —CN. In another specific embodiment, $J^C$ is hydrogen or halogen. In another specific embodiment, $J^C$ is fluoro or chloro. In yet another specific embodiment, $J^C$ is hydrogen.

In a fifth embodiment, the compound of Formula I is represented by Formula IIIA, Formula IIIB, Formula IVA, Formula IVB, Formula VA, Formula VB, Formula VIA, or Formula VIB, or a pharmaceutically acceptable salt thereof:

Formula IIIA

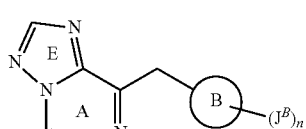

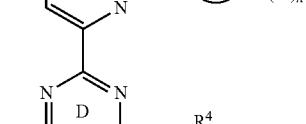

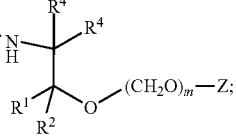

Formula IIIB

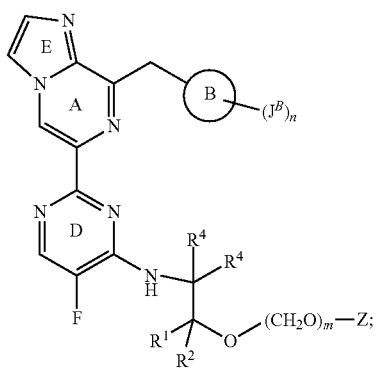

Formula IVA

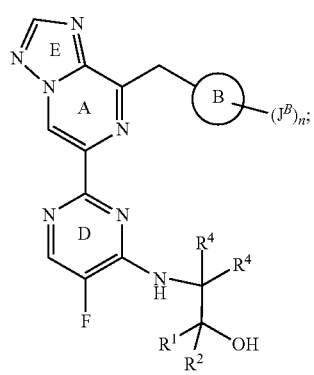

Formula IVB

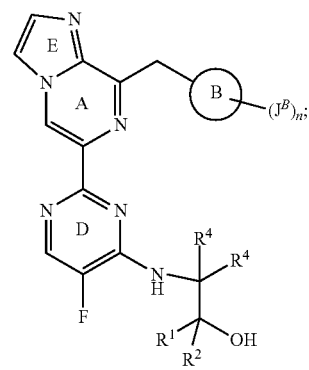

Formula VA

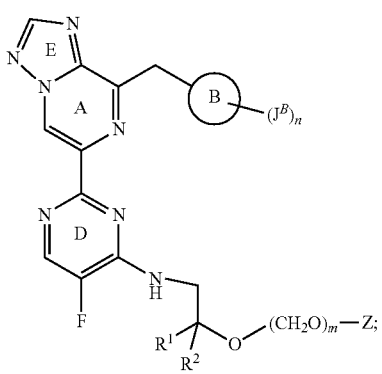

Formula VIA

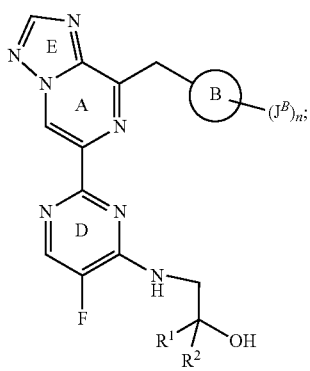

Formula VB

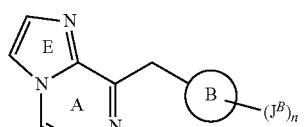; or

Formula VIB

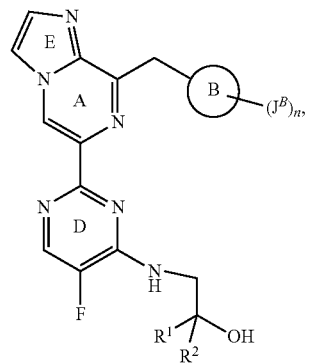

wherein the definitions for the variables are as same as those described for Formula I. In one specific embodiment, the compound of Formula I is represented by VA, Formula VB, Formula VIA, or Formula VIB or a pharmaceutically acceptable salt thereof. In another specific embodiment, the compound of Formula I is represented by Formula IIIA, Formula IIIB, Formula IVA, Formula IVB or a pharmaceutically acceptable salt thereof. In another specific embodiment, the compound of Formula I is represented by Formula VIA or Formula VIB or a pharmaceutically acceptable salt thereof. In yet another specific embodiment, the compound of Formula I is represented by Formula IVA or Formula IVB or a pharmaceutically acceptable salt thereof.

In a sixth embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, or Formula VIB, or a pharmaceutically acceptable salt thereof, ring B is phenyl; and the remaining variables are as described in the first, second, third, fourth or fifth embodiment. Also included in the sixth embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, or Formula VIB, or a pharmaceutically acceptable salt thereof, ring B is a 5 or 6-membered heteroaryl ring, containing 1 or 2 ring heteroatoms independently selected from N, O and S. In a specific embodiment, ring B is a 6-membered heteroaryl ring, containing 1 or 2 ring nitrogen atoms.

In a seventh embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, or Formula VIB, or a pharmaceutically acceptable salt thereof, n is 1, 2 or 3, and $J^B$ is independently halogen or $C_{1-6}$ aliphatic (preferably, a $C_{1-4}$alkyl); and the remaining variables are as described in the sixth embodiment. In a specific embodiment, n is 1 or 2, and $J^B$ is independently halogen or $C_{1-6}$ aliphatic (preferably, a $C_{1-4}$alkyl). In a specific embodiment, n is 1 or 2 and each $J^B$ is fluoro. In another specific embodiment, n is 1 and $J^B$ is fluoro. In another specific embodiment, n is 1; and $J^B$ is a $C_{1-4}$alkyl. In yet another specific embodiment, n is 1; and $J^B$ is methyl. In another specific embodiment, n is 3; and $J^B$ is independently halogen or a $C_{1-4}$alkyl. In yet another specific embodiment, n is 3; and $J^B$ is independent fluoro or methyl.

In an eighth embodiment, the compound of the present invention is represented by Formula VIIA, Formula VIIIA, Formula VIIB or Formula VIIIB, or a pharmaceutically acceptable salt thereof:

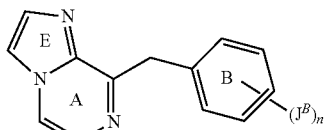

Formula VIIA

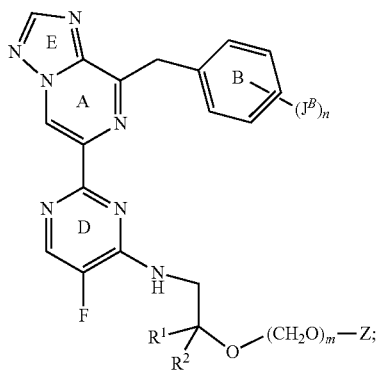

Formula VIIIA

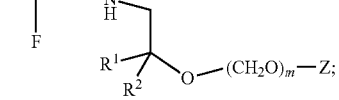

Formula VIIB

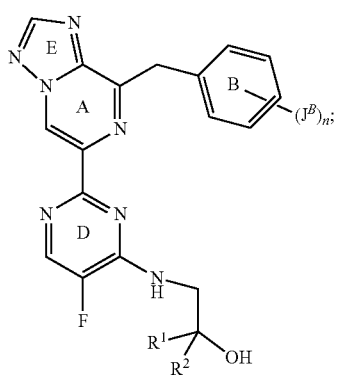

Formula VIIIB wherein the variables are as described for Formula I in the first or sixth embodiment. In a specific embodiment, the compound of the present invention is represented by Formula VIIA or Formula VIIB or a pharmaceutically acceptable salt thereof. In another specific embodiment, the compound of the present invention is represented by Formula VIIIA or Formula VIIIB or a pharmaceutically acceptable salt thereof.

In a ninth embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, Formula VIB, Formula VIIA, Formula VIIB, Formula VIIIA, or Formula VIIIB or a pharmaceutically acceptable salt thereof, $R^1$ is $C_{1-2}$ alkyl, $C_{1-2}$ fluoroalkyl, hydrogen or —C(O)NH$_2$; and the definitions for the remaining variables are as described in the first, second, third, fourth, fifth, sixth, seventh or eighth embodiment. In another specific embodiment, $R^1$ is $C_{1-2}$ fluoroalkyl or —C(O)NH$_2$; and the definitions for the remaining variables are as described in the first, second, third, fourth, fifth, sixth, seventh or eighth embodiment.

In a tenth embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, Formula VIB, Formula VIIA, Formula VIIB, Formula VIIIA, or Formula VIIIB or a pharmaceutically acceptable salt thereof, $R^2$ is $C_{1-2}$ fluoroalkyl, $C_{1-2}$ alkyl or hydrogen and the definitions for the remaining variables are as described in the first, second, third, fourth, fifth, sixth, seventh, eighth or ninth embodiment. In another specific embodiment, $R^2$ is $C_{1-2}$ fluoroalkyl, and the definitions for the remaining variables are as described in the first, second, third, fourth, fifth, sixth, seventh, eighth or ninth embodiment.

In an eleventh embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, Formula VIB, Formula VIIA, Formula VIIB, Formula VIIIA, or Formula VIIIB or a pharmaceutically acceptable salt thereof, $R^1$ is $C_{1-2}$ fluoroalkyl or —C(O)NH$_2$; $R^2$ is $C_{1-2}$ fluoroalkyl; and the definitions for the remaining variables are as described in the first, second, third, fourth, fifth, sixth, seventh or eighth embodiment.

In a twelfth embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, Formula VIB, Formula VIIA, Formula VIIB, Formula VIIIA, or Formula VIIIB or a pharmaceutically acceptable salt thereof, $R^1$ is trifluoromethyl or —C(O)NH$_2$; $R^2$ is trifluoromethyl; and the definitions for the remaining variables are as described in the first, second, third, fourth, fifth, sixth, seventh or eighth embodiment.

In a thirteenth embodiment, for compounds of Formula I, Formula IA, Formula IB, Formula II, Formula IIA, Formula IIB, Formula IIIA, Formula IIIB, Formula IVA, Formula IVB, Formula VA, Formula VB, Formula VIA, Formula VIB, Formula VIIA, Formula VIIB, Formula VIIIA, or Formula VIIIB or a pharmaceutically acceptable salt thereof, $R^1$ and $R^2$ are both hydrogen or $C_{1-2}$alkyl; or one of $R^1$ and $R^2$ is hydrogen, and the other is $C_{1-2}$fluoroalkyl; and the definitions for the remaining variables are as described in the first, second, third, fourth, fifth, sixth, seventh or eighth embodiment. In a specific embodiment, $R^1$ and $R^2$ are both hydrogen. In another specific embodiment, $R^1$ and $R^2$ are both methyl. In yet another specific embodiment, one of $R^1$ and $R^2$ is hydrogen, and the other is trifluoromethyl.

In a fourteenth embodiment, the compound of the present invention is represented by one of the following formulae:

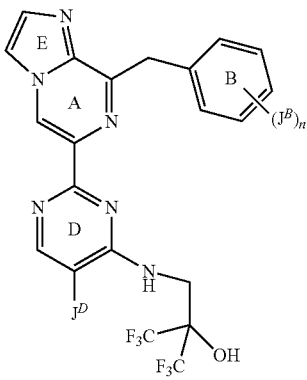

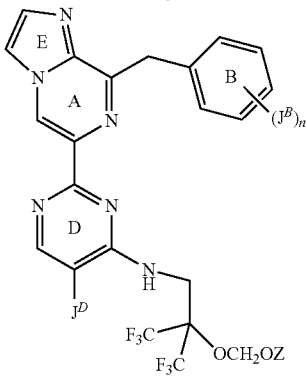

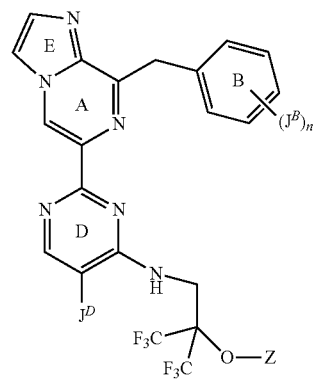

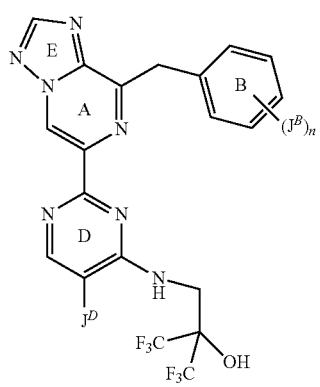

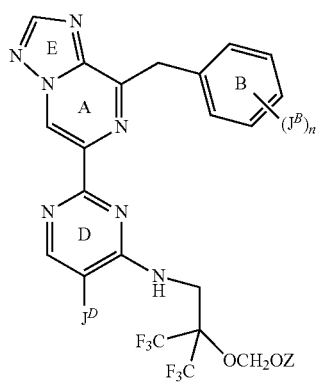

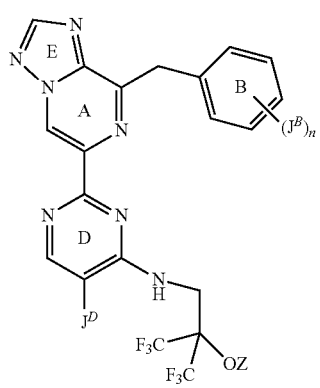

-continued

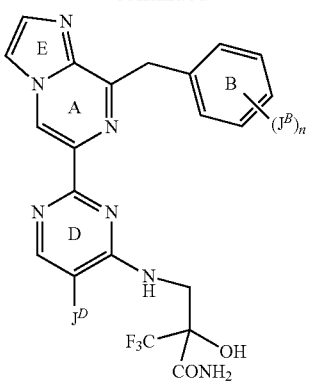

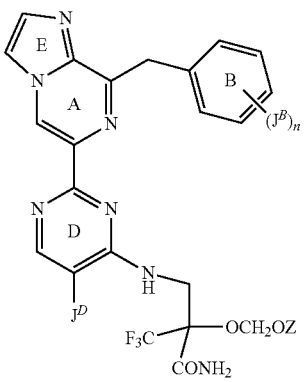

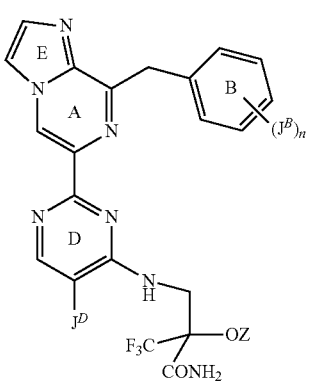

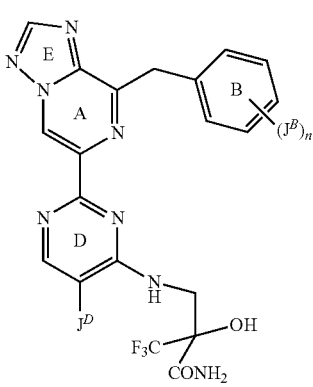

-continued

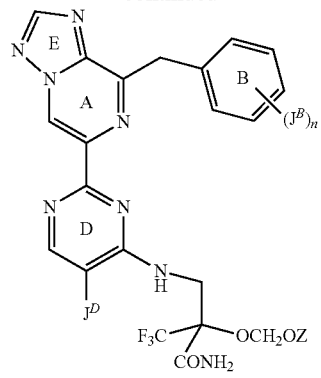

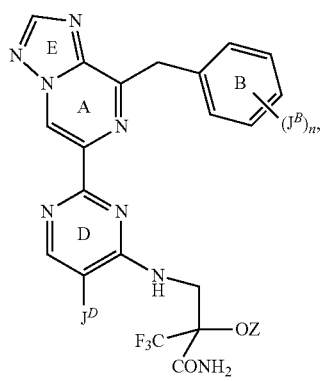

or a pharmaceutically acceptable salt thereof, wherein the definitions for the variables are as described in the first or seventh embodiment. In a specific embodiment, $J^D$ is hydrogen, chloro, fluro or —CN. In a specific embodiment, $J^D$ is halogen. In a specific embodiment, $J^D$ is hydrogen or fluoro. In specific embodiment, $J^D$ is fluoro. In specific embodiment, n is 1 or 2 and $J^B$ is halogen.

In some embodiments, for compounds described in the first, second, third, fourth, fifth, sixth, seventh, eighth, ninth, tenth, eleventh, twelfth, thirteenth or fourteenth embodiment, Z is —P(O)(OH)$_2$.

In some embodiments, for compounds described in the first, second, third, fourth, fifth, sixth, seventh, eighth, ninth, tenth, eleventh, twelfth, thirteenth or fourteenth embodiment, Z is —P(O)(OH)O$^-$ M$^+$ or —P(O)(O$^-$)$_2$(M$^+$); and M$^+$ is Na$^+$, K$^+$ or the monovalent cation of an organic amine. In a specific embodiment, M$^+$ is Na$^+$.

In some embodiments, for compounds described in the first, second, third, fourth, fifth, sixth, seventh, eighth, ninth, tenth, eleventh, twelfth, thirteenth or fourteenth embodiment, Z is —P(O)(O$^-$)$_2$D$^{2+}$; and D$^{2+}$ is Ca$^{2+}$, Cs$^{2+}$, Zn$^{2+}$, Mg$^{2+}$ or the divalent cation of an organic amine.

In some embodiments, the compounds of Formula I are selected from those listed in Table I.

TABLE I
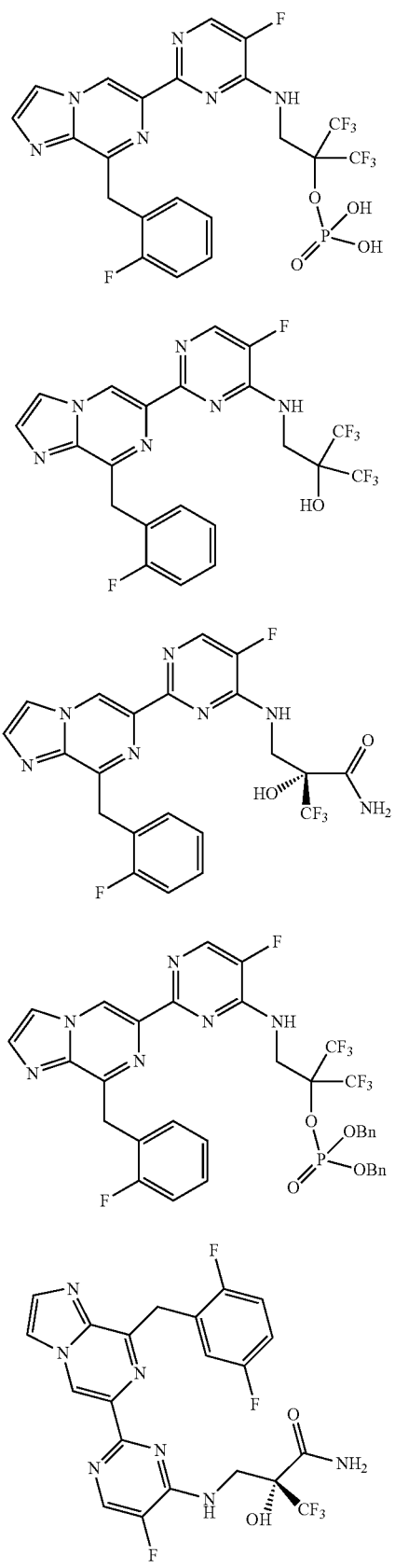
TABLE I-continued
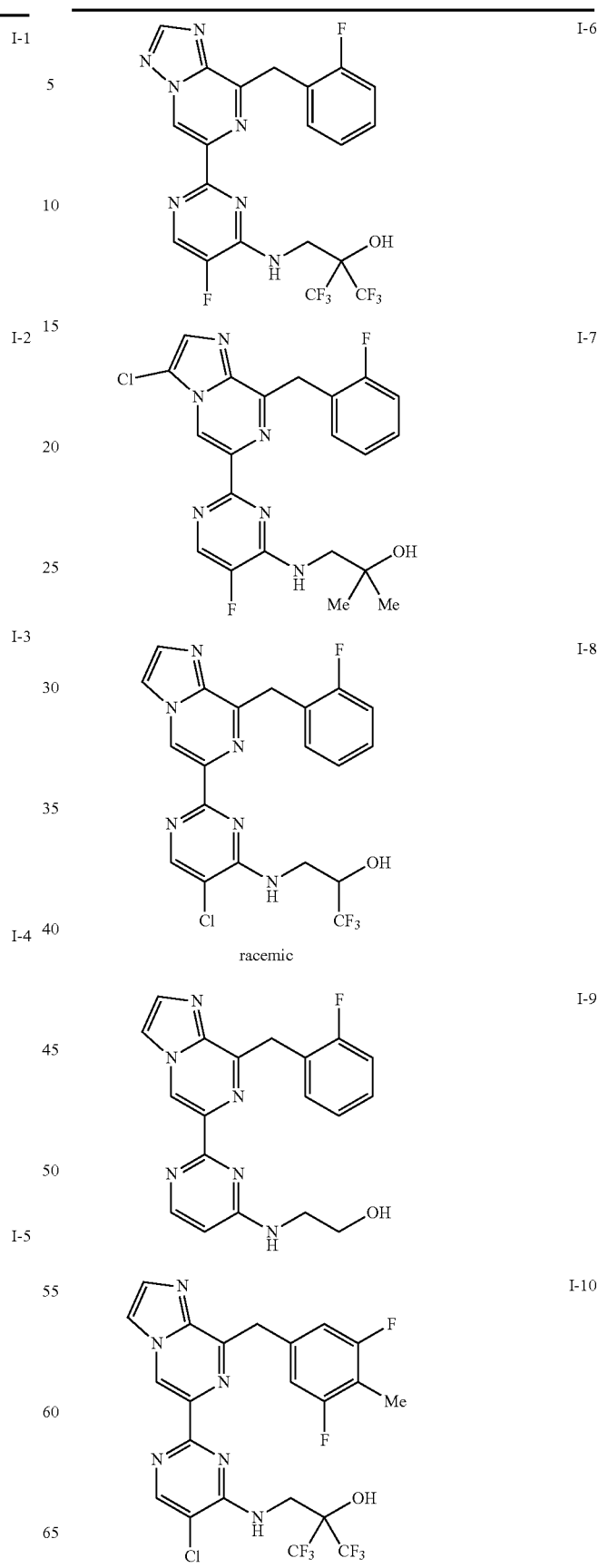

TABLE I-continued

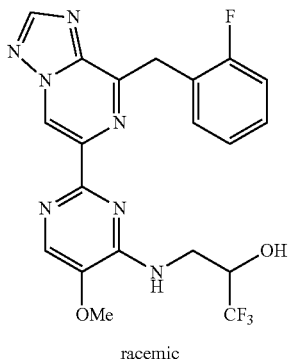 [SMILES: COc1cnc(-c2cn3ncnc3c(Cc3ccccc3F)n2)nc1NCC(O)C(F)(F)F]

I-11 racemic

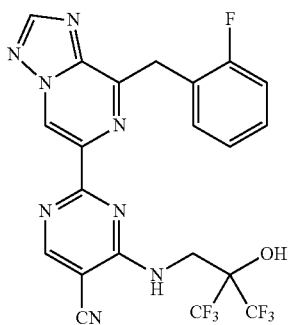 [SMILES: N#Cc1cnc(-c2cn3ncnc3c(Cc3ccccc3F)n2)nc1NCC(O)(C(F)(F)F)C(F)(F)F]

I-12

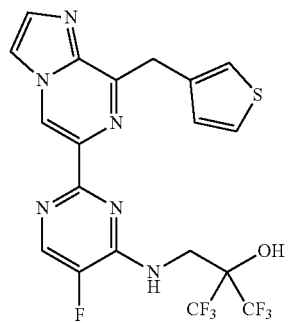 [SMILES: OC(CNc1nc(-c2cn3ccnc3c(Cc3ccsc3)n2)ncc1F)(C(F)(F)F)C(F)(F)F]

I-13

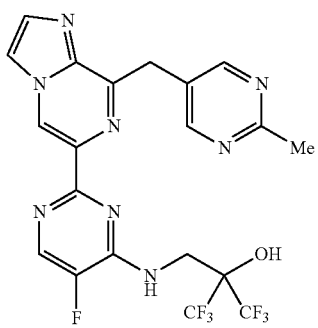 [SMILES: Cc1ncc(Cc2nc(-c3ncc(F)c(NCC(O)(C(F)(F)F)C(F)(F)F)n3)cn3ccnc23)cn1]

I-14

TABLE I-continued

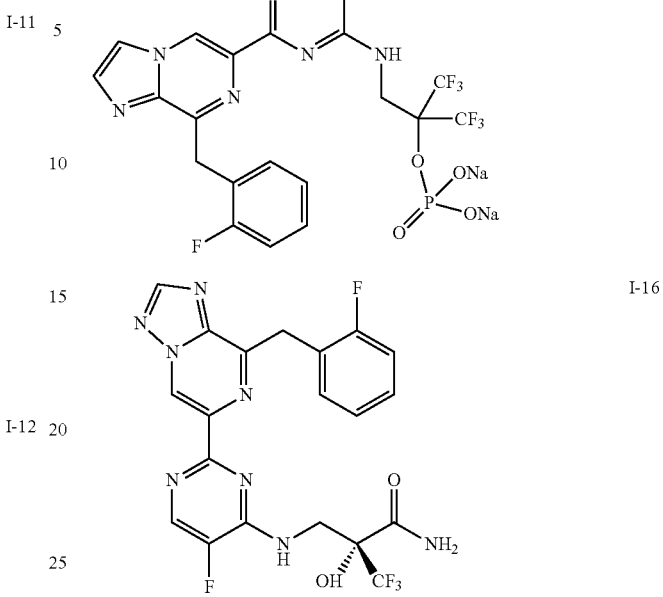

I-15

I-16

Pharmaceutically Acceptable Salts of the Invention.

"Pharmaceutically acceptable salts" of the compounds described herein include those derived from said compounds when mixed with inorganic or organic acids or bases. In some embodiments, the salts can be prepared in situ during the final isolation and purification of the compounds. In other embodiments the salts can be prepared from the free form of the compound in a separate synthetic step. The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

The pharmaceutically acceptable salts of a compound of Formula I are those that may be used in medicine. Salts that are not pharmaceutically acceptable may, however, be useful in the preparation of a compound of Formula I or of their pharmaceutically acceptable salts.

When a compound of Formula I is acidic, suitable "pharmaceutically acceptable salts" refers to salts prepared from pharmaceutically acceptable non-toxic bases including inorganic and organic bases. Salts derived from inorganic bases include aluminum, ammonium, calcium, copper, ferric, ferrous, lithium, magnesium, manganic, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines, arginine, betaine, caffeine, choline, N, $N^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of Formula I is basic, salts may be prepared from pharmaceutically acceptable non-toxic acids, including inorganic and organic acids. Such acids include acetate, acetic, acid citrate, acid phosphate, ascorbate, benzenesulfonic, benzenesulfonate, benzoic, benzoate, bromide, bisulfate, bitartrate, camphorsulfonic, chloride, citrate, citric, ethanesulfonate, ethanesulfonic, formate, fumarate, fumaric, gentisinate, gluconate, gluconic, glucuronate, glutamate, glutamic, hydrobromic, hydrochloric, iodide, isethionic, isonicotinate, lactate, lactic, maleate, maleic, malic, mandelic, methanesulfonic, methanesulfonate, mucic, nitrate, nitric, oleate, oxalate, pamoic, pamoate (i.e., 1,1'-methylene-bis-(2-hydroxy-3-naphthoate)), pantothenic, pantothenate, phosphate, phosphoric, saccharate, salicylate, succinic, succinate, sulfuric, sulfate, tannate, tartrate, tartaric, p-toluenesulfonate, p-toluenesulfonic acid and the like. Particular embodiments include citric, hydrobromic, hydrochloric, maleic, phosphoric, sulfuric and tartaric acids.

In addition to the compounds described herein, their pharmaceutically acceptable salts may also be employed in compositions to treat or prevent the herein identified diseases.

Pharmaceutical Compositions and Methods of Administration.

The compounds herein disclosed, and their pharmaceutically acceptable salts thereof may be formulated as pharmaceutical compositions or "formulations".

A typical formulation is prepared by mixing a compound of Formula I, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I or pharmaceutical composition thereof) or aid in the manufacturing of the pharmaceutical product (i.e., medicament).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

The formulations may be prepared using conventional dissolution and mixing procedures. The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically effective amount of the compound to be administered will be governed by such considerations, and is the minimum amount necessary to ameliorate, cure or treat the disease, or one or more of its symptoms.

The terms "administer", "administering" or "administration" in reference to a compound, composition or dosage form of the invention means introducing the compound into the system of the subject or patient in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g. orally (including, but not limited to solid dosage forms including hard or soft capsules (e.g. gelatin capsules), tablets, pills, powders, sublingual tablets, troches, lozenges, and granules; and liquid dosage forms including, but are not limited to, pharmaceutically acceptable emulsions, microemulsions, aqueous or oil solutions, suspensions, syrups and elixirs, by inhalation (e.g. with an aerosol, gas, inhaler, nebulizer or the like), to the ear (e.g. using ear drops), topically (e.g. using creams, gels, inhalants, liniments, lotions, ointments, patches, pastes, powders, solutions, sprays, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via ear drops, via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Formulations of a compound intended for oral use may be prepared according to any method known to the art for the manufacture of pharmaceutical compositions.

In solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The oral compositions (either solid or liquid) can also include excipients and adjuvants such as dispersing or wetting agents, such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate); emulsifying and suspending agents, such as sodium carboxymethylcellulose, croscarmellose, povidone, methylcellulose, hydroxypropyl methylcelluose, sodium alginate, polyvinylpyrrolidone, gum tragacanth and gum acacia; sweetening, flavoring, and perfuming agents; and/or one or more preservatives such as ethyl or n-propyl p-hydroxy-benzoate, one or more coloring agents, one or more flavoring agents and one or more sweetening agents, such as sucrose or saccharin.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs. The active component is admixed under sterile conditions with a pharmaceutically acceptable carrier and any needed preservatives or buffers as may be required.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I include Tween™-60, Span™-80, cetostearyl alcohol, benzyl alcohol, myristyl alcohol, glyceryl mono-stearate and sodium lauryl sulfate.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

Sterile injectable forms of the compositions described herein (e.g. for parenteral administration) may be aqueous or oleaginous suspension. These suspensions may be formulated according to techniques known in the art using suitable dispersing or wetting agents and suspending agents (including those described in the preceding paragraph). The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as a vegetable oil, for example arachis oil, olive oil, sesame oil or coconut oil, especially in their polyoxyethylated versions, or in mineral oil such as liquid paraffin., These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

In another aspect, a compound of Formula I or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Therapeutic Methods

In another aspect, the invention also provides a method of treating a disease in a subject in need thereof, comprising administering, alone or in combination therapy, a therapeutically effective amount of a compound of Formula I, or a pharmaceutically acceptable salt thereof to the subject; wherein the disease is one that benefits from sGC stimulation or from an increase in the concentration of NO or cGMP or both, or from the upregulation of the NO pathway. The invention also provides a method of treating a disease in a subject in need thereof, comprising administering, alone or in combination therapy, a pharmaceutical composition comprising a compound of Formula I, or a pharmaceutically acceptable salt thereof to the subject or a dosage form comprising the pharmaceutical composition, wherein the disease is one that benefits from sGC stimulation or from an increase in the concentration of NO or cGMP or both, or from the upregulation of the NO pathway.

In some embodiments, the compounds here disclosed are sGC stimulators that may be useful in the prevention and/or treatment of diseases characterized by undesirable reduced bioavailability of and/or sensitivity to NO, such as those associated with conditions of oxidative stress or nitrosative stress.

Increased concentration of cGMP leads to vasodilation, inhibition of platelet aggregation and adhesion, anti-hypertensive effects, anti-remodeling effects, anti-apoptotic effects, anti-inflammatory, anti-fibrotic effects, metabolic effects and neuronal signal transmission effects. Thus, sGC stimulators may be used to treat and/or prevent a range of diseases.

Specific diseases or disorders which may be treated and/or prevented by administering an sGC stimulator of the invention (e.g., a compound of Formula I and Table I and pharmaceutically acceptable salts thereof), include but are not limited to:

Abetalipoproteinemia, achalasia (e.g., esophageal achalasia), acute respiratory distress syndrome (ARDS), adhesive capsulitis, age-related learning and memory disturbances, age-related memory loss, alcoholism, alopecia or hair loss, altitute sickness, Alzheimer's disease (including pre-Alzheimer's disease, mild to moderate Alzheimer's disease and moderate to severe Alzheimer's disease), amyotrophic lateral sclerosis (ALS or Lou Gehrig's disease), anal fissures, aneurysm, angina (e.g., stable or unstable angina pectoris, variant angina, Prinzmetal's angina, microvascular angina), anxiety or anxiety disorders, arginosuccinic aciduria, arterial and venous thromboses, arthritis, Asperger's syndrome, asthma and asthmatic diseases, ataxia, telangliectasia, atherosclerosis (e.g., atherosclerosis associated with endothelial injury, platelet and monocyte adhesion and aggregation, smooth muscle proliferation or migration), atrophic vaginitis, attention deficit disorder (ADD) and attention deficit hyperactivity disorder (ADHD), autism and disorders in the autism spectrum, benign prostatic hyperplasia (BPH) or hypertrophy or enlargement, bipolar disorder, bladder outlet obstruction, bladder pain syndrome (BPS), blepharitis, bone and carbohydrate metabolism disturbances, bone healing (e.g. bone healing following osteoclastic bone remodeling, osteoclastic bone resorption, new bone formation), brain aneurysm, brain hypoxia, cancer metastasis, cerebral amyloid angiopathy (CAA) or congophilic angiopathy, cerebral autosomal-dominant arteriopathy with subcortical infarcts and leukoencephalopathy (CADASIL or CADASIL syndrome), cerebral perfusion, cerebral small vessel disease, cerebral vasospasm, chemo-brain, childhood disintegrative disorder, chronic bronchitis, chronic fatigue, chronic traumatic encephalopathy (CTE), ciliopathies, cirrhosis (e.g., liver cirrhosis, liver cirrhosis associated with chronic liver disease, primary biliary cirrhosis), CNS-disease related sexual dysfunction, CNS-disease related sleep disturbances, cognitive defect associated with Huntington's Disease, cognitive dysfunction, cognitive impairment (e.g., vascular cognitive impairment, mild cognitive impairment, cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell disease, concussion, congenital myasthenic syndrome, connective tissue disease, consequences of cerebral infarction (apoplexia cerebri), conservation of blood substituents in trauma patients, CREST syndrome, Crohn's disease, cystic fibrosis (CF), delusional disorder, dementia (e.g., vascular dementia, post-stroke dementia, Lewy body dementia, dementia with frontal lobe degeneration, dementia with frontotemporal lobar degeneration, dementia with corticobasal degeneration, Creutzfeldt-Jakob dementia, HIV-dementia, multi-infarct dementia, post-operative dementia, strategic single-infarct dementia, HIV-associated dementia (including asymptomatic neurocognitive impairment (ANI), minor neurocognitive disorder (MND), HIV-associated dementia (HAD, also called AIDS dementia complex [ADC] or HIV encephalopathy), pre-senile dementia (mild cognitive impairment, MCI), mixed dementia, Binswanger's dementia (subcortical arteriosclerotic encephalopathy), Parkinson's Dementia), demyelination, depression, depressive disorder, dermatomyositis, diabetic angiopathy, diabetic macular edema, diabetic microangiopathies, diabetic ulcers or wounds (e.g., diabetic food ulcer), diseases associated with or related to metabolic syndrome (e.g. obesity, diabetes, insulin resistance, elevated fasting glucose, elevated fasting insulin, elevated lipids), diseases involving downregulated neurotransmitters, diseases involving impaired cerebral blood flow, diseases involving impaired neurodegeneration, diseases involving impaired synaptic function, diseases involving neuroinflammation, diseases involving neurotoxicity, diseases of the organs of the male and female urogenital system (benign and malignant), disturbances of concentration in children with learning and memory problems, Down syndrome, drug addiction, drug-induced psychosis, dry eye syndrome, Duchenne muscular dystrophy, Dupuytren's contracture, dyskinesia (e.g., acute dyskinesia, chronic or tardive dyskinesia, non-motor dyskinesia, levo-dopa induced dyskinesia (LID)), dysmenhorrea (e.g., primary dysmenhorrea, secondary dysmenhorrea), dyspaneuria, dysphagia, dystonia (e.g., generalized dystonia, focal dystonia, segmental dystonia, sexual dystonia, intermediate dystonia, acute dystonic reaction, genetic or primary dystonia), edema, elecrolyte disturbances (e.g., herkalemia, hyponatremia), emphysema, endometriosis, endothelial dysfunction or injury and diseases associated with endothelial dysfunction, erectile dysfunction, esophageal achalasia, Fabry Disease, female sexual dysfunction (e.g., female sexual arousal dysfunction), fibromyalgia, fibrosis (e.g., endomyocardial fibrosis, atrial fibrosis, cardiac interstitial fibrosis, cardiac fibrosis, pulmonary fibrosis, eye fibrosis, skin fibrosis, intestinal fibrosis, renal or kidney fibrosis, interstitial renal fibrosis, pulmonary fibrosis, idiopathic pulmonary fibrosis, progressive massive fibrosis of the lungs, liver fibrosis, mediastinal fibrosis, retroperitoneal fibrosis, arthrofibrosis, bone marrow fibrosis, myelofibrosis, osteomyelofibrosis, radiation-induced fibrosis, pancreatic fibrosis), Fragile X, functional dyspepsia, gastroparesis, Gaucher Disease, general disturbances of concentration, general psychosis, glaucoma, glioblastoma, glomerulopathies (e.g., glomerulonephritis, acute glomerulonephritis, glomerulosclerosis, focal segmental glomerulosclerosis), granulomas, head injury, hearing impairment (e.g., partial hearing loss, total hearing loss, partial deafness, total deafness, noise-induced hearing loss), heart disease (e.g., left ventricular myocardial remodeling, left ventricular systolic dysfunction, ischemic cardiomyopathy, dilatated cardiomyopathy, alcoholic cardiomyopathy, storage cardiomyopathies, congenital heart defects, decreased coronary blood flow, diastolic or systolic dysfunction, coronary insufficiency, acute coronary syndrome, coronary artery disease, arrhythmias, reduction of ventricular preload, cardiac hypertrophy, right heart hypertrophy, disturbances of atrial and ventricular rhythm and heart conduction disturbances, atrioventricular blocks of degree I-III (AVB I-III), supraventricular tachyarrhythmia, premature ventricular contraction, atrial fibrillation, atrial flutter, ventricular fibrillation, ventricular flutter, ventricular tachyarrhythmia, torsade-depointes tachycardia, atrial and ventricular extrasystoles, AV-junction extrasystoles, sick-sinus syndrome, AV-node reentry tachycardia, Wolff-Parkinson-White syndrome, myocardial insufficiency, chronic, acute or viral myocarditis, cardiogenic shock, cardiac remodeling), heart failure (HF; e.g.: Heart failure with preserved ejection fraction (HFPEF), Heart failure with reduced ejection fraction (HFREF), acute heart failure, chronic heart failure, acute phases of an existing chronic heart failure (worsening HF), transient heart failure, post-acute heart failure, systolic heart failure, diastolic heart failure, congestive heart failure, acute decompensated heart failure, right ventricular failure, total heart failure, high output heart failure, heart failure with valvular defects, diabetic heart failure, heart failure/cardiorenal syndrome, right heart failure), high concentration of plasminogen activator inhibitor 1 (PA-1), high levels of fibrinogen and low density DLD, histiocytosis X, Huntington's disease or chorea (HD), hyperammonemia and related, hypertension (e.g., arterial hypertension, resistant hypertension, diabetic hypertension, idiopathic hypertension, essential hypertension, secondary hypertension, gestational hypertension, portal hypertension, systemic hypertension, pre-eclampsia, increased acute and chronic coronary blood pressure), hypertonia, hypertrophic scars, hypoactive sexual arousal disorder, hypoperfusion, impotence, Inflammatory bowel disease (e.g., Crohn's disease, Ulcerative Colitis), inflammation caused by cerebral malaria, inflammation caused by infectious disease, inflammatory response in perioprative care, platelet aggregation, intellectual disability, intermittent claudication, interstitial cystitis (IC), intradialytic hypotension, ischemia (e.g., cerebral ischemia, myocardial ischemia, thromboembolic ischemia, critical limb ischemia), keloids, kidney disease (e.g., chronic kidney disease, acute and chronic renal failure, acute and chronic renal insufficiency, sequelae of renal insufficiency, renal-insufficiency related to pulmonary enema, renal-insufficiency related to HF, renal-insufficiency related to uremia or anemia, primary kidney disease, congenital kidney disease, polycystic kidney disease progression, kidney transplant rejection, immune complex-induced kidney disease, abnormally reduced creatinine and/or water excretion, abnormally increased blood concentrations of urea, nitrogen, potassium and/or creatinine, altered activity of renal enzymes (e.g. glutamyl synthetase), altered urine osmolarity or urine volume, increased microalbuminuria, macroalbuminuria, lesions of glomeruli and arterioles, tubular dilatation, hyperphosphatemia, vascular kidney disease, renal cysts, renal edema due to HF), Korsakoff psychosis, leukocyte activation, levo-dopa induced addictive behavior, lichen sclerosus, lipid related disorders (e.g., excessive adiposity, excessive subcutaneous fat, hyperlipidemias, dyslipidemia, hypercholesterolemias, decreased high-density lipoprotein cholesterol (HDL-cholesterol), moderately elevated low-density lipoprotein cholesterol (LDL-cholesterol) levels, hypertriglyceridemias, hyperglyceridemia, hypolipoproteinanemias, sitosterolemia, fatty liver disease, liver steatosis or abnormal lipid accumulation in the liver, steatosis of the heart, kidney or muscle, sitosterolemia, xanthomatosis, Tangier disease), liver diseases (e.g., vascular liver disease, hepatic stellate cell activation, hepatic fibrous collagen and total collagen accumulation, liver disease of necro-inflammatory and/or of immunological, cholestatic liver disease associated with granulomatous liver diseases, cholestatic liver disease associated with liver malignancies, cholestatic liver disease associated with intrahepatic cholestasis of pregnancy, cholestatic liver disease associated with hepatitis, cholestatic liver disease associated with sepsis, cholestatic liver disease associated with drugs or toxins, cholestatic liver disease associated with graft-versus-host disease, cholestatic liver disease associated with post-liver transplantation, cholestatic liver disease associated with choledocholithiasis, cholestatic liver disease associated with bile duct tumors, cholestatic liver disease associated with pancreatic carcinoma, cholestatic liver disease associated with Mirizzi's syndrome, cholestatic liver disease associated with AIDS, cholangiopathy, cholestatic liver disease associated with parasites, cholestatic liver disease associated with schistosomiasis, hepatitis, non-alcoholic steatohepatitis (NASH), non-alcoholic fatty liver disease (NAFLD), hepatic vaso-occlusive disease (VOD), hepatic sinusoidal obstruction syndrome (SOS), hepatic encephalopathy), localized thrombosis, lower urinary tract syndromes (LUTS), lumbar spinal canal stenosis, lupus nephritis, lupus or Systemic Lupus Erythematosus, microalbuminuria, microcirculation abnormalities, migraines, minor neurocognitive disorder (MND), morphea, moyamoya, multiple lacunar infarction, multiple organ dysfunction syndrome (MODS), multiple organ failure (MOF), multiple sclerosis (MS, including clinically isolated syndrome (CIS), relapsing-remitting MS (RRMS), primary progressive MS (PPMS), secondary progressive MS (SPMS)), multiple system atrophy (MSA), myocardial infarction or heart attack (e.g., ST-segment elevation myocardial infarction, Non-ST-segment elevation myocardial infarction, old myocardial infarction), myopic choroidal neovascularization, naevi, narcotic dependence, nephropathies (e.g., diabetic nephropathy, non-diabetic nephropathy, nephritis, nephropathy induced by toxins, contrast medium induced nephropathy, diabetic or non-diabetic nephrosclerosis, nephrotic syndrome, pyelonephritis, nephrogenic fibrosis), neurodegenerative diseases, neurogenic bladder and incontinence, neuroinflammation, neurologic disorders associated with decreased nitric oxide production, neuromuscular diseases (e.g., Duchenne muscular dystrophy (DMD), Becker muscular dystrophy (BMD), limb girdle muscular dystrophies, distal myopathies, type I and type II myotonic dystrophies, facio-scapulo-peroneal muscular dystrophy, autosomal and X-linked Emery-Dreifuss muscular dystrophy, oculopharyngeal muscular dystrophy, amyotrophic lateral sclerosis, spinal muscle atrophy (SMA)), neuromyelitis optica, neuropathies (e.g., peripheral neuropathy, autonomic neuropathy, central nervous system neuropathy, chemotherapy induced neuropathy, diabetic neuropathy, painful neuropathies, neuropathic pain, non-painful neuropathies, painful diabetic neuropathy, non-painful diabetic neuropathy, neuropathies associated to a CNS disease (e.g., Multiple sclerosis, MS), radiation-induced neuropathy), neuropathic pain associated with shingles, neuropathic pain associated with spine surgery), obsessive compulsive disorder (OCD), obstructive thromboanginitis, obstructive uropathy, oesinophilic fasciitis, osteoporosis, overactive bladder, pain (e.g., acute pain, central pain syndrome, inflammatory pain, postoperative pain, tonic pain, visceral pain, claudication pain, orphan pain indications (e.g., Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, Tolosa-Hunt syndrome)), pancreatitis, panic disorder, Parkinson's disease, Parkinsonism Plus, Parkinson's Dysphagia, pathological eating disorders, pelvic pain, peripheral vascular disease (e.g., peripheral arterial disease, peripheral arterial occlusive disease, peripheral embolism, peripheral perfusion disturbances), peritonitis, pervasive development disorder, Peyronie's disease, Picks syndrome, polychondritis, polymyositis, post herpetic neuralgia, post-traumatic head injury, post-traumatic stress disorder (PTSD), premature ejaculation, progressive nuclear palsy, prostate hypertrophy, pulmonary disease (e.g., plexogenic pulmonary arteriopathy, bronchoconstriction or pulmonary bronchoconstriction, vascular disease of the lung, chronic obstructive pulmonary disease (COPD), pulmonary capillary hemangiomatosis, lymphangiomatosis and compressed pulmonary vessels (e.g., due to adenopathy, tumor or fibrosing mediastinitis), pulmonary vascular remodeling, pulmonary hypertonia), pulmonary hypertension (PH, e.g., pulmonary arterial hypertension (PAH), primary PH, secondary PH, sporatid PH, pre-capically PH, idiopathic PH, PH associated with left ventricular disease, PH associated with HIV, PH associated with SCD, PH associated with thromboembolism (chronic thromboembolic PH or CTEPH), PH associated with sarcoidosis, PH associated with chronic obstructive pulmonary disease, PH associated with acute respiratory distress syndrome (ARDS), PH associated with acute lung injury, PH associated with alpha-1-antitrypsin deficiency (AATD), PH associated with pulmonary emphysema (e.g., smoking induced emphysema), PH associated with lung disease, PH associated with hypoxemia, PH associated with scleroderma, PH associated with cystic fibrosis (CF), PH associated with left ventricular dysfunction, PH associated with hypoxemia, PH (WHO groups I, II, III, IV and V), PH associated with mitral valve disease, PH associated with pericarditis, PH associated with constrictive pericarditis, PH associated with aortic stenosis, PH associated with dilated cardiomyopathy, PH associated with hyperthrophic cardiomyopathy, PH associated with restrictive cardiomyopathy, PH associated with mediastinal fibrosis, PH associated with pulmonary fibrosis, PH associated with anomalous pulmonary venous drainage, PH associated with pulmonary veno-occlusive disease, PH associated with pulmonary vasculitis, PH associated with collagen vascular disease, PH associated with congenital heart disease, PH associated with pulmonary venous hypertension, PH associated with interstitial lung disease, PH associated with sleep-disordered breathing, PH associated with chronic airflow obstruction, PH associated with obstructive sleep apnea, PH associated with central sleep apnea, PH associated with mixed sleep apnea, PH associated with alveolar hypoventilation disorders, PH associated with chronic exposure to high altitude, PH associated with neonatal lung disease, PH associated with alveolar-capillary dysplasia, PH associated with sickle cell disease, PH associated with other coagulation disorders, PH associated with chronic thromboembolism), radiculopathy, Raynaud's disease, Raynaud's syndrome (primary or secondary), refractory epilepsy, Renpennings's syndrome, reperfusion injury (e.g., ischemia-reperfusion damage, ischemia-reperfusion associated with organ transplant), restenosis (e.g., restenosis developed after thrombolysis therapies, after percutaneous transluminal angioplasties (PTAs), after transluminal coronary angioplasties (PTCAs), after heart transplant or after bypass operations), retinopathies (e.g., diabetic retinopathy, non-diabetic retinopathy, non-proliferative diabetic retinopathy, proliferative vitroretinopathy, peripheral retinal degeneration, retinal vein occlusion), Rhett's disorder, rheumatoid or rheumatic disease (e.g., arthritis, rheumatoid arthritis), sarcoidosis, sarcoids, schistosomiasis, schizoaffective disorder, schizophrenia, schizophrenia with dementia, scleroderma (e.g., localized scleroderma or circumscribed scleroderma, systemic scleroderma), sclerosis (e.g. renal sclerosis, progressive sclerosis, liver sclerosis, primary sclerosing cholanginitis, sclerosis of the gastro-intestinal tract, hippocampal sclerosis, focal sclerosis, primary lateral sclerosis, osteosclerosis, otosclerosis, atherosclerosis, tuberous sclerosis, systemic sclerosis), sepsis or septic shock or anaphylactic shock, Sickle Cell Anemia, Sickle Cell Disease, Sjogren's syndrome, sleep-wake disorders, Sneddon's syndrome, spasms (e.g., coronary spasms, vascular spasms, spasms of the peripheral arteries), spinal cord injury, spinal muscular atrophy, spinal subluxations, spinocerebellar ataxias, Steel-Richardson-Olszewski disease (progressive supranuclear palsy), stroke, subarachnoid hemorrhage, subcortical arteriosclerotic encephalopathy, syncopes, tauopathies, tension, thalamic degeneration, thromboembolic or thrombogenic disorders, transient ischemic attacks (TIAs), traumatic brain injury, tubulointerstitial diseases, ulcers, uterine fibroids, vaginal atrophy, valve deffects (e.g., mitral valve stenosis, mitral valve regurgitation, insufficiency or incompetence, aortic valve stenosis, aortic valve insufficiency, tricuspic valve insufficiency, pulmonary valve stenosis, pulmonar valve insufficiency, combined valcular deffects), vascular disease of the brain, vascular disorder resulting from cardiac and renal complications, vascular leakage or permeability, vasculitis (e.g., thrombotic vasculitis, occlusive thrombotic vasculitis, Kawasaki disease, arteritis, aortitis), vaso-occlusive crisis, venus graft failure, wet age-related macular degeneration and Williams syndrome.

The term "disease", as used herein refers to any deviation from or interruption of the normal structure or function of any body part, organ, or system that is manifested by a characteristic set of symptoms and signs and whose etiology, pathology, and prognosis may be known or unknown. The term disease encompasses other related terms such as disorder and condition (or medical condition) as well as syndromes, which are defined as a combination of symptoms resulting from a single cause or so commonly occurring together as to constitute a distinct clinical picture. In some embodiments, the term disease refers to an sGC, cGMP and/or NO mediated medical or pathological disease.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a companion animal or pet (e.g., a dog, cat, mice, rats, hamsters, gerbils, guinea pig or rabbit). In some embodiments, the subject is a human.

The invention also provides a method for treating one of the above diseases in a subject, comprising administering a therapeutically effective amount of a compound of Formula I, or a pharmaceutically acceptable salt thereof, to the subject in need of the treatment. Alternatively, the invention provides a compound of Formula I, or a pharmaceutically acceptable salt thereof, for use in the treatment of one of these diseases in a subject in need of the treatment. Also included in the invention is the use of a compound of Formula I, or a pharmaceutically acceptable salt thereof, for the manufacture of medicament for treating one of the above diseases in a subject in need of the treatment. The invention further provides a method of making or manufacturing a medicament useful for treating one of these diseases comprising using a compound of Formula I, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, cerebrospinal fluid (CSF), or other body fluids or extracts thereof.

"Treat", "treating" or "treatment" with regard to a disease, refers to alleviating or abrogating the cause and/or the effects of the disease. In one embodiment, the terms "treat", "treatment" and "treating" refer to the reduction or amelioration of the progression, severity and/or duration of disease, or the amelioration of one or more symptoms of the disease (i.e., "managing" without "curing" the disease). In specific embodiments, the terms "treat"; "treatment" and "treating" refer to the amelioration of at least one measurable physical parameter of a disease. In other embodiments the terms "treat", "treatment" and "treating" refer to the inhibition of the progression of a disease, either physically by, e.g., stabilization of a discernible symptom or physiologically by, e.g., stabilization of a physiological parameter, or both.

The compounds and pharmaceutical compositions described herein can be used alone or in combination therapy for the treatment of a disease mediated, regulated or influenced by sGC, cGMP and/or NO.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

As used herein, the terms "in combination" (as in the phrase "in combination therapy") or "co-administration" can be used interchangeably to refer to the use of more than one therapy (e.g., one or more therapeutic agents). The use of the terms does not restrict the order in which therapies (e.g., therapeutic agents) are administered to a subject.

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When used in combination therapy with other agents, a "therapeutically effective amount" of the compounds and pharmaceutical compositions described herein and of the other agent or agents will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

In some embodiments, co-administration or combination therapy encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order.

When co-administration involves the separate administration of a first amount of a compound of Formula I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I and the second therapeutic agent can be administered in any order within about 24 hours of each other, within about 16 hours of each other, within about 8 hours of each other, within about 4 hours of each other, within about 1 hour of each other or within about 30 minutes of each other.

Examples of other therapeutic agents that may be combined with a compound of Formula I, or a pharmaceutically acceptable salt thereof, either administered separately or in the same pharmaceutical composition include, but are not limited to:

(1) Endothelium-derived releasing factor (EDRF) or NO gas.

(2) NO donors such as a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide (Dilatrate®-SR, Imdur®, Ismo®, Isordil®, Isordil®, Titradose®, Monoket®), 3-morpholinosydnonimine; linsidomine chlorohydrate ("SIN-1"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.

(3) Other substances that enhance cGMP concentrations such as protoporphyrin IX, arachidonic acid and phenyl hydrazine derivatives.

(4) Nitric Oxide Synthase substrates: for example, L-arginine, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.

(5) Compounds which enhance eNOS transcription.

(6) NO independent heme-independent sGC activators, including, but not limited to: BAY 58-2667 (described in patent publication DE19943635); HMR-1766 (ataciguat sodium, described in patent publication WO2000002851); S 3448 (2-(4-chloro-phenylsulfonylamino)-4,5-dimethoxy-N-(4-(thiomorpholine-4-sulfonyl)-phenyl)-benzamide (described in patent publications DE19830430 and WO2000002851); and HMR-1069 (Sanofi-Aventis).

(7) Heme-dependent, NO-independent sGC stimulators including, but not limited to: YC-1 (see patent publications EP667345 and DE19744026); riociguat (BAY 63-2521, Adempas®, described in DE19834044); neliciguat (BAY 60-4552, described in WO 2003095451); vericiguat (BAY 1021189); BAY 41-2272 (described in DE19834047 and DE19942809); BAY 41-8543 (described in DE19834044); etriciguat (described in WO 2003086407); CFM-1571 (described in patent publication WO2000027394); A-344905, its acrylamide analogue A-350619 and the aminopyrimidine analogue A-778935;

and other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507, 512, (WO2010099054) US20110218202 (WO2010065275), US20130012511 (WO2011119518), US20130072492 (WO2011149921), US20130210798 (WO2012058132) and Tetrahedron Letters (2003), 44(48): 8661-8663; and IW-1973 and IW1701.

(8) Compounds that inhibit the degradation of cGMP and/or cAMP, such as:

PDE1 inhibitors, PDE2 inhibitors, PDE-3 inhibitors such as, for example, amrinone, milrinone, enoximone, vesnarinone, pimobendan, and olprinone, PDE4 inhibitors, such as, for example, roflumilast, PDE5 inhibitors, such as, for example, sildenafil (Viagra®) and related agents such as avanafil, lodenafil, mirodenafil, sildenafil citrate (Revatio®), tadalafil (Cialis® or Adcirca®), vardenafil (Levitra®) and udenafil; alprostadil; dipyridamole and PF-00489791; PDE6 inhibitors, PDE9 inhibitors, such as, for example, PF-04447943, PDE10 inhibitors such as, for example, PF-02545920 (PF-10), and PDE11 inhibitors.

(9) Calcium channel blockers of the following types:

dihydropyridine calcium channel blockers such asamlodipine (Norvasc®), aranidipine (Sapresta®), azelnidipine (Calblock®), barnidipine (HypoCa®), benidipine (Coniel®), cilnidipine (Atelec®, Cinalong®, Siscard®), clevidipine (Cleviprex®), diltiazem, efonidipine (Landel®), felodipine (Plendil®), lacidipine (Motens®, Lacipil®), lercanidipine (Zanidip®), manidipine (Calslot®, Madipine®), nicardipine (Cardene®, Carden SR®), nifedipine (Procardia®, Adalat®), nilvadipine (Nivadil®), nimodipine (Nimotop®), nisoldipine (Baymycard®, Sular®, Syscor®), nitrendipine (Cardif®, Nitrepin®, Baylotensin®), pranidipine (Acalas®), and isradipine (Lomir®);

phenylalkylamine calcium channel blockers such as verapamil (Calan®, Isoptin®); and gallopamil (Procorum®, D600);

benzothiazepines such asdiltiazem (Cardizem®); and nonselective calcium channel inhibitors such as mibefradil, bepridil, fluspirilene, and fendiline.

(10) Endothelin receptor antagonists (ERAs) such as the dual ($ET_A$ and $ET_B$) endothelin receptor antagonist bosentan (Tracleer®), sitaxentan (Thelin®) or ambrisentan (Letairis®).

(11) Prostacyclin derivatives or analogues, such asprostacyclin (prostaglandin $I_2$), epoprostenol (synthetic prostacyclin, Flolan®), treprostinil (Remodulin®), iloprost (Ilomedin®), iloprost (Ventavis®); and oral and inhaled forms of Remodulin® under development.

(12) Antihyperlipidemics such as the following types:

bile acid sequestrants like cholestyramine, colestipol, colestilan, colesevelam or sevelamer; statins like atorvastatin, simvastatin, lovastatin, fluvastatin, pitavastatin, rosuvastatin and pravastatin;

cholesterol absorption inhibitors such as ezetimibe;

other lipid lowering agents such as icosapent ethyl ester, omega-3-acid ethyl esters, reducol; fibric acid derivatives such as clofibrate, bezafibrate, clinofibrate, gemfibrozil, ronifibrate, binifibrate, fenofibrate, ciprofibrate, choline fenofibrate;

nicotinic acid derivatives such as acipimox and niacin;

combinations of statins, niacin and intestinal cholesterol absorption-inhibiting supplements (ezetimibe and others) and fibrates; and antiplatelet therapies such as clopidogrel bisulfate.

(13) Anticoagulants, such as the following types:

coumarines (Vitamin K antagonists) such as warfarin (Coumadin®), cenocoumarol, phenprocoumon and phenindione;

heparin and derivatives such as low molecular weight heparin, fondaparinux and idraparinux; direct thrombin inhibitors such as argatroban, lepirudin, bivalirudin, dabigatran and ximelagatran (Exanta®); and tissue-plasminogen activators, used to dissolve clots and unblock arteries, such as alteplase.

(14) Antiplatelet drugs such as, for instance, topidogrel, ticlopidine, dipyridamoleand aspirin.

(15) ACE inhibitors, for example the following types:

sulfhydryl-containing agents such as captopril (Capoten®) and zofenopril; dicarboxylate-containing agents such as enalapril (Vasotec/Renitec®), ramipril (Altace®/Tritace®/Ramace®/Ramiwin®), quinapril (Accupril®), perindopril (Coversyl®/Aceon®), lisinopril (Lisodur®/Lopril®/Novatec®/Prinivil®/Zestril®) and benazepril (Lotensin®);

phosphonate-containing agents such as fosinopril;

naturally occurring ACE inhibitors such as casokinins and lactokinins, which are breakdown products of casein and whey that occur naturally after ingestion of milk products, especially cultured milk;

the lactotripeptides Val-Pro-Pro and Ile-Pro-Pro produced by the probiotic *Lactobacillus helveticus* or derived from casein also having ACE-inhibiting and antihypertensive functions;

other ACE inhibitors such as alacepril, delapril, cilazapril, imidapril, trandolapril, temocapril, moexipril and pirapril.

(16) Supplemental oxygen therapy.

(17) Beta blockers, such as the following types:

non-selective agents such as alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol and timolol;

$β_1$-Selective agents such as cebutolol, atenolol, betaxolol, bisoprolol, celiprolol, dobutamine hydrochloride, irsogladine maleate, carvedilol, talinolol, esmolol, metoprolol and nebivolol;

and $β_2$-Selective agents such as butaxamine.

(18) Antiarrhythmic agents such as the following types:

Type I (sodium channel blockers) such as quinidine, lidocaine, phenytoin, propafenone;

Type III (potassium channel blockers) such as amiodarone, dofetilide and sotalol; and Type V such as adenosine and digoxin.

(19) Diuretics such as thiazide diuretics, for example chlorothiazide, chlorthalidone and hydrochlorothiazide, bendroflumethiazide, cyclopenthiazide, methyclothiazide, polythiazide, quinethazone, xipamide, metolazone, indapamide, cicletanine; loop diuretics, such as furosemide and toresamide; potassium-sparing diuretics such as amiloride, spironolactone, canrenoate potassium, eplerenone and triamterene; combinations of these agents; other diuretics such as acetazolamid and carperitide.

(20) Direct-acting vasodilators such as hydralazine hydrochloride, diazoxide, sodium nitroprusside, cadralazine; other vasodilators such as isosorbide dinitrate and isosorbide 5-mononitrate.

(21) Exogenous vasodilators such as Adenocard® and alpha blockers.

(22) Alpha-1-adrenoceptor antagonists such as prazosin, indoramin, urapidil, bunazosin, terazosin and doxazosin; atrial natriuretic peptide (ANP), ethanol, histamine-inducers, tetrahydrocannabinol (THC) and papaverine.

(23) Bronchodilators of the following types:
- short acting $\beta_2$ agonists, such as albutamol or albuterol (Ventolin®) and terbutaline;
- long acting $\beta_2$ agonists (LABAs) such as salmeterol and formoterol;
- anticholinergics such as pratropium and tiotropium; and
- theophylline, a bronchodilator and phosphodiesterase inhibitor.

(24) Corticosteroids such as beclomethasone, methylprednisolone, betamethasone, prednisone, prednisolone, triamcinolone, dexamethasone, fluticasone, flunisolide, hydrocortisone, and corticosteroid analogs such as budesonide.

(25) Dietary supplements such as, for example omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.

(26) PGD2 receptor antagonists.

(27) Immunosuppressants such as cyclosporine (cyclosporine A, Sandimmune®, Neoral®), tacrolimus (FK-506, Prograf®), rapamycin (Sirolimus®, Rapamune®) and other FK-506 type immunosuppressants, mycophenolate, e.g., mycophenolate mofetil (CellCept®).

(28) Non-steroidal anti-asthmatics such as β2-agonists like terbutaline, metaproterenol, fenoterol, isoetharine, albuterol, salmeterol, bitolterol and pirbuterol; β2-agonist-corticosteroid combinations such as salmeterol-fluticasone (Advair®), formoterol-budesonide (Symbicort®), theophylline, cromolyn, cromolyn sodium, nedocromil, atropine, ipratropium, ipratropium bromide and leukotriene biosynthesis inhibitors (zileuton, BAY1005).

(29) Non-steroidal anti-inflammatory agents (NSAIDs) such as propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac; fenamic acid derivatives such as flufenamic acid, meclofenamic acid, mefenamic acid, niflumic acid and tolfenamic acid; biphenylcarboxylic acid derivatives such as diflunisal and flufenisal; oxicams such as isoxicam, piroxicam, sudoxicam and tenoxican; salicylates such as acetyl salicylic acid and sulfasalazine; and the pyrazolones such as apazone, bezpiperylon, feprazone, mofebutazone, oxyphenbutazone and phenylbutazone.

(30) Cyclooxygenase-2 (COX-2) inhibitors such as celecoxib (Celebrex®), rofecoxib (Vioxx®), valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine;

(31) Anti-diabetic agents such as insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®); α-glucosidase inhibitors such as acarbose, epalrestat, voglibose, miglitol; thiazolidinone compounds such as rosiglitazone (Avandia®), troglitazone (Rezulin®), ciglitazone, pioglitazone (Actos®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; dipeptidyl peptidase IV inhibitors such as sitagliptin, vildagliptin, saxagliptin, alogliptin and linagliptin.

(32) HDL cholesterol-increasing agents such as anacetrapib and dalcetrapib.

(33) Antiobesity drugs such as methamphetamine hydrochloride, amfepramone hydrochloride (Tenuate®), phentermine (Ionamin®), benzfetamine hydrochloride (Didrex®), phendimetrazine tartrate (Bontril®, Prelu-2 ®, Plegine®), mazindol (Sanorex®), orlistat (Xenical®), sibutramine hydrochloride monohydrate (Meridia®, Reductil®), rimonabant (Acomplia®), amfepramone, chromium picolinate; combination such as phentermine/topiramate, bupropion/naltrexone, sibutramine/metformin, bupropion SR/zonisamide SR, salmeterol, xinafoate/fluticasone propionate; lorcaserin hydrochloride, phentermine/topiramate, cetilistat, exenatide, liraglutide, metformin hydrochloride, sibutramine/metformin, bupropion SR/zonisamide SR, CORT-108297, canagliflozin, chromium picolinate, GSK-1521498, LY-377604, metreleptin, obinepitide, P-57AS3, PSN-821, salmeterol xinafoate/fluticasone propionate, sodium tungstate, somatropin (recombinant), tesamorelin, tesofensine, velneperit, zonisamide, beloranib hemioxalate, insulinotropin, resveratrol, sobetirome, tetrahydrocannabivarin and beta-lapachone.

(34) Angiotensin receptor blockers such as losartan, valsartan, candesartan, cilexetil, eprosaran, irbesartan, telmisartan, olmesartan, medoxomil, azilsartan and medoxomil.

(35) Renin inhibitors such as aliskiren hemifumirate.

(36) Centrally acting alpha-2-adrenoceptor agonists such as methyldopa, clonidine and guanfacine.

(37) Adrenergic neuron blockers such as guanethidine and guanadrel.

(38) Imidazoline I-1 receptor agonists such as rimenidine dihydrogen phosphate and moxonidine hydrochloride hydrate.

(39) Aldosterone antagonists such as spironolactone and eplerenone.

(40) Potassium channel activators such as pinacidil.

(41) Dopamine D1 agonists such as fenoldopam mesilate; other dopamine agonists such as ibopamine, dopexamine and docarpamine.

(42) 5-HT2 antagonists such as ketanserin.

(43) Vasopressin antagonists such as tolvaptan.

(44) Calcium channel sensitizers such as levosimendan or activators such as nicorandil.

(45) Adenylate cyclase activators such as colforsin dapropate hydrochloride.

(46) Positive inotropic agents such as digoxin and metildigoxin; metabolic cardiotonic agents such as ubidecarenone; brain natriuretic peptides such as nesiritide.

(47) Drugs used for the treatment of erectile dysfunction such as alprostadil, aviptadil, and phentolamine mesilate.
(48) Drugs used in the treatment of obesity, including but not limited to, methamphetamine hydrochloride (Desoxyn®), amfepramone hydrochloride (Tenuate®), phentermine (Ionamin®), benzfetamine hydrochloride (Didrex®), phendimetrazine hydrochloride (Bontril®, Prelu-2®, Plegine), mazindol (Sanorex®) and orlistat (Xenical®).
(49) Drugs used for the treatment of Alzheimer's disease and dementias such as the following types acetyl cholinesterase inhibitors including galantamine (Razadyne®), rivastigmine (Exelon®), donepezil (Aricept®) and tacrine (Cognex®);
NMDA receptor antagonists such as memantine (Namenda); and
oxidoreductase inhibitors such as idebenone.
(50) Psychiatric medications such as the following types:
ziprasidone (Geodon™), risperidone (Risperdal™), olanzapine (Zyprexa™), valproate;
dopamine D4 receptor antagonists such as clozapine;
dopamine D2 receptor antagonists such as nemonapride;
mixed dopamine D1/D2 receptor antagonists such as zuclopenthixol;
GABA A receptor modulators such as carbamazepine;
sodium channel inhibitors such as lamotrigine; and
monoamine oxidase inhibitors such as moclobemide and indeloxazine; and
primavanserin, and perospirone.
(51) Drugs used for the treatment of movement disorders or symptoms such as the following types:
catechol-O-methyl transferase inhibitors such as entacapone;
monoamine oxidase B inhibitors such as selegiline;
dopamine receptor modulators such as levodopa;
dopamine D3 receptor agonists such as pramipexole;
decarboxylase inhibitors such as carbidopa;
other dopamine receptor agonists such as pergolide, ropinirole, cabergoline;
ritigonide, istradefylline, talipexole; zonisamide and safinamide; and
synaptic vesicular amine transporter inhibitors such as tetrabenazine.
(52) Drugs used for the treatment of mood or affective disorders or OCD such as the following types:
tricyclic antidepressants such as amitriptyline (Elavil®), desipramine (Norpramin®), imipramine (Tofranil®), amoxapine (Asendin®), nortriptyline and clomipramine;
selective serotonin reuptake inhibitors (SSRIs) such as paroxetine (Paxil®), fluoxetine (Prozac®), sertraline (Zoloft®), and citralopram (Celexa®);
doxepin (Sinequan®), trazodone (Desyrel®) and agomelatine;
selective norepinephrine reuptake inhibitors (SNRIs) such as venlafaxine, reboxetine and atomoxetine; dopaminergic antidepressants such as bupropion and aminepine.
(53) Drugs for the enhancement of synaptic plasticity such as the following types: nicotinic receptor antagonists such as mecamylamine; and mixed 5-HT, dopamine and norepinephrine receptor agonists such as lurasidone.
(54) Drugs used for the treatment of ADHD such as amphetamine; 5-HT receptor modulators such as vortioxetine and alpha-2 adrenoceptor agonists such as clonidine.
(55) Neutral endopeptidase (NEP) inhibitors such as sacubitril, omapatrilat; and Methylene blue (MB).
(56) Nitric oxide synthase cofactors such as: tetrahydrobiopterin, dihydrobiopterin, and saropterin (Kuvan®)

Packaging and Kits

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, 2$^{nd}$ Ed., Washington, D.C.: American Chemical Society, 1997, herein incorporated in its entirety by reference.

Common abbreviations utilized in this application

| Abbreviation | Word or Phrase |
| --- | --- |
| Ac | Acetyl |
| Ac$_2$O | Acetic anhydride |
| ACN | Acetonitrile |
| AcOH | Acetic Acid |
| app. | Apparent |
| Boc | tert-butoxy carbonyl |
| br. | broad |
| Conc. | Concentration |
| DAST | Diethylaminosulfur trifluoride |
| DBU | 1,8-Diazabicyclo(5.4.0)undec-7-ene |

| Abbreviation | Word or Phrase |
|---|---|
| DCM | Dichloromethane |
| DMA | N,N-dimethylacetamide |
| DIEA | N,N-diisopropylethylamine |
| DMAP | 4-N,N-dimethylaminopyridine |
| DMF | N,N-dimethylformamide |
| DMSO | Dimethylsulfoxide |
| DMSO-d6 | Deuterated Dimethylsulfoxide |
| dppa | Diphenylphosphoryl azide |
| dppf | 1.1'-bis(diphenylphosphino)ferrocene |
| dba | dibenzylideneacetone |
| ES+ | Positive electron spray ionization |
| ES− | Negative electron spray ionization |
| Et | Ethyl |
| Et$_2$O | diethyl ether |
| EtOAc | ethyl acetate |
| EtOH | Ethanol |
| eq. | equation |
| equiv. | Equivalent |
| FA | Formic Acid |
| Gen. | general hour(s) |
| HEK | Human embryonic kidney |
| HPLC | high performance liquid chromatography |
| i-PA | Isopropyl alcohol |
| LC-MS | Liquid Chromatography-Mass Spectrometry |
| Me | Methyl |
| MeCN | Acetonitrile |
| MeOH | Methanol |
| MeOH-d4 | Deuterated methanol |
| min | Minutes |
| mL | Milliliter |
| MHz | Megahertz |
| MS | Mass Spectrometry |
| MTBE | Methyl tert-butyl ether |
| NMP | N-methylpyrrolidinone |
| NMR | Nuclear Magnetic Resonance |
| No. | Compound Number |
| Ph | Phenyl |
| ppm | parts per million |
| Pr | Propyl |
| Proc. | procedure |
| Rac | Racemic |
| RP-HPLC | reversed phase high performance liquid chromatography |
| RT | ambient temperature |
| temp. | Temperature |
| t-BuOH | tert-Butanol |
| TFA | Trifluoroacetic acid |
| THF | Tetrahydrofuran |
| TLC | thin layer chromatography |
| TMS-Cl | Trimethylsilylchloride |
| UV | Ultraviolet |

Example 1: Compounds Syntheses

Intermediate-1: 8-(2-Fluorobenzyl)imidazo[1,2-a]pyrazine-6-carbonitrile (Int-1)

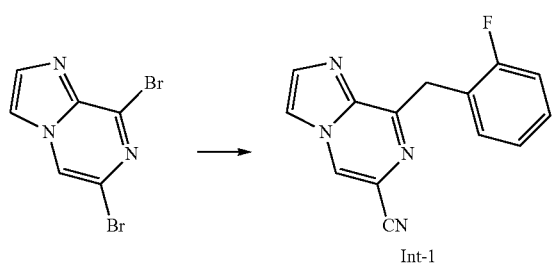 [SMILES: Brc1cn2ccnc2c(Br)n1 ; N#Cc1cn2ccnc2c(Cc2ccccc2F)n1]

This intermediate was synthesized according to a patent literature procedure (WO 2015/187470A1). $^1$H NMR (500 MHz, Methanol-d4) δ ppm 9.09 (s, 1H), 8.14 (s, 1H), 7.91 (s, 1H), 7.35 (t, 1H), 7.28 (d, 1H), 7.10 (m, 2H), 4.60 (s, 2H).

General Procedure A: Intermediate-2 (Int-2)

The title compound was synthesized in 2 steps:

Step 1: Synthesis of 8-(2-fluorobenzyl)imidazo[1,2-a]pyrazine-6-carboximidamide

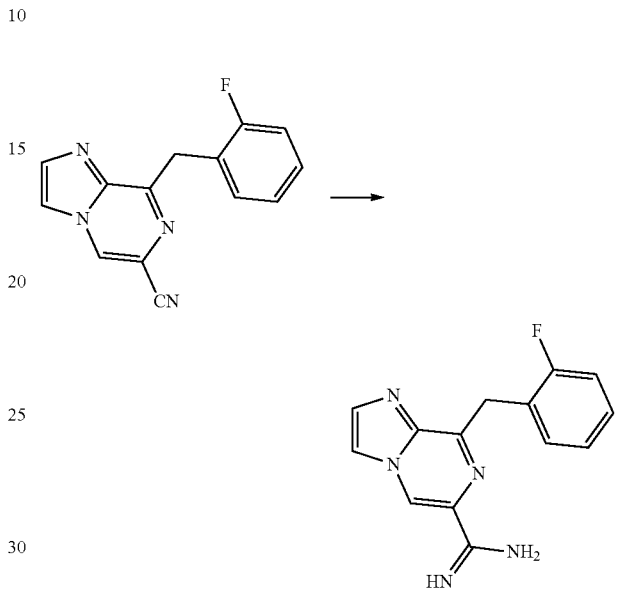

To a solution of 8-(2-fluorobenzyl)imidazo[1,2-a]pyrazine-6-carbonitrile (1 equiv., Intermediate-1) in methanol (12 ml or 4.8 ml was used depending on the batch) was added a solution of 0.5 M sodium methanolate (5 equiv.) (note: catalytic amount of sodium methanolate could also be used). After 1 h of stirring at room temperature, ammonia hydrochloride (10 equiv.) was added and the reaction was allowed to stir overnight. The reaction mixture was concentrated in vacuo, diluted with half-saturated NaHCO$_3$ (20 mL) and 1N NaOH (2 mL) and extracted with 2×20 mL of EtOAc. The combined organic phases were dried over sodium sulfate, filtered, and concentrated to afford the crude product as a brown solid. It was used in the next step without further purification.

Step 2: Synthesis of 5-fluoro-2-(8-(2-fluorobenzyl)imidazo[1,2-a]pyrazin-6-yl)pyrimidin-4-ol (Int-2)

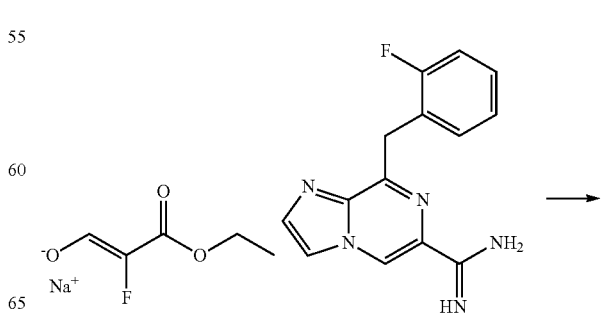

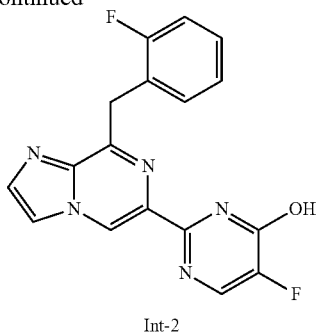

Int-2

To a solution of 8-(2-fluorobenzyl)imidazo[1,2-a]pyrazine-6-carboximidamide (1 equiv.) in ethanol (9 ml) was added sodium (Z)-3-ethoxy-2-fluoro-3-oxoprop-1-en-1-olate (3 equiv.). The reaction was heated in a sealed vial at 80° C. for 3 h. After cooling, the solvent was removed under vacuo.

The crude material was purified via reverse phase HPLC utilizing a 5-95% acetonitrile/water 0.1% TFA gradient to deliver the title compound (16 mg, 19% yield) as an off white solid. $^1$H NMR (500 MHz, Methanol-d4) δ ppm 9.48 (s, 1H), 8.28 (s, 1H), 8.09 (d, 1 H), 7.98 (s, 1H), 7.38 (s, 1H), 7.29 (d, 1H), 7.12 (m, 2H), 4.71 (s, 2H). When the compound was made in larger scale it was obtained as an off-white solid (57 mg, 33% yield). $^1$H NMR (500 MHz, DMSO-d$_6$) δ (ppm) 12.5 (br s, 1H), 9.48 (s, 1H), 8.31 (s, 1H), 8.18 (m, 1H), 7.88 (s, 1H), 7.47 (m, 1H), 7.27 (q, 1H), 7.19 (t, 1H), 7.09 (t, 1H), 4.59 (s, 2H).

Intermediate-3.

6-(4-chloro-5-fluoropyrimidin-2-yl)-8-(2-fluorobenzyl)imidazo[1,2-a]pyrazine(Int-3)

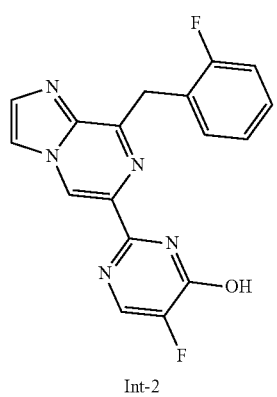

Int-2

→

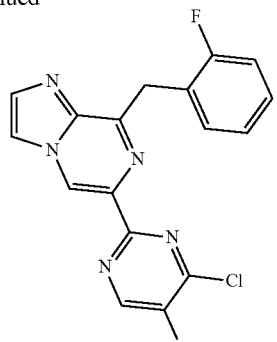

Int-3

A solution of intermediate Int-2 (1 equiv.) in POCl$_3$ (98 equiv.) was stirred overnight at room temperature. The solvent was removed under vacuo to deliver the crude intermediate Int-3 as a brown solid. It was used in the next step without further purification.

Compound I-2

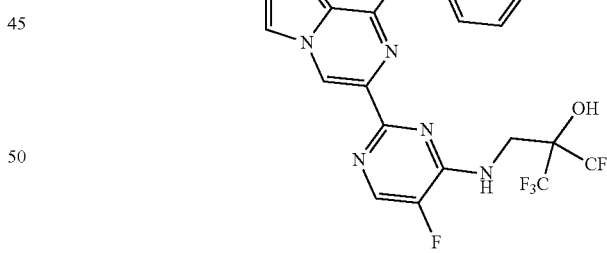

Compound I-2

A solution of intermediate Int-3 (1 equiv.) and 2-(aminomethyl)-1,1,1,3,3,3-hexafluoropropan-2-ol (3 equiv.) in DMSO (0.5 mL) in a microwave vial was heated by microwave at 120° C. for 2 h. After cooling, the solution was filtered and the crude material was purified via reverse phase HPLC utilizing a 30-60% acetonitrile/water 0.1% formic acid gradient to deliver Compound I-2 (10.2 mg, 42% yield) as a white solid. $^1$H NMR (500 MHz, DMSO-d6) δ ppm 9.43 (s, 1H), 9.22 (s, 1H), 8.46 (d, 1 H), 8.38 (br. s., 1H), 8.28 (s, 1H), 7.84 (s, 1H), 7.53 (t, 1H), 7.23 (br. s., 1H), 7.14 (t, 1H), 7.04 (t, 1H), 4.53 (s, 2H), 4.07 (d, 2H).

Compound I-1

The title compound was synthesized in 2 steps:

Step 1: Synthesis Of Dibenzyl (1,1,1,3,3,3-hexafluoro-2-(((5-fluoro-2-(8-(2-fluorobenzyl)imidazo[1,2-a]pyrazin-6-yl)pyrimidin-4-yl)amino)methyl)propan-2-yl) Phosphate (Compound I-4)

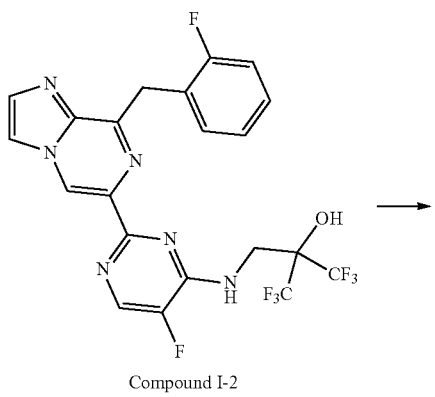

Compound I-2

Compound I-4

To a solution of 1,1,1,3,3,3-hexafluoro-2-(((5-fluoro-2-(8-(2-fluorobenzyl)imidazo[1,2-a]pyrazin-6-yl)pyrimidin-4-yl)amino)methyl)propan-2-ol (Compound I-2) 0.48 g, 1 equiv.) in THF (9 ml) at 0° C. was added LiHMDS 1M in THF (1.2 ml, 1.3 equiv.) dropwise over 5 minutes. The resulting yellow solution was stirred at 0° C. for 20 minutes. In a separate flask was prepared a solution of tetrabenzyl diphosphate (0.69 g, 1.4 equiv.) in THF (5 ml) and cooled to 0° C. The alkoxide solution was added dropwise to the pyrophosphate solution over 15 min and the reaction allowed to warm to rt over 4 h. It was then stirred at rt for 5 d. The reaction was diluted with ethyl acetate (20 ml) and washed with water (10 ml). The organic layer was dried over sodium sulfate, filtered, and concentrated to give crude product as a yellow gum. It was taken to the next step without further purification.

Step 2: Synthesis of Compound I-1

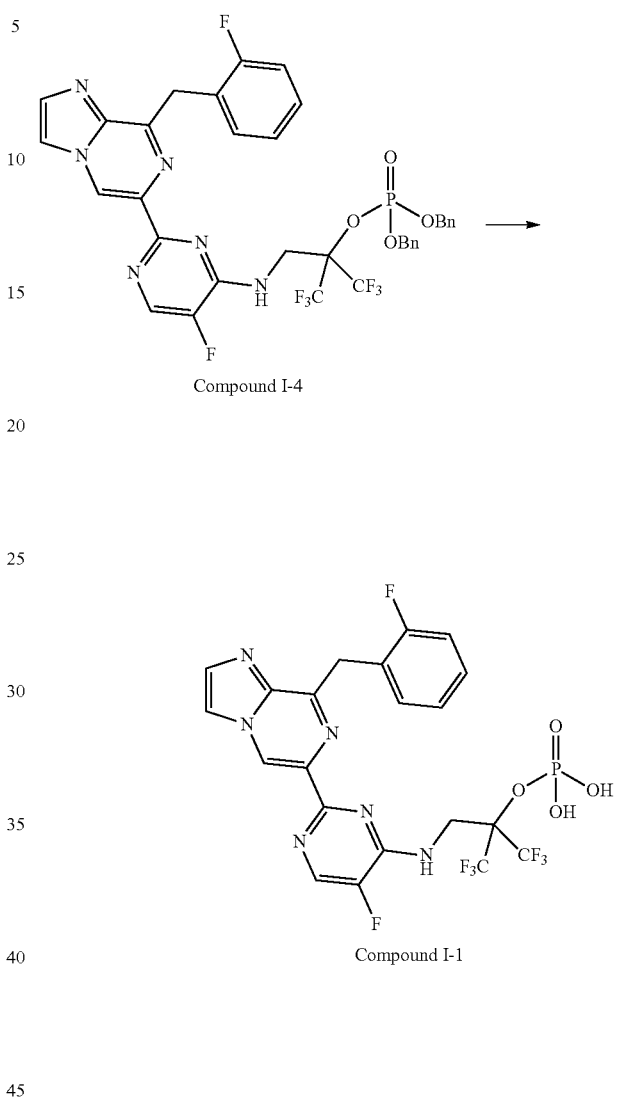

Compound I-4

Compound I-1

To a solution of crude dibenzyl (1,1,1,3,3,3-hexafluoro-2-(((5-fluoro-2-(8-(2-fluorobenzyl)imidazo[1,2-a]pyrazin-6-yl)pyrimidin-4-yl)amino)methyl)propan-2-yl) phosphate (Compound I-4) in ethyl acetate (10 ml) and THF (10 ml) was added 5% palladium on carbon (1 equiv.). The reaction was stirred under a balloon of hydrogen overnight at rt. The mixture was filtered through a pad of celite and washed with methanol (10 ml). The eluant was concentrated to dryness to give a crude yellow solid. The crude material was purified via reverse phase HPLC utilizing a 10-50% acetonitrile water 0.1% TFA gradient to deliver Compound I-1 (18 mg, 13% yield) as a white solid. $^1$H NMR (500 MHz, Deuterium Oxide) δ ppm 8.81 9.10 (s, 1H), 8.12 (d, 1H), 8.05 (s, 1H), 7.78 (s, 1H), 7.31 (m, 2H), 7.14 (m, 2H), 4.67 (s, 2H), 4.62 (s, 2H).

Intermediate-4 (Int-4)

This intermediate was prepared in four steps:

Step 1: Cyanation Of Intermediate (15) to Provide 2-(bromomethyl)-3,3,3-trifluoro-2-((trimethylsilyl)oxy)propanenitrile (16)

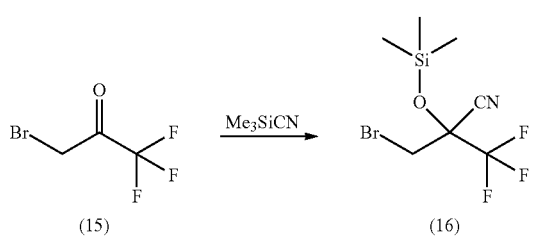

Trimethylsilanecarbonitrile (153 g, 1.54 mol, 0.97 equiv) and triethylamine (4.44 mL, 3.22 g, 0.032 mol, 0.02 equiv) were charged to a suitable reaction vessel equipped with a mechanical stirrer and a digital thermometer. The mixture was cooled to 5° C. 3-Bromo-1,1,1-trifluoropropan-2-one ((15), 304 g, 1.59 mol, 1.0 equiv) was charged via an addition funnel over 35 min, while maintaining the reaction temperature between 10 to 20° C.

The mixture was stirred at 20 to 30° C., over 3 h, after the addition to furnish intermediate (16) as a dense oil which was used directly in the next step. $^1$H-NMR (500 MHz, CDCl$_3$) δ ppm 3.68 (d, J=11.14 Hz, 1H); 3.57 (d, J=11.14 Hz, 1H), 0.34-0.37 (m, 9H).

Step 2: Conversion Of Nitrile (16) To Amide To Provide 2-(bromomethyl)-3,3,3-trifluoro-2-hydroxypropanamide (17)

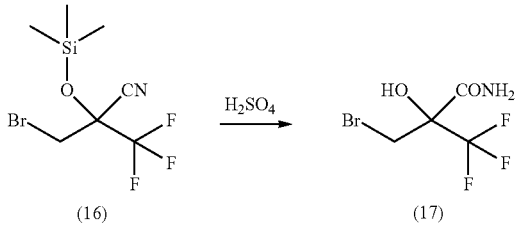

Concentrated sulfuric acid (339 mL, 6.37 mol, 4.0 equiv) was stirred in a suitable reaction vessel equipped with a mechanical stirrer, digital thermometer and an addition funnel. The sulfuric acid was heated to 45° C. The above intermediate (16) was added via an addition funnel over 50 min, while keeping the temperature below 75° C. The reaction mixture was stirred at 75° C. for 2 h and then allowed to cool to room temperature. $^1$H-NMR indicated reaction complete. The reaction mixture was cooled to −15° C. and diluted with ethyl acetate (1824 mL) via an addition funnel over 45 min (very exothermic), while keeping the temperature between −15 to 5° C. Water (1520 mL) was added slowly via an addition funnel for 1 h 20 min. (very exothermic) between −10 to 0° C. The layers were separated and the organic layer was washed with 15% aqueous sodium chloride solution (1520 mL), 25% aqueous sodium carbonate solution (911 mL) followed by 15% aqueous sodium chloride solution (911 mL). The organic layer was filtered and concentrated under reduced pressure to get 348 g of intermediate (17) as light yellow oil. This oil was dissolved in methanol (1200 mL) and concentrated to furnish 380 g of intermediate (17). (296 g adjusted weight, 79% yield). $^1$H-NMR (500 MHz, CDCl$_3$) δ 6.61-6.94 (m, 1H); 5.92-6.26 (m, 1H); 3.93-4.00 (m, 1H); 3.68 (d, J=11.14 Hz, 1H).

Step 3: N-Alkylation Of Compound (17) To Provide Of 2-(aminomethyl)-3,3,3-trifluoro-2-hydroxypropanamide (14)

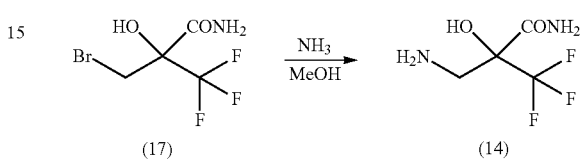

A 7 N solution of ammonia in methanol (600 mL, 4.28 mol, 10 equiv) was charged to a suitable reaction vessel equipped with a mechanical stirrer and a digital thermometer. The solution was cooled to 0 to 5° C. Then the intermediate (17) (102 g, 0.432 mol, 1 equiv) was added via an addition funnel over 30 min at 0 to 5° C. The reaction mixture was warmed to 20 to 25° C., over 1 hour, and held for 72 hours. The reaction was complete by HPLC. The reaction mixture was cooled to 0 to 5° C. and sodium methoxide (78 mL, 5.4 M, 0.421 mol, 0.97 equiv) was added over 2 min. The reaction mixture was then concentrated under reduced pressure to a volume of 300 mL. 2 L of ethyl acetate was added and concentration was continued under reduced pressure to a volume to 700 mL to get a slurry. 700 mL of ethyl acetate was added to the slurry to make the final volume to 1400 mL. 102 mL of water was added and stirred for 2 min to get a biphasic solution. The layers were separated. The ethyl acetate layer was concentrated under reduced pressure to a volume of 600 mL. Then the ethyl acetate layer was heated to >60° C. and heptane (600 mL) was added slowly between 55 to 60° C. The mixture was cooled to 15 to 20° C. to give a slurry. The slurry was stirred at 15 to 20° C. for 2 h and filtered. The solids were dried under vacuum at 25° C. for 16 h to furnish amine (14) as white solid (48 g, 64% yield). $^1$H-NMR (500 MHz, MeOH-d$_4$) δ ppm 2.94 (d, J=13.73 Hz, 1H); 3.24 (d, J=13.58 Hz, 1H).

Step 4: Chiral Resolution Of Amine (14) As (R)-2,2-dimethyl-5-(trifluoromethyl)oxazolidine-5-carboxamide (R)-2-hydroxysuccinate (Intermediate-4, Int-4)

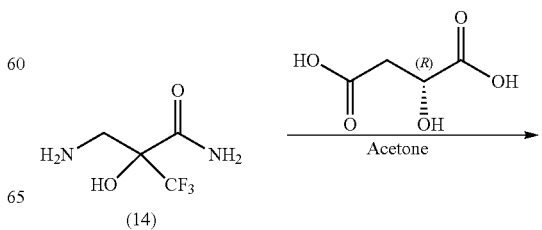

-continued

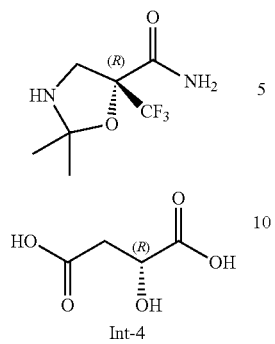

Int-4

Amine (14) (105 g, 0.608 mol, 1.0 equiv.), (D)-Malic acid (82 g, 0.608 mol, 1.0 equiv.) and acetone (1571 mL) were charged to a suitable reaction vessel equipped with a mechanical stirrer and a digital thermometer. The reaction mixture was stirred at 20 to 25° C. for 16 h. The resulting slurry was filtered, and the wet cake was washed with acetone (300 mL). The wet cake was charged back to the reaction vessel, and acetone (625 mL) was charged. The slurry was heated to 53° C. and held for 6 h. The slurry was cooled to 20 to 25° C. and held for 16 h. The slurry was filtered, and the wet cake was washed with acetone (200 mL). The wet cake was dried under vacuum at 40° C. for 4 h to furnish 82.4 g of intermediate Int-4 as a white solid (82.4 g, 39% yield, 97% ee). $^1$H-NMR (500 MHz, D$_2$O) δ ppm 4.33 (br, s, 1H); 3.61 (br, d, J=13.58 Hz, 1H); 3.40-3.47 (m, 1H); 2.76 (br, d, J=15.87 Hz, 1H); 2.53-2.63 (m, 1H); 2.16 (br, s, 4H).

Compound I-3

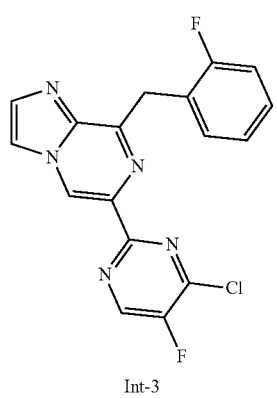

Int-3

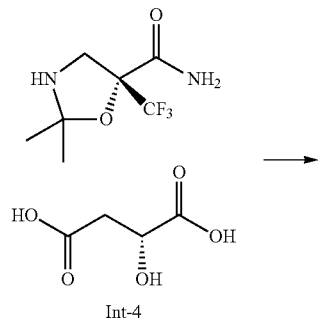

Int-4

-continued

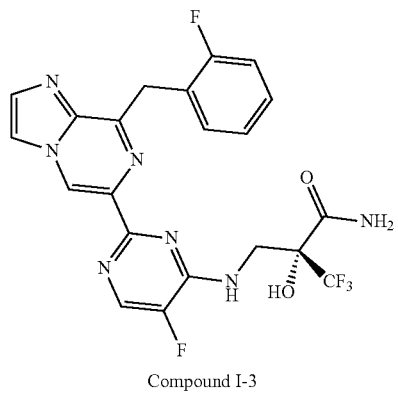

Compound I-3

A solution of intermediates Int-3 and Int-4 and N,N-Diisopropylethylamine (3 equiv.) in DMSO (0.4 mL) and water (0.04 mL) was heated by microwave at 120° C. in a microwave vial for 2 h. After cooling, the mixture was filtered and the crude material was purified via reverse phase HPLC utilizing a 30-60% acetonitrile/water 0.1% formic acid gradient to deliver Compound I-3 (13.1 mg, 32% yield) as a white solid. $^1$H NMR (500 MHz, DMSO-d6) δ ppm 9.43 (s, 1H), 8.39 (d, 1H), 8.32 (br. s., 1 H), 8.27 (s, 1H), 8.16 (d, 1 H), 7.83 (s, 1H), 7.78 (br. s., 1H), 7.60 (br. s., 1H), 7.52 (t, 1H), 7.24 (d, 1H), 7.15 (d, 1H), 7.06 (t, 1 H), 4.57 (s, 2H), 4.00 (d, 2H).

Compound of General Formula B1

Analogously to the synthesis exemplified above for Compounds I-1, I-2, I-3 and I-4, compounds with the core of Formula B1 below can be synthesized by the following scheme.

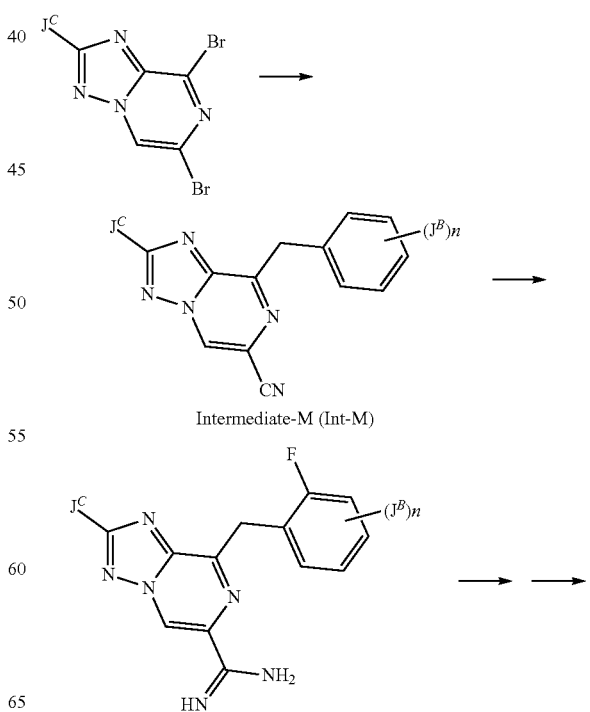

Intermediate-M (Int-M)

-continued

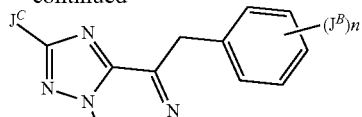

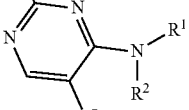

Formula B1

Compounds of the general formula of intermediate Int-M can be prepared according the protocols described in WO2016081668. Intermediate-Int-M can then be further elaborated by protocols analogous to those described above to access compounds I-1 to I-4.

Intermediate-5

8-(2,5-Difluorobenzyl)imidazo[1,2-a]pyrazine-6-carbonitrile (Int-5)

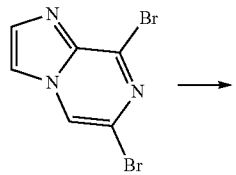

Intermediate-5a

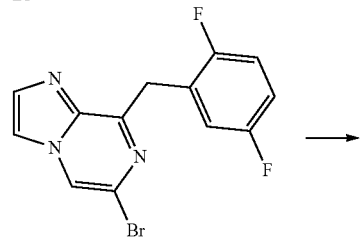

Int-5

Nitrile intermediate Int-5 was prepared from the starting bromide, 6,8-dibromoimidazo[1,2-a]pyrazine, using 2,5-difluorobenzyl bromide according to the patent literature procedure (WO 2015/187470A1) described for the synthesis of Int-1. MS ES+ m/z=271.2 [M+H]+.

Intermediate 6

6-(4-chloro-5-fluoropyrimidin-2-yl)-8-(2,5-difluorobenzyl)imidazo[1,2-a]pyrazine (Int-6)

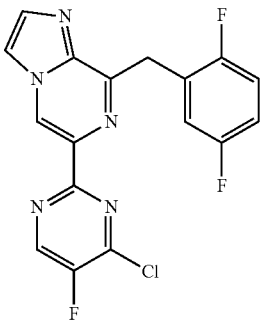

Int-6

Intermediate Int-6 was prepared from intermediate Int-5 according to the general procedure described for the synthesis of intermediate Int-3 from Int-1. MS ES+ m/z 376.3 [M+H]+.

Compound I-5

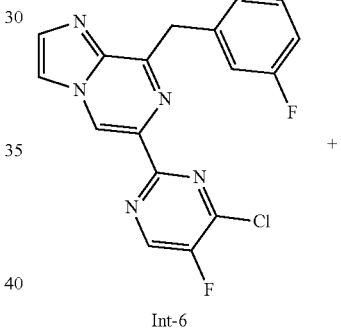

Int-6

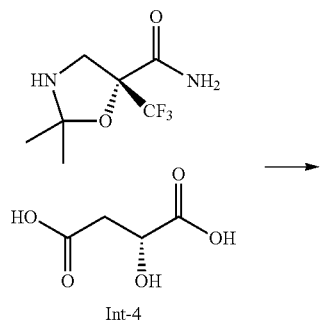

Int-4

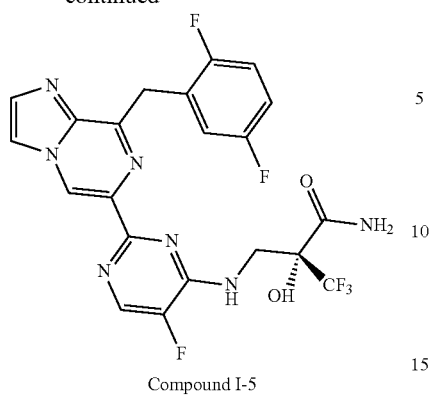

Compound I-5

A solution of intermediates Int-6 (1 equiv.), Int-4 (3 equiv.) and triethylamine (5 equiv) in dioxane/water 3:1, (1.3 mL) was heated at 90° C. for 18 h. After cooling to room temperature, the reaction mixture was reduced to half its volume, diluted with 1N aqueous HCl solution and ethyl acetate. The layers were separated and the organic layer was washed successively with water then saturated aqueous sodium chloride solution, dried (sodium sulfate), and concentrated in vacuo to afford a crude solid. The crude material was purified by reverse phase HPLC using a gradient of 30 to 60% acetonitrile in water (modified by 0.1% formic acid) to provide Compound I-5 (20.0 mg, 29% yield) as an off-white solid. $^1$H NMR (500 MHz, CD$_3$OD) δ (ppm): 9.40 (s, 1H), 8.22-8.25 (m, 1H), 8.18 (s, 1H), 7.83 (s, 1H), 7.15-7.21 (m, 1H), 7.06-7.10 (m, 1H), 6.91-6.98 (m, 1H), 4.65 (s, 2H), 4.26 (d, 1H), 4.05 (d, 1H). MS ES$^+$ m/z 512.2 [M+H]$^+$.

Intermediate-7

8-(2-Fluorobenzyl)-[1,2,4]triazolo[1,5-a]pyrazine-6-carbonitrile (Int-7)

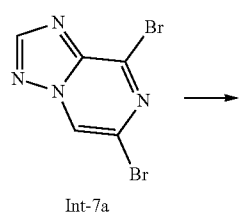

Int-7a

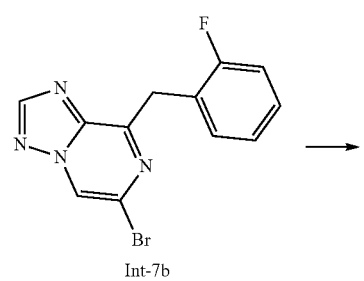

Int-7b

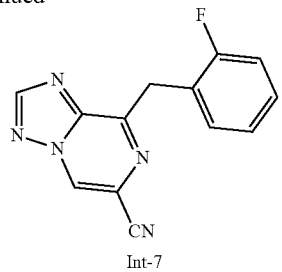

Int-7

A solution of (2-fluorobenzyl)zinc(II) chloride (18.0 ml, 0.5 M in THF, 9.00 mmol) was added to a mixture of PdCl$_2$(PPh$_3$)$_2$ (0.253 g, 0.360 mmol) and commercially available intermediate Int-7a (2.00 g, 7.20 mmol). The reaction was purged with nitrogen, sealed and heated to 50° C. for 1 h. The reaction mixture was cooled to room temperature and directly purified by silica gel chromatography utilizing a gradient of 0-70% ethyl acetate in hexanes to afford intermediate Int-7b (1.49 g, 61%). $^1$H NMR: (500 MHz, DMSO-d6), δ (ppm): 9.46 (s, 1H), 8.74 (s, 1H), 7.39-7.42 (m, 1H), 7.30-7.34 (m, 1H), 7.14-7.21 (m, 2H), 4.56 (s, 2H). MS ES$^+$ m/z=307.1 [M]$^+$, 309.0 [M+2]$^+$, A stirred mixture of Int-7b (1.49 g, 4.85 mmol), zinc (II) cyanide (0.684 g, 5.82 mmol), DPPF (0.538 g, 0.970 mmol), Pd$_2$(dba)$_3$ (0.533 g, 0.582 mmol), and zinc (0.162 g, 2.47 mmol), in DMA (8 mL) was heated at 120° C. for 2 h under a nitrogen atmosphere. Upon completion, the mixture was cooled to room temperature, diluted with a mixture of ethyl acetate:dichloromethane:methanol (2:1:1, 100 mL), filtered through a pad of celite, and concentrated. The residue was purified by silica gel chromatography utilizing a gradient of 0-85% ethyl acetate in hexanes to afford intermediate Int-7 (869 mg, 71%). $^1$H NMR: (500 MHz, MeOH-d4), δ (ppm): 9.52 (s, 1H), 8.72 (s, 1H), 7.39-7.42 (m, 1H), 7.28-7.32 (m, 1 H), 7.08-7.15 (m, 2H), 4.65 (s, 2H). MS ES$^+$ m/z 254.1 [M+H]$^+$, Intermediate 10

6-(4-chloro-5-fluoropyrimidin-2-yl)-8-(2-fluorobenzyl)-[1,2,4]triazolo[1,5-a]pyrazine (Int-10)

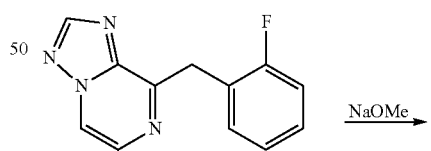

Int-7

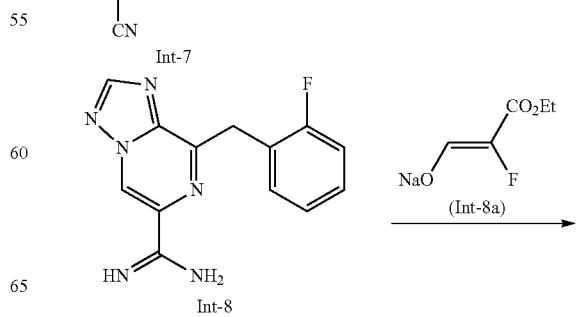

Int-8

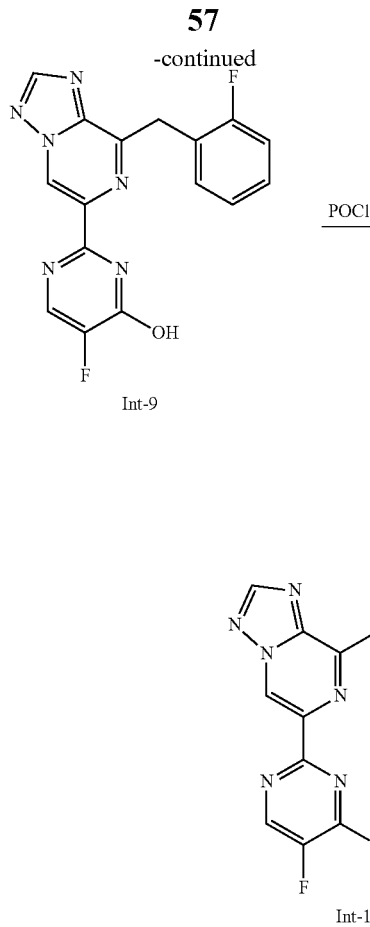

Int-9

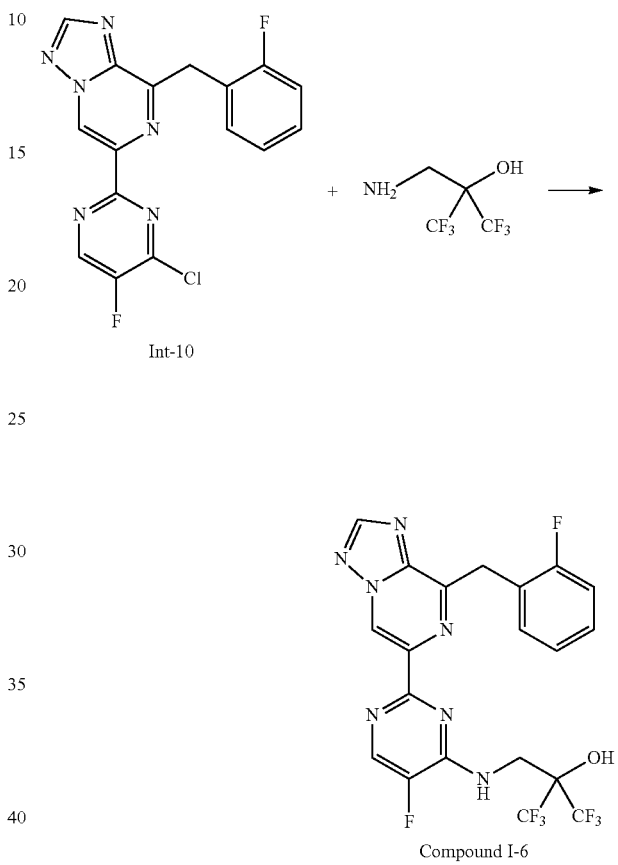

Int-10

To a stirred room temperature solution of intermediate Int-7 (1.64 g, 6.48 mmol) in MeOH (33 mL) was added a solution of sodium methoxide (4.44 ml, 25% in MeOH, 19.4 mmol). After 1 h, the formation of the imidate ester was confirmed by LC-MS. Solid NH$_4$Cl (1.73 g, 32.4 mmol) was added and the mixture was stirred while monitoring reaction progress by LC-MS analysis. Upon completion, the resultant precipitate was filtered and dried under vacuum to afford intermediate Int-8 (1.63 g, 93%). MS ES$^+$ m/z 271.1 [M+H]$^+$ To a stirred mixture of intermediate Int-8 (1.63 g, 6.03 mmol) in absolute EtOH (27 ml) at RT was added intermediate Int-8a (2.82 g, 18.1 mmol). The mixture was heated at 80° C. for 30 min and the reaction progress was monitored by LC-MS analysis. Upon completion, an aqueous solution of HCl (18.1 ml, 1M) was added and the resulting mixture was stirred for 30 mins at room temperature leading to the formation of a precipitate. The solid was filtered and dried in vacuo. A second crop was recovered from the filtrate upon standing for 30 min. The combined solids were dried under high vacuum to yield intermediate Int-9 (2.01 g, 98%). MS ES$^+$ m/z 341.0 [M+H]$^+$.

A stirred mixture of POCl$_3$ (1.96 ml, 21.0 mmol) and intermediate Int-9 (358 mg, 1.05 mmol) was heated at 80° C. for 30 min while the reaction progress was monitored by LC-MS analysis. Upon completion, the POCl$_3$ was evaporated in vacuo and the residue was partitioned between saturated aqueous sodium bicarbonate solution (20 mL) and dichloromethane (40 mL). The aqueous layer was extracted with dichloromethane (2×40 mL), and the combined organic layers were dried (MgSO$_4$), filtered and concentrated to provide a crude residue. The crude product was purified by silica gel chromatography utilizing a gradient of 0-50% ethyl acetate in hexanes to afford intermediate Int-10 (200 mg, 53.0%) as a solid. $^1$H NMR (500 MHz, DMSO-d6) δ ppm 9.65 (s, 1H), 9.14 (s, 1H), 8.82 (s, 1H), 7.40 (m, 1H), 7.34-7.26 (m, 1H), 7.23-7.15 (m, 1H), 7.15-7.08 (m, 1H), 4.66 (s, 2H). MS ES$^+$ m/z 359.0 [M+H]$^+$.

Compound I-6

A solution of intermediate Int-10 (1 equiv.), 2-(aminomethyl)-1,1,1,3,3,3-hexafluoropropan-2-ol (3 equiv.) and N-ethyl-N-isopropylpropan-2-amine in DMSO (0.8 mL) was heated at 90° C. for 1 h, then 70° C. for an additional 12 hours. After cooling to room temperature, the reaction mixture was diluted with 1N aqueous HCl to pH=3, leading to the formation of an orange precipitate which was filtered and dried. Purification of the crude material was achieved by silica gel chromatography utilizing a gradient of 0 to 20% of a 7:1 acetonitrile/methanol solution in dichloromethane over 25 minutes, followed by reverse phase HPLC utilizing a gradient of 20 to 70% acetonitrile in water (modified with 0.1% trifluoroacetic acid) over 25 minutes to afford Compound I-6 (12.2 mg, 17% yield) as a light yellow solid. $^1$H NMR: (500 MHz, DMSO-d$_6$), δ (ppm): 9.57 (s, 1H), 8.83 (s, 1H), 8.80 (s, 1H), 8.49 (d, 1H), 8.31 (m, 1H), 7.48-7.51 (t, 1H), 7.26-7.30 (m, 1H), 7.14-7.18 (t, 1H), 7.07-7.10 (t, 1H), 4.60 (s, 2H), 4.16 (d, 2H). MS ES$^+$ m/z=520.3.

Intermediate 11

3-chloro-6-(4-chloro-5-fluoropyrimidin-2-yl)-8-(2-fluorobenzyl)imidazo[1,2-a]pyrazine (Int-11)

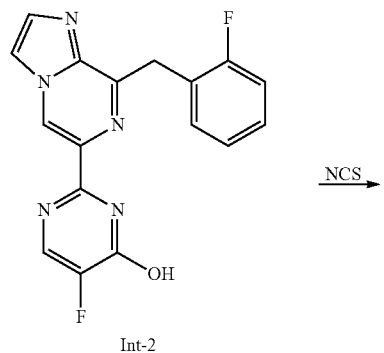

Int-2

NCS →

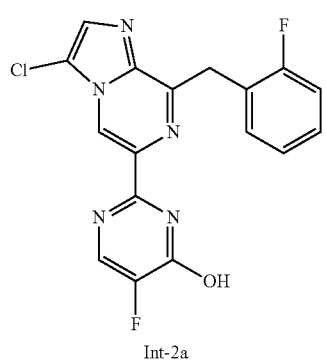

Int-2a

POCl₃ →

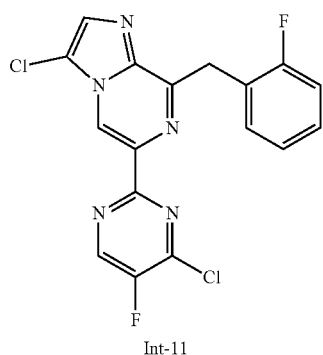

Int-11

To a solution of intermediate Int-2 (103 mg, 0.304 mmol) in MeOH (5 mL) at 0° C. was added N-chlorosuccinimide (NCS) (44.6 mg, 0.344 mmol). After 30 min, the reaction was warmed to ambient temperature for 17 h and then to 50° C. for 2.5 h. The reaction mixture was concentrated and the resultant residue was purified by silica gel chromatography utilizing a 0-20% gradient of acetonitrile/methanol (7:1) in dichloromethane to yield intermediate Int-2a (99.6 mg, 85%). MS ES⁺ m/z 374.2 [M+H]⁺.

A mixture of intermediate Int-2a (47.9 mg, 0.128 mmol) in POCl₃ (0.836 ml, 8.97 mmol) was stirred for 2.5 h at 60° C., after which LCMS analysis indicated that the reaction was complete. The mixture was concentrated to dryness. The residual amount of POCl₃ was removed by chasing with toluene (2×1 mL) and drying further in vacuo. The resultant crude of Int-11 was used without purification. MS ES⁺ m/z 392.2 [M+H]⁺.

Compound I-7

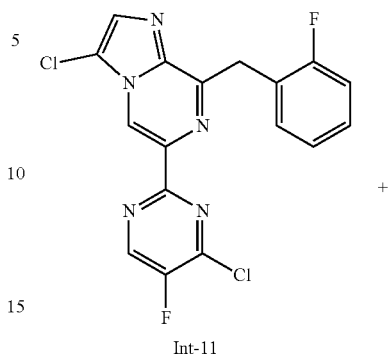

Int-11

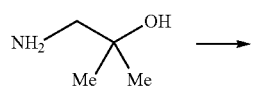

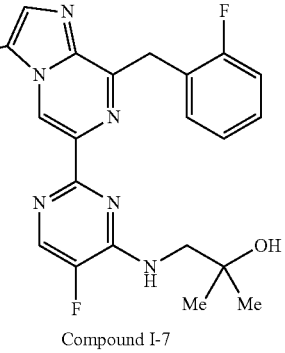

Compound I-7

A suspension of intermediate Int-11 (1.0 equiv.), N-ethyl-N-isopropylpropan-2-amine (6.0 equiv.), and 1-amino-2-methylpropan-2-ol (1.8 equiv.) in DMSO (1.0 mL) was heated to 90° C. for 16 h. After cooling to room temperature, the reaction mixture was purified directly by silica gel chromatography utilizing a gradient of 7:1 acetonitrile/methanol in dichloromethane over 75 minutes to afford Compound I-7 (19.4 mg, 35% yield) as an off-white solid. ¹H NMR: (500 MHz, DMSO-d₆), δ (ppm): 8.90 (s, 1 H), 8.28 (d, 1H), 8.00 (s, 1H), 7.55-7.57 (m, 1H), 7.44-7.47 (m, 1H), 7.25-7.30 (m, 1H), 7.15-7.19 (m, 1H), 7.09-7.12 (m, 1H), 4.73 (s, 1H), 4.58 (s, 2H), 3.49 (d, 2H), 1.15 (s, 6 H). MS ES⁺ m/z=445.2.

Intermediate 13

6-(4,5-dichloropyrimidin-2-yl)-8-(2-fluorobenzyl)imidazo[1,2-a]pyrazine (Int-13)

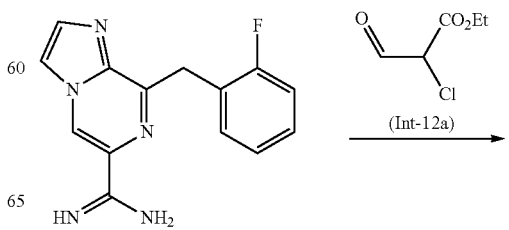

(Int-12a)

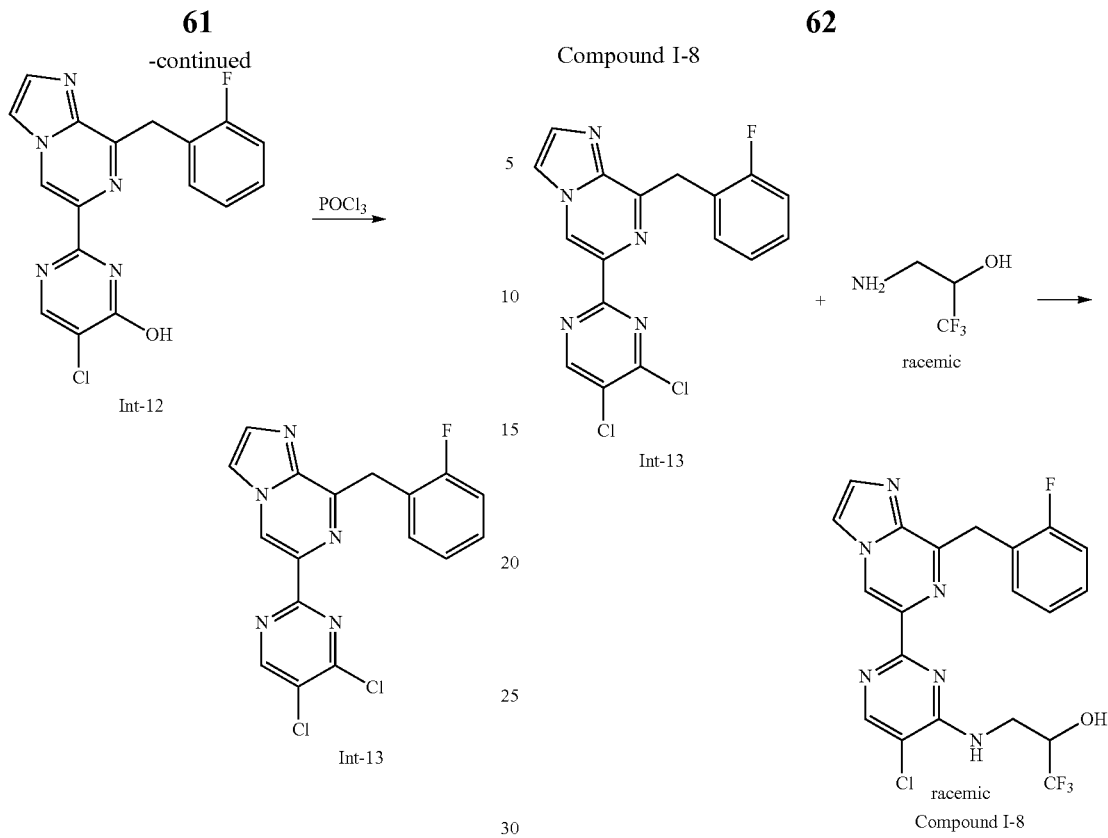

To a stirred mixture of 8-(2-fluorobenzyl)imidazo[1,2-a]pyrazine-6-carboximidamide (5.00 g, 18.6 mmol) and Int-12a (4.19 g, 27.9 mmol) in anhydrous MeOH (100 mL) at room temperature was added a solution of NaOMe (8.49 mL, 25 wt % in MeOH, 37.1 mmol) in anhydrous MeOH (24 mL) over 5 min. The resultant solution was heated at reflux. After 2 h, reaction was incomplete; thus, more Int-12a (900 mg, 5.98 mmol) was added. After heating for an additional 2 h, the mixture was cooled to RT and stirred overnight. The mixture was concentrated and the resultant residue was stirred in H$_2$O (100 mL). The pH was adjusted to 3 with aqueous HCl (2 mL, 6M), the mixture was stirred 30 min, and filtered. The solids were washed with H$_2$O (2×30 mL) and dried in high vacuum to provide intermediate Int-12 (5.20 g, 79%). MS ES$^+$ m/z 356.2 [M+H]$^+$ A stirred mixture of Int-12 (5.20 g, 14.6 mmol) and DMAP (179 mg, 1.46 mmol) in POCl$_3$ (27.0 mL, 292 mmol) was heated at 90° C. for 3 h. The mixture was concentrated and the residual POCl$_3$ was removed azeotropically with toluene (100 mL). The residue was re-dissolved in dichloromethane (200 mL), cooled in an ice bath and neutralized with a 10% aqueous solution of NaHCO$_3$ (150 mL). The mixture was diluted with DCM (100 mL) and phases were separated. The organic layer was washed with H$_2$O (50 mL) and saturated aqueous solution of NaHCO$_3$ (2×50 mL), dried over Na$_2$SO$_4$, filtered and concentrated. The residue was purified by silica gel chromatography utilizing a gradient of 20-80% ethyl acetate in hexanes to afford intermediate Int-13 (2.50 g). $^1$H NMR (500 MHz, CDCl$_3$) δ (ppm) 9.18 (s, 1H), 8.77 (s, 1H), 7.76 (d, 1H), 7.69-7.73 (m, 1H), 7.30 (m, 1H), 7.08-7.12 (m, 1H), 6.89-7.01 (m, 2H), 4.71 (s, 2H). MS ES$^+$ m/z 374.1 [M+H]$^+$ To a solution of intermediate Int-13 (1.0 equiv.) and racemic-3-amino-1,1,1-trifluoropropan-2-ol (3.0 equiv.) in 3:1 dioxane/water (1.3 mL) was added triethylamine (5.0 equiv.). The reaction mixture was stirred at 90° C. for 18 h. After cooling to room temperature, the reaction mixture was reduced to half its volume, diluted with 1N aqueous HCl solution and ethyl acetate. The layers were separated and the organic layer was washed successively with water then saturated aqueous sodium chloride solution, dried (sodium sulfate), and concentrated in vacuo to afford a crude solid. The crude material was purified by reverse phase HPLC using a gradient of 30 to 60% acetonitrile in water (modified by 0.1% formic acid) to provide racemic Compound I-8 (34.5 mg, 55% yield) as a pale yellow solid. $^1$H NMR (500 MHz, CD$_3$OD) δ (ppm): 9.35 (s, 1H), 8.32 (s, 1H), 8.12 (s, 1H), 7.80 (s, 1H), 7.25-7.30 (m, 1H), 7.17-7.24 (m, 1H), 6.99-7.02 (m, 1H), 7.02-7.07 (m, 1H), 4.66 (s, 2H), 4.33-4.41 (m, 1H), 4.03 (dd, 1H), 3.76 (dd, 1H). MS ES$^+$ m/z=467.2

Intermediate 15

2-(8-(2-fluorobenzyl)imidazo[1,2-a]pyrazin-6-yl)pyrimidin-4-ol (Int 15)

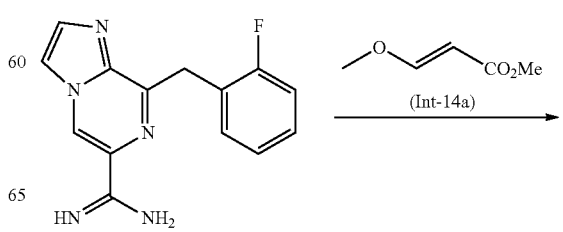

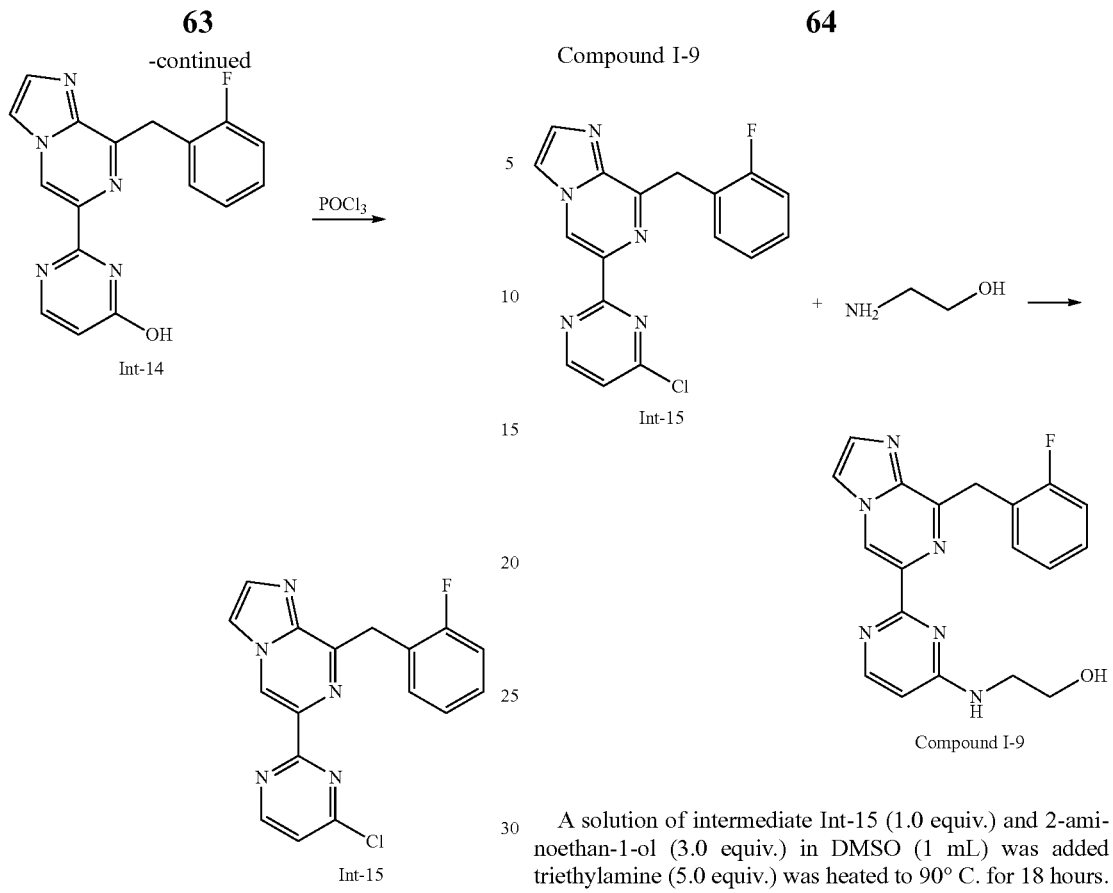

Int-14

Int-15

A solution of 8-(2-fluorobenzyl)imidazo[1,2-a]pyrazine-6-carboximidamide (1.00 g, 3.71 mmol), intermediate Int-14a (1.21 ml, 11.1 mmol) and N-ethyl-N-isopropylpropan-2-amine (1.95 mL, 11.1 mmol) in ethanol (14.9 mL) was stirred at 80° C. for 12 hours. The reaction mixture was cooled to room temperature to which ammonium chloride (0.6 g) was added and the resulting mixture was stirred at room temperature for 6 hours. The reaction mixture was then heated to 80° C. for additional 20 h at which time LCMS indicated that the reaction was complete. The reaction mixture was cooled to room temperature, leading to the formation of a precipitate. This solid was filtered and dried to afford a yellow solid (350 mg). The filtrate was concentrated to dryness, diluted with ethyl acetate (100 mL) and water (100 mL). The layers were separated and the aqueous layer was extracted with ethyl acetate (2×100 mL). The combined organic layers were washed with saturated sodium chloride solution, dried (sodium sulfate), filtered and concentrated to obtain additional 380 mg of the desired product. The solid batches were combined to afford Int-14 (730 mg, 58% yield) as a dark yellow solid. MS ES+ m/z 322.1 [M+H]+

A mixture of intermediate Int-14 (350 mg, 1.09 mmol) and POCl$_3$ (2.00 mL, 21.8 mmol) was stirred at 90° C. for 3 h at which time LCMS indicated complete conversion. The POCl3 was removed in vacuo and the resulting residue was partitioned between saturated aqueous sodium bicarbonate solution (25 mL) and dichloromethane (50 mL). The aqueous layer was extracted with dichloromethane (2×25 mL) and the combined organic extracts were dried (MgSO4), filtered and concentrated under reduced pressure to afford crude Int-15 (380 mg, 103% yield). It was used without purification in the next step. MS ES+ m/z 340.1 [M+H]+

Compound I-9

Int-15

Compound I-9

A solution of intermediate Int-15 (1.0 equiv.) and 2-aminoethan-1-ol (3.0 equiv.) in DMSO (1 mL) was added triethylamine (5.0 equiv.) was heated to 90° C. for 18 hours. The reaction mixture was cooled to room temperature, leading to the formation of a precipitate which was collected. Purification of the crude solid product was achieved by reverse phase HPLC utilizing a gradient of 20 to 50% acetonitrile in water (modified by 0.1% formic acid) to afford Compound I-9 as a clear glass. $^1$H NMR (500 MHz, CD$_3$OD) δ (ppm) 9.58 (br s, 1H), 8.26 (s, 2H), 8.21 (s, 1H), 7.87 (s, 1H), 7.18-7.30 (m, 2H), 7.04-7.08 (m, 1H), 7.00-7.04 (m, 1H), 4.67 (s, 2H), 3.81 (br s, 4H). MS ES+ m/z 366.1 [M+H]+(secondary protonation observed).

Intermediate 16

8-(3,5-difluoro-4-methylbenzyl)imidazo[1,2-a]pyrazine-6-carbonitrile (Int-16)

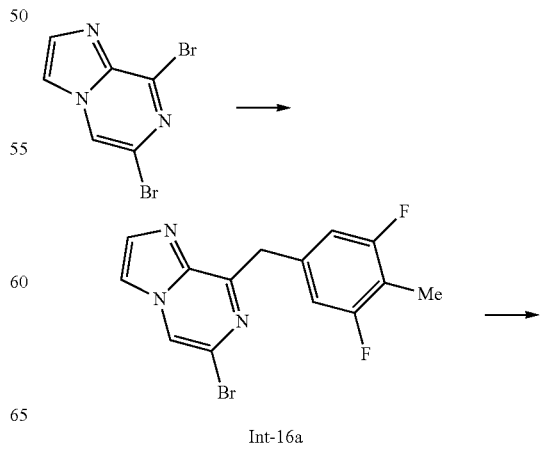

Int-16a

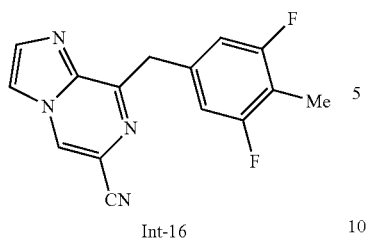
Int-16

Nitrile intermediate Int-16 was prepared from the starting bromide, 6,8-dibromoimidazo[1,2-a]pyrazine, using 3,5-difluoro-4-methylbenzyl bromide according to the patent literature procedure (WO 2015/187470A1) described for the synthesis of intermediate Int-1. MS ES+ m/z=285.2 [M+H]+.

Intermediate-19

6-(4,5-dichloropyrimidin-2-yl)-8-(3,5-difluoro-4-methylbenzyl)imidazo[1,2-a]pyrazine (Int-19)

Amidine intermediate Int-17 was prepared from Int-16 as described in the synthesis of Int-2 from Int-1. MS ES+ m/z=302.2 [M+H]+.

Intermediate Int-19 was prepared from Int-17 as described in the procedure for the preparation of Int-13 from 8-(2-fluorobenzyl)imidazo[1,2-a]pyrazine-6-carboximidamide.
$^1$H NMR (500 MHz, CD$_3$OD) δ (ppm): 9.88 (s, 1H), 8.79-8.90 (m, 1H), 8.58 (d, 1H), 8.36 (d, 1H), 7.06-7.20 (m, 2H), 4.71 (s, 2H), 2.15 (s, 3H). MS ES+ m/z 406.1 [M+H]+

Compound I-10

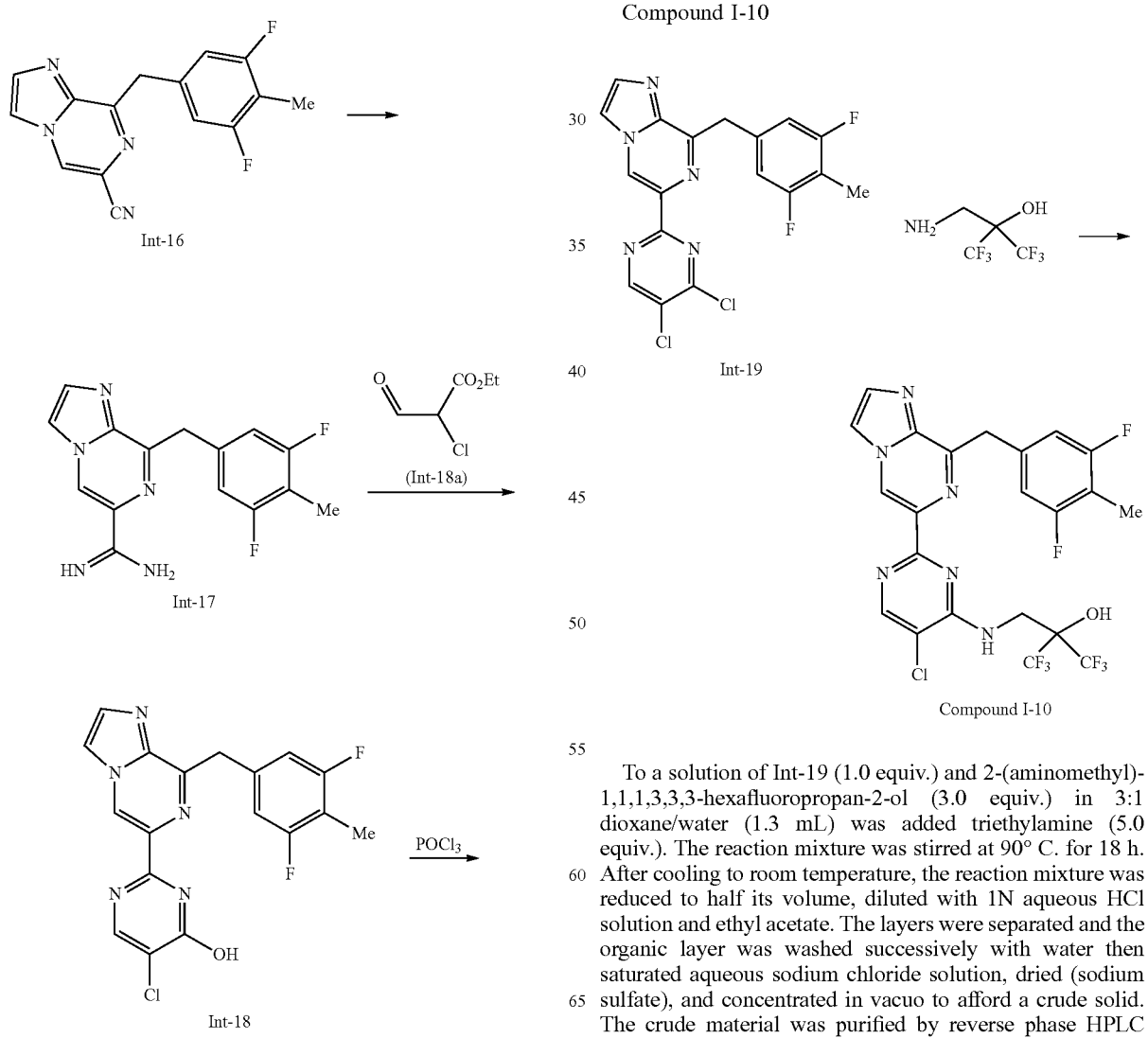

To a solution of Int-19 (1.0 equiv.) and 2-(aminomethyl)-1,1,1,3,3,3-hexafluoropropan-2-ol (3.0 equiv.) in 3:1 dioxane/water (1.3 mL) was added triethylamine (5.0 equiv.). The reaction mixture was stirred at 90° C. for 18 h. After cooling to room temperature, the reaction mixture was reduced to half its volume, diluted with 1N aqueous HCl solution and ethyl acetate. The layers were separated and the organic layer was washed successively with water then saturated aqueous sodium chloride solution, dried (sodium sulfate), and concentrated in vacuo to afford a crude solid. The crude material was purified by reverse phase HPLC using a gradient of 30 to 60% acetonitrile in water (modified by 0.1% formic acid) to provide Compound I-10 (9.7 mg, 14% yield) as a off-white solid. $^1$H NMR (500 MHz, CD$_3$OD) δ (ppm): 9.38 (s, 1H), 8.41 (s, 1H), 8.14 (s, 1 H), 7.86 (s, 1 H), 7.23 (d, 2H), 4.49 (s, 2H), 4.17 (s, 2H), 2.08 (s, 3H). MS ES$^+$ m/z 567.2 [M+H]$^+$ Intermediate-21

6-(4-chloro-5-methoxypyrimidin-2-yl)-8-(2-fluorobenzyl)-[1,2,4]triazolo[1,5-a]pyrazine (Int-21)

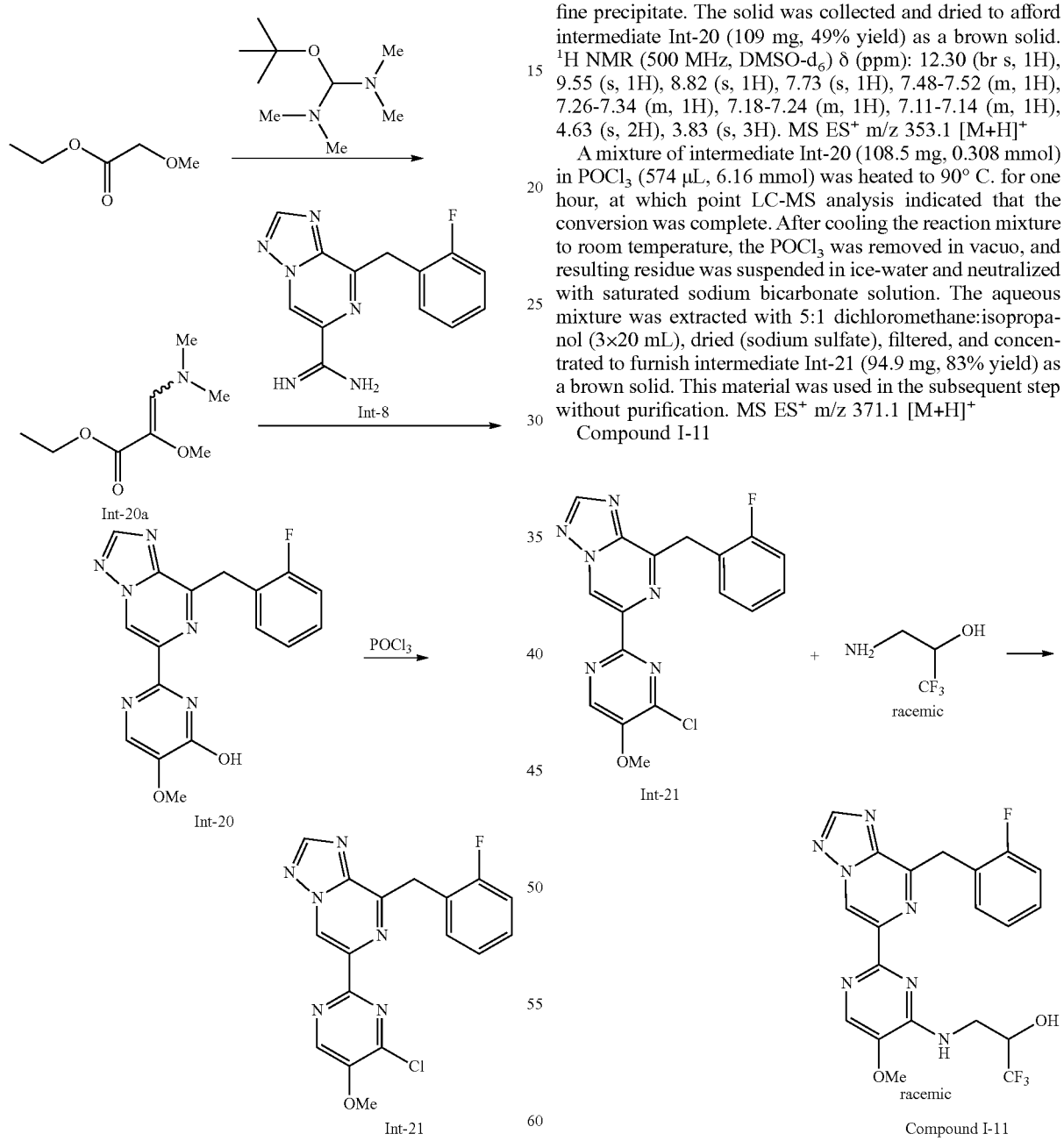

gradient of 0 to 60% ethyl acetate in hexanes over 30 minutes to afford ethyl 3-(dimethylamino)-2-methoxyacrylate (Int-20a) as a light-yellow oil. MS ES$^+$ m/z 174.0 [M+H]$^+$ A solution of intermediates Int-8 (170 mg, 0.629 mmol), Int-20a (327 mg, 1.89 mmol) and DBU (0.285 mL, 1.89 mmol) in absolute ethanol (1.5 mL) was heated at 90° C. for 1 hour, after which LC-MS analysis indicated that the conversion was complete. After cooling to room temperature, the reaction mixture was acidified to pH 2-3 with a 2.5 M in ethanol solution of HCl, leading to the formation of a fine precipitate. The solid was collected and dried to afford intermediate Int-20 (109 mg, 49% yield) as a brown solid. $^1$H NMR (500 MHz, DMSO-d$_6$) δ (ppm): 12.30 (br s, 1H), 9.55 (s, 1H), 8.82 (s, 1H), 7.73 (s, 1H), 7.48-7.52 (m, 1H), 7.26-7.34 (m, 1H), 7.18-7.24 (m, 1H), 7.11-7.14 (m, 1H), 4.63 (s, 2H), 3.83 (s, 3H). MS ES$^+$ m/z 353.1 [M+H]$^+$ A mixture of intermediate Int-20 (108.5 mg, 0.308 mmol) in POCl$_3$ (574 µL, 6.16 mmol) was heated to 90° C. for one hour, at which point LC-MS analysis indicated that the conversion was complete. After cooling the reaction mixture to room temperature, the POCl$_3$ was removed in vacuo, and resulting residue was suspended in ice-water and neutralized with saturated sodium bicarbonate solution. The aqueous mixture was extracted with 5:1 dichloromethane:isopropanol (3×20 mL), dried (sodium sulfate), filtered, and concentrated to furnish intermediate Int-21 (94.9 mg, 83% yield) as a brown solid. This material was used in the subsequent step without purification. MS ES$^+$ m/z 371.1 [M+H]$^+$ Compound I-11

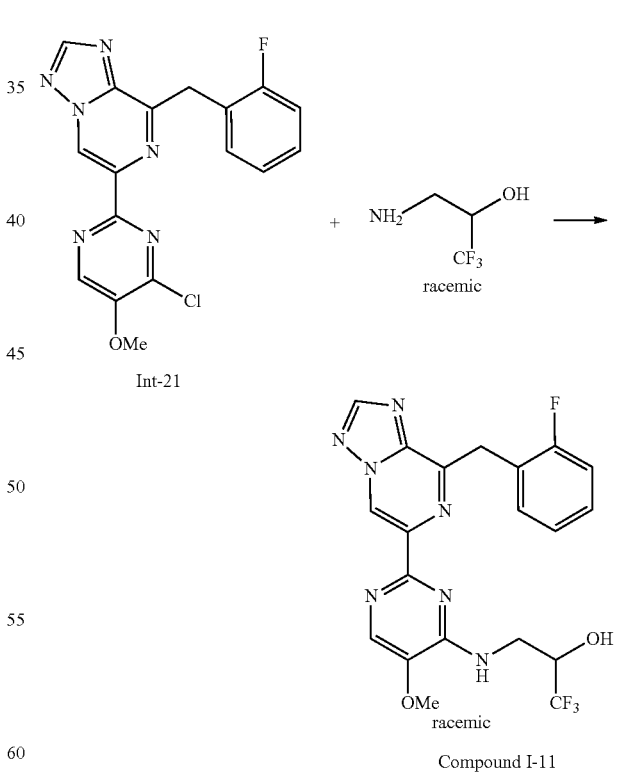

A mixture of ethyl methoxyacetate (1.0 equiv.) and tert-butoxybis(dimethylamino)methane (2.0 equiv.) was heated at 110° C. for 21 hours, at which point LCMS indicated conversion to product. The crude reaction mixture was directly purified by silica gel chromatography utilizing a A suspension of intermediate Int-21 (1.0 equiv.) and racemic-3-Amino-1,1,1-trifluoro-propan-2-ol (3.0 equiv.), and triethylamine (5.0 equiv) in 3:1 dioxane/water (1.3 mL) was heated at 90° C. for 12 hours, after which LC-MS analysis indicated that the conversion was complete. The reaction mixture was diluted with water and adjusted to pH 6-7 with 1.0 N aqueous hydrochloric acid solution, leading to the formation of an orange precipitate. The solid was filtered and dried. Purification of the crude solid was achieved by reverse phase HPLC utilizing a gradient of 10 to 40% acetonitrile in water (modified by 0.1% trifluoroacetic acid) over 20 min to afford racemic Compound I-11 (57.4 mg, 48% yield) as an off-white solid. $^1$H NMR: (500 MHz, CD$_3$OD), δ (ppm): 9.63 (s, 1H), 8.61 (s, 1H), 7.74 (s, 1H), 7.30-7.33 (m, 1H), 7.15-7.20 (m, 1H), 6.97-7.01 (m, 2H, overlapping shifts), 4.67 (s, 2H), 4.28-4.32 (m, 1H), 3.98-4.02 (m, 4H, overlapping shifts), 3.86-3.91 (m, 1H). MS ES$^+$ m/z 464.2 [M+H]$^+$ Intermediate-23

4-chloro-2-(8-(2-fluorobenzyl)-[1,2,4]triazolo[1,5-a]pyrazin-6-yl)pyrimidine-5-carbonitrile (Int-23)

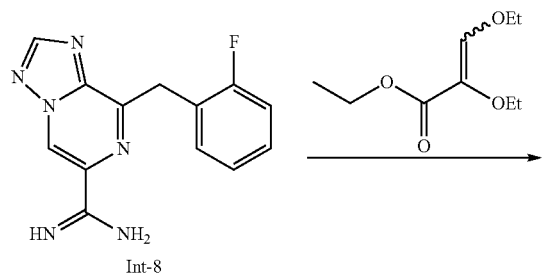

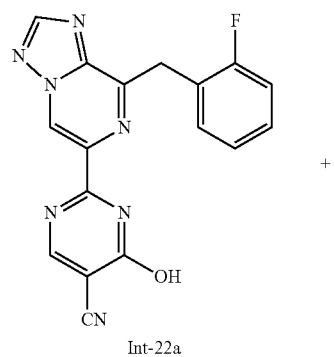

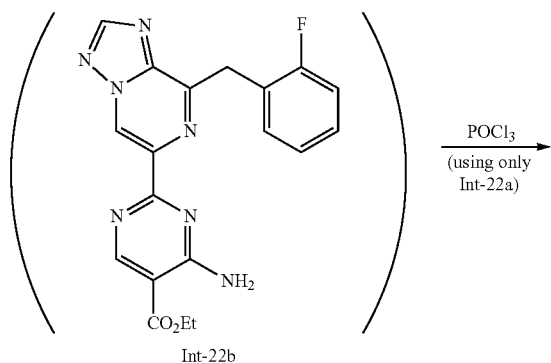

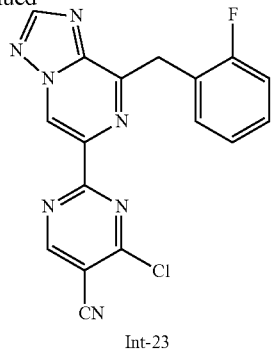

A solution of ethyl (ethoxymethylene)cyanoacetate (1.72 g, 10.2 mmol), Int-8 (0.917 g, 3.39 mmol), and DBU (1.53 mL, 10.2 mmol) in ethanol (6.8 mL) was heated to 100° C. for 24 hours, after which LC-MS analysis indicated a mixture of products. The reaction was then cooled to room temperature and acidified by the addition of a 2.5 N in ethanol solution of HCl (4.07 mL, 10.2 mmol). The reaction mixture was concentrated to dryness, then purified by silica gel chromatography utilizing a gradient of 0 to 100% of a 7:1 acetonitrile/methanol solution in dichloromethane over 75 minutes. A second purification was needed using silica gel chromatography utilizing a gradient of 0 to 70% of a 7:1 acetonitrile/methanol solution in dichloromethane over 75 minutes to afford Int-22a (214 mg, 16% yield) as a brown solid (~90% purity). Int-22b was not isolated. $^1$H NMR (Int-22a): (500 MHz, DMSO-d$_6$), δ (ppm): 13.43 (br. s, 1H), 9.78 (s, 1H), 8.88 (s, 1H), 8.80 (br. s, 1H), 7.44-7.53 (br. m, 1H), 7.28-7.32 (m, 1H), 7.19-7.22 (m, 1H), 7.09-7.12 (m, 1H), 4.64 (s, 2H). MS ES$^+$ m/z 348.1 [M+H]$^+$ A suspension of Int-22a (211 mg, 0.608 mmol) was heated in POCl$_3$ (1.42 mL, 15.2 mmol) at 80° C. After 3 hours, LC-MS analysis indicated that conversion was complete. The reaction was concentrated to dryness to afford crude Int-23 (331 mg.) as a brown solid. $^1$H NMR: (500 MHz, DMSO-d$_6$), δ (ppm): 9.84 (s, 1H), 9.49 (s, 1H), 8.88 (s, 1H), 7.40-7.43 (m, 1H), 7.28-7.33 (m, 1H), 7.18-7.21 (m, 1H), 7.11-7.14 (m, 1H), 4.67 (s, 2H). MS ES$^+$ m/z 366.1 [M+H]$^+$ Compound I-12

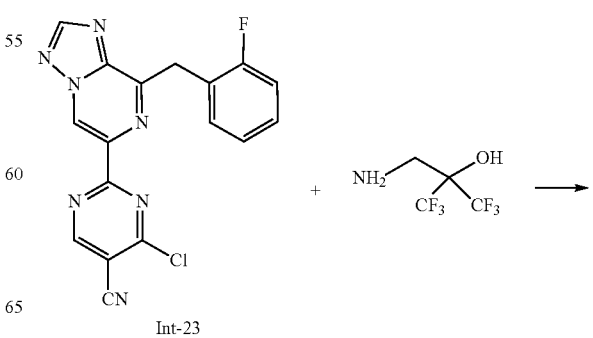

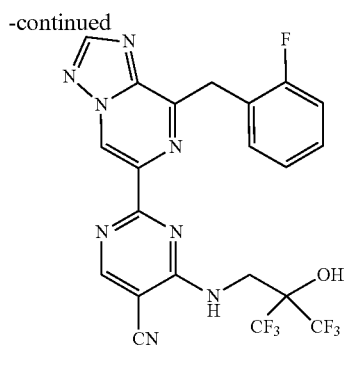

Compound I-12

A solution of intermediate Int-23 (1.0 equiv.), N-ethyl-N-isopropylpropan-2-amine (10.0 equiv.), and 2-(aminomethyl)-1,1,1,3,3,3-hexafluoropropan-2-ol (2.5 equiv.) in dimethyl sulfoxide (1.2 ml) was heated to 95° C. for 24 hours. After cooling to room temperature, the reaction mixture was purified directly by reverse phase HPLC utilizing a gradient of 20 to 60% acetonitrile in water (modified by 0.1% formic acid) over 10 minutes to afford Compound I-12 (8.6 mg, 8% yield) as a gold solid. $^1$H NMR: (500 MHz, DMSO-$d_6$), δ (ppm): 9.71 (s, 1H), 8.94 (s, 1H), 8.85 (s, 1H), 8.62 (br. s, 1H), 8.19 (s, 1H), 7.46-7.49 (m, 1H), 7.26-7.30 (m, 1H), 7.15-7.18 (m, 1H), 7.07-7.10 (m, 1H), 4.61 (s, 2H), 4.23-4.26 (m, 2H). MS ES$^-$ m/z 525.4 [M−H]$^-$ Intermediate 24

8-(thiophen-3-ylmethyl)imidazo[1,2-a]pyrazine-6-carbonitrile (Int-24)

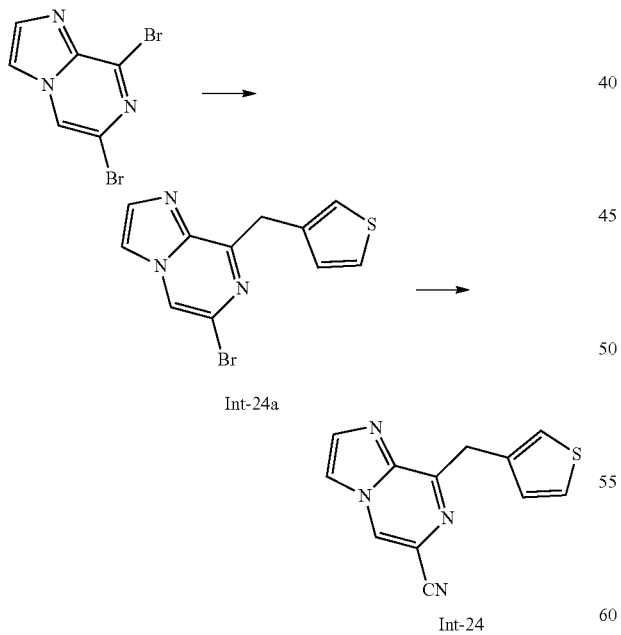

Nitrile intermediate Int-24 was prepared from the starting bromide, 6,8-dibromoimidazo[1,2-a]pyrazine, using 3-(chloromethyl)thiophene according to the patent literature procedure (WO 2015/187470A1) described for the synthesis of Intermediate-1 as well as reference to *J. Org. Chem.* 2018, 83, 11437-11445 for generation of (thiophen-3-ylmethyl)zinc(II) chloride. Intermediate Int-24a was isolated as an off-white solid (68% yield), and Int-24 was isolated as a yellow solid (36% yield). Int-24a: MS ES$^+$ m/z 295.9 [M+H]$^+$. Int-24: MS ES$^+$ m/z 241.0 [M+H]$^+$.

Intermediate-26

6-(4-chloro-5-fluoropyrimidin-2-yl)-8-(thiophen-3-ylmethyl)imidazo[1,2-a]pyrazine (Int-26)

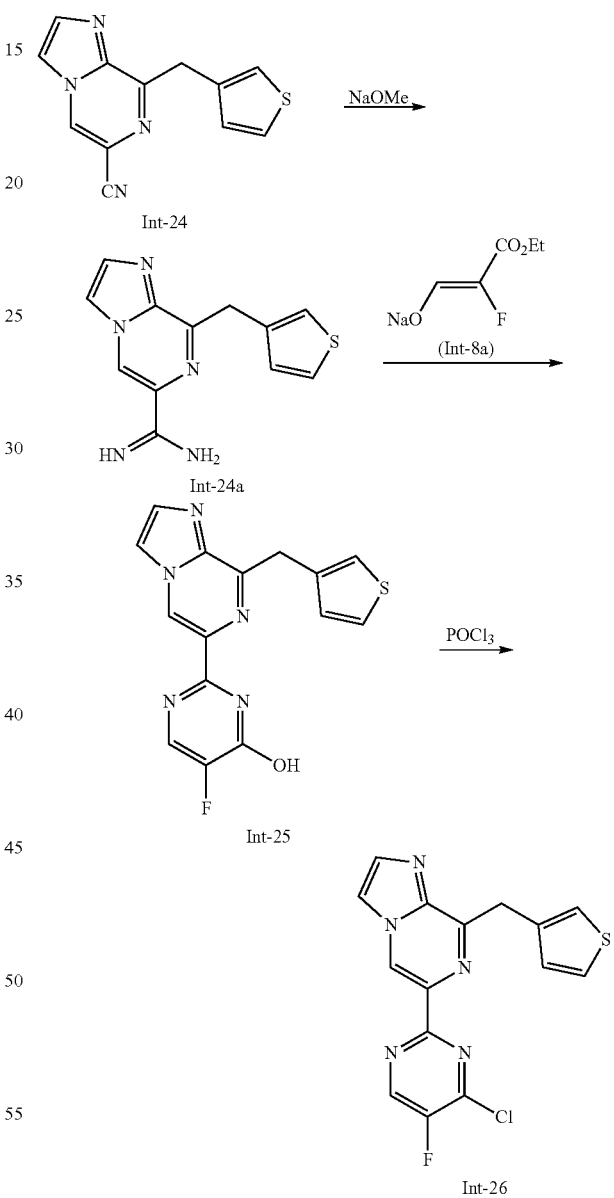

Intermediate Int-26 was prepared via the same procedure as outlined for the preparation of Int-3 from Int-1. Int 25a: MS ES$^+$ m/z 258.0 [M+H]$^+$. Int 25: $^1$H NMR: (500 MHz, DMSO-d), δ (ppm): 12.82 (br s, 1 H), 9.46 (br s, 1H), 8.30 (s, 1 H), 8.22 (br s, 1 H), 7.90 (s, 1H), 7.43-7.46 (m, 2H, overlapping shifts), 7.30 (br s, 1H), 4.54 (s, 2H). MS ES$^+$ m/z 328.0 [M+H]$^+$. Int 26: MS ES$^+$ m/z 346.0 [M+H]$^+$ Compound I-13

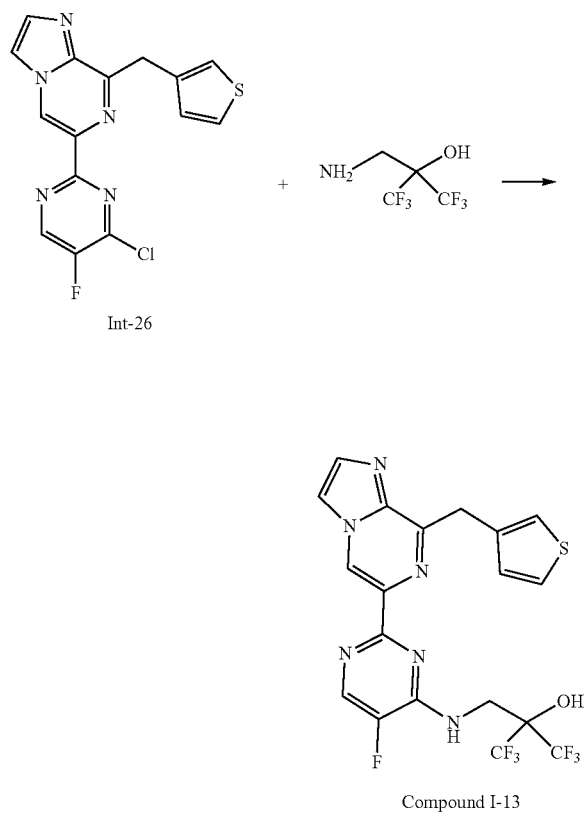

Compound I-13

A solution of intermediate Int-26 (1.0 equiv) and 2-(aminomethyl)-1,1,1,3,3,3-hexafluoropropan-2-ol (3.0 equiv.) and triethylamine (5.0 equiv.) in 2:1 dioxane/water (0.6 mL) was heated at 90° C. for 22 h. after which the reaction was complete. The reaction mixture was diluted with water and extracted with dichloromethane:isopropanol (5:1) (3×25 mL). The combined organic layers were dried (sodium sulfate), filtered, and concentrated to a brown residue. Purification was achieved by silica gel chromatography using a gradient of 0 to 40% of a 7:1 acetonitrile/methanol in dichloromethane over 12 minutes to afford Compound I-13 (15 mg, 25% yield) as an off-white solid. $^1$H NMR: (500 MHz, DMSO-$d_6$), δ (ppm): 9.57 (s, 1H), 9.42 (s, 1H), 8.48-8.51 (m, 2H, overlapping shifts), 8.28 (s, 1H), 7.87 (s, 1H), 7.42 (br s, 1H), 7.38 (br s, 1H), 7.26-7.27 (m, 1H), 4.42 (s, 2H), 4.08-4.09 (m, 2H). MS ES$^+$ m/z 507.1 [M+H]$^+$ Intermediate-27

8-((2-methylpyrimidin-5-yl)methyl)imidazo[1,2-a]pyrazine-6-carbonitrile (Int-27)

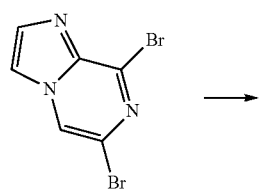

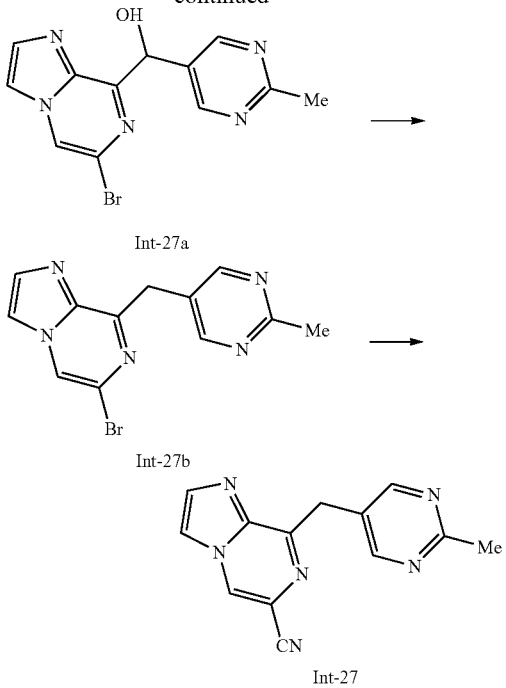

Intermediate Int-27a is prepared by lithiation of starting bromide, 6,8-dibromoimidazo[1,2-a]pyrazine and quenching with 2-methylpyrimidine-5-carbaldehyde according to *Journal of the American Chemical Society*, 2003, 125, 8082-8083.

Intermediate Int-27b is accessed via standard reduction using trifluoroacetic acid and triethylsilane. Conversion of Int-27b to intermediate cyano intermediate Int-27 is achieved by using the procedure outlined for the preparation of Int-1.

Intermediate 28

6-(4-chloro-5-fluoropyrimidin-2-yl)-8-(2,5-difluorobenzyl)imidazo[1,2-a]pyrazine (Int-28)

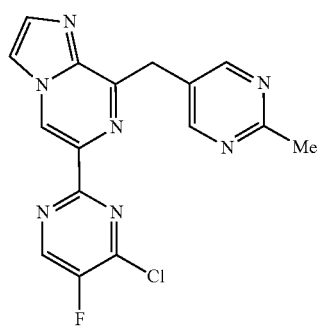

Intermediate Int-28 is prepared from Int-27 according to the general procedure described for the synthesis of Int-3 from Int-1.

Compound I-14

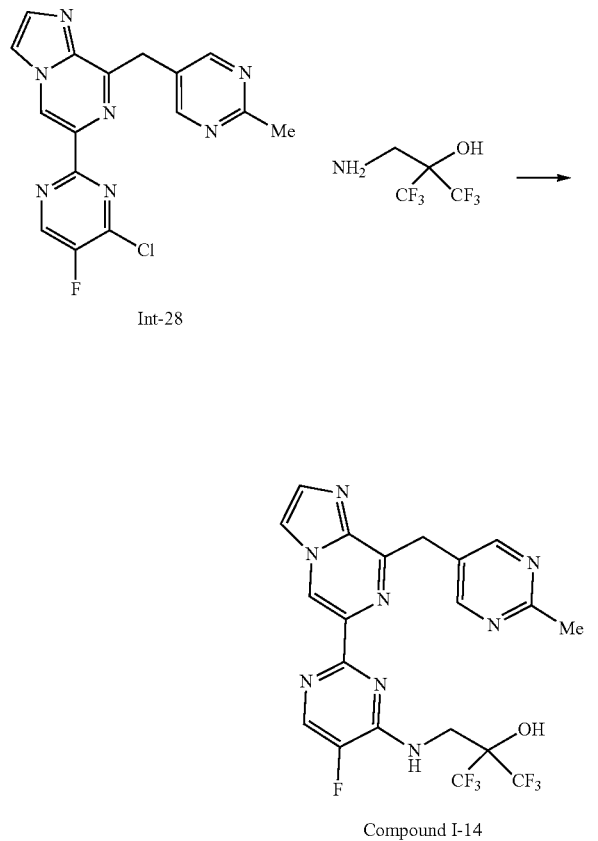

Int-28

Compound I-14

Compound I-14 is prepared using the same conditions outlined for the preparation of Compound I-2 from Int-3.

Compound I-15

The di sodium salt of prodrug I-1 was prepared using NaOMe and following the procedure described in experimental J. Med. Chem. 2008, 51, 1111-1114.

Compound I-16

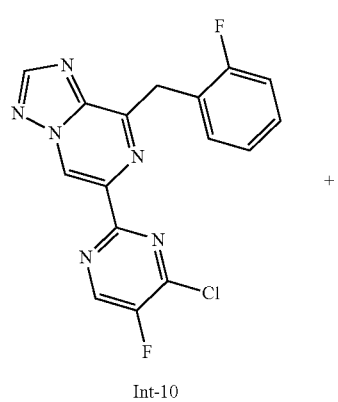

Int-10

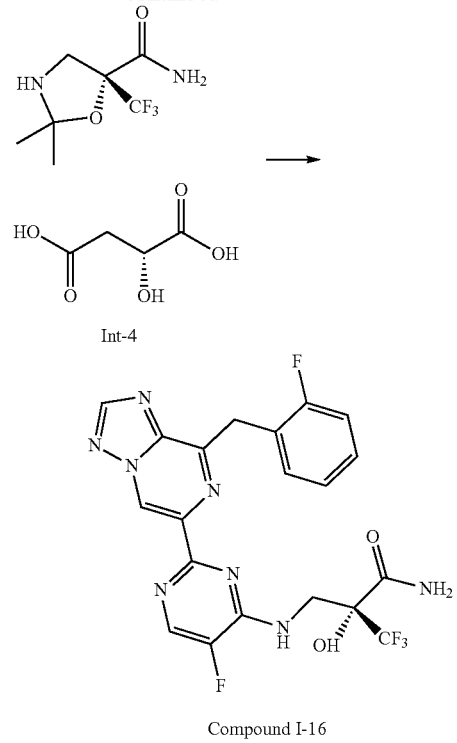

Int-4

Compound I-16

A solution of intermediate Int-10 (1 equiv.), intermediate Int-4 (3 equiv.) and triethylamine (6.0 equiv.) in dioxane/water 1:1 (1.2 mL) was heated at 80° C. for 24 h. After cooling to room temperature, the reaction mixture was diluted in ethyl acetate, and the resulting organic layer was dried (sodium sulfate), filtered and concentrated to afford an oil. Purification of the crude product was achieved by silica gel chromatography utilizing a gradient of 0 to 100% ethyl acetate in hexanes to provide Compound I-16 (64.2 mg, 56% yield) as a light-yellow solid. $^1$H NMR (500 MHz, CDCl$_3$) δ ppm 9.52 (s, 1H), 8.56 (s, 1H), 8.26 (s, 1H), 7.64 (app. t, 1H), 7.20-7.25 (m, 2H), 7.02-7.14 (m, 2H), 4.77 (s, 2H), 4.22-4.28 (m, 2H) [2 acidic protons not observed due to exchange with CDCl$_3$]. Compound I-16: MS ES$^+$ m/z 495.1 [M+H]$^+$.

Example 2: Biological Activity Measurement by the cGMP GloSensor™ Cell-Based Assay, 384-Well Format Human embryonic kidney cells (HEK293) cells expressing GloSensor™ 40F cGMP (Part No: CS182801, Promega) were used to evaluate the activity of test compounds. The luminescent biosensors (engineered luciferase) that were incorporated into these cells detect cGMP formed by the compounds stimulating the sGC enzyme and emit luminescence.

cGMP GoSensor cells were maintained in Dulbecco's Modification of Eagle's Medium (DMEM) supplemented with fetal bovine serum (FBS, 10% final) and hygromycine (200 ug/ml). The day before assay, cells were plated in DMEM with 10% FBS in a 50 μL volume at a density of 1.5×10$^4$ cells/well in a poly-D-lysine coated 384-well flat white-bottom plate (Corning Cat No 35661). Cells were incubated overnight at 37° C. in a humidified chamber with 5% CO$_2$. The next day, medium was removed and cells were replaced with 40 ul/well of GoSensor™, 2 mM (Promega Cat No E1291). Cells were treated for 90 minutes at 25° C. to allow the substrate to equilibrate in the cells. Test compounds and Diethylenetriamine NONOate (DETA-NONOate) was diluted to 3 mM (20×) in serum-free $CO_2$ independent medium and serially diluted at 4× dilutions to create 5× dose curve from which 10 ul was added to the wells (x μM concentration for test compound solution and 10 μM concentration for DETA-NONOate solution; wherein x is one of the following final concentrations).

| |
|---|
| 30000 nM |
| 7500 nM |
| 1875 nM |
| 468.75 nM |
| 117.19 nM |
| 29.29 nM |
| 7.32 nM |
| 1.83 nM |
| 0.46 nM |
| 0.114 nM |
| 0.029 nM |

For the kinetics studies, luminescence was measured right away for 0.2 sec per well with Envision (Perkin Elmer). For endpoint SAR screening, data were collected after 55 min incubation at room temperature.

Data were normalized to a high control using the following equation: 100*(Sample-Low Control)/(High Control-Low Control), where the low control is the average of sixteen DMSO (1%) control datapoints, and the high control is the average of sixteen Compound Y (30 μM) datapoints, wherein Compound Y is depicted below. Data were fit using a 4-parameter fit (log(agonist) vs. response—variable slope) using GraphPad Prism Software v.5. n=2 for all compounds. The Absolute $EC_{50}$ was interpolated from the curve fit and is defined as the concentration at which a given compound elicits 50% of the high control response after data normalization as indicated above. Compounds failing to elicit a minimum response of 50% are reported as >30 μM or ND (not determined). For compounds run in duplicate or n higher than 2, the result herein given is the geometric mean of the several results obtained. Table II summarizes results obtained for selected compounds of Table I, respectively.

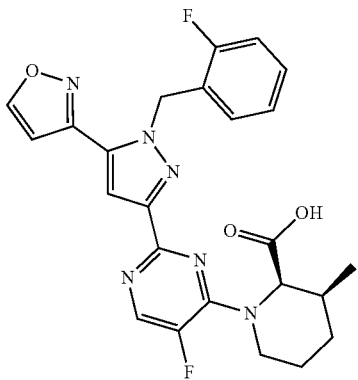

Compound Y

TABLE II

Whole cell activity in the GloSensor cell-based assay, 384-well format (Example 2, compounds in Table I)

| Compound | Glo-sGC Absolute EC50 (nM) |
|---|---|
| I-2 | A |
| I-3 | A |
| I-5 | A |
| I-6 | B |
| I-7 | B |
| I-8 | B |
| I-9 | B |
| I-10 | C |
| I-11 | C |
| I-12 | B |
| I-15 | C |
| I-16 | B | sGC enzyme activity values in HEK cells, determined by the GloSensor assay. (~) Code definitions for the sGC enzyme activity values, expressed as Absolute $EC_{50}$ which is defined as the concentration at which a given compound elicits 50% of the high control response (Compound Y) after data normalization.
EC50 Abs ≤ 100 nM = A;
100 nM < EC50Abs ≤ 1000 nM = B;
1000 nM < EC50Abs ≤ 30 μM = C;
30 μM < EC50Abs = D.
Compounds failing to elicit a maximum response of less than 50% of the high control were reported as >30 μM (and would fall within category D).

Example 3: Blood Pressure Change in Sprague-Dawley Rats

Male rats (250-350 g body weight, supplied by Harlan Laboratories) were anesthetized with ketamine/xylazine and a heparinized saline fluid filled catheter implanted into the right femoral artery. The catheter was exteriorized between the scapula, capped, and the animal allowed to recover for at least 7 days post surgery prior to any compound testing. Prior to testing animals were maintained on normal diet, with free access to drinking water, under a 12 hour light-dark cycle.

On the day of experimentation, under inhaled isoflurane anesthesia, the catheter was uncapped and connected to a tether (Instech Labs) and pressure transducer (Harvard Apparatus). Blood pressure and heart rate were subsequently captured and analyzed with a dedicated data capture system (PowerLab, ADInstruments). Data sampling rates were set at 1 cycle per second. Once connected, each rat was allowed to recover from anesthesia and baseline blood pressure and heart rate levels were established in these conscious, freely-moving animals. Once baseline was established either vehicle (0.5% methylcellulose or 100% PEG400) or test article was administered orally (PO, 10 mg/kg) and the effects on blood pressure and heart rate monitored for up to 24 hours.

The sodium salt (Compound I-15), of the phosphorus prodrug (Compound I-1) of Compound I-2 was dosed orally in water at 10 mg/kg to determine the blood pressure effects of Compound I-2. At one hour post-dose, 97.5% of the dosed Compound I-15 had been converted to Compound I-2. At 160 minutes post-dose, Compound I-2, had decreased the value of MAP (mean arterial pressure) by about 10 mmHg below baseline.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A compound of Formula I, or a pharmaceutically acceptable salt thereof,

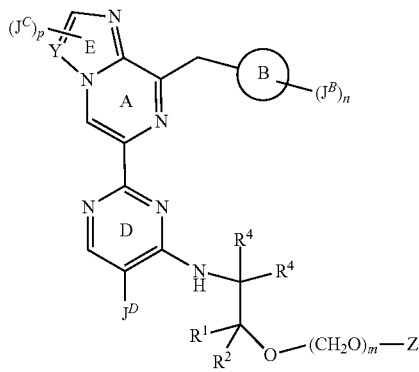

Formula I wherein:

Y is independently N or C;

ring B is a phenyl or a 5 or 6-membered heteroaryl ring, containing 1 or 2 ring heteroatoms independently selected from N, O and S;

n is an integer selected from 0 to 3; and each $J^B$ is independently halogen, —CN, a $C_{1-6}$ aliphatic or —$OR^B$;

wherein each $J^B$ that is a $C_{1-6}$ aliphatic is optionally and independently substituted with up to 3 instances of $R^3$;

each $R^B$ is independently hydrogen or a $C_{1-6}$ aliphatic; said $C_{1-6}$ aliphatic represented by $R^B$ is optionally and independently substituted with up to 3 instances of $R^{3a}$;

each $R^3$ and $R^{3a}$ is, in each instance, independently halogen, —CN, $C_{1-4}$ alkyl, $C_{1-4}$ haloalkyl, —O($C_{1-4}$ alkyl) or —O($C_{1-4}$ haloalkyl);

Z is selected from the group consisting of hydrogen, —P(O)(OH)$_2$, —P(O)(OH)O$^-$M$^+$, —P(O)(O$^-$)$_2$ (M$^+$)$_2$, —P(O)(O$^-$)$_2$ D$^{2+}$ and —P(O)(O-Benzyl)$_2$; wherein M+ is a pharmaceutically acceptable monovalent cation and D$^{2+}$ is a pharmaceutically acceptable divalent cation;

m is 0 or 1;

$R^1$ is $C_{1-4}$ alkyl, $C_{1-4}$ fluoroalkyl, —C(O)NH$_2$ or hydrogen; and $R^2$ is $C_{1-4}$ alkyl, $C_{1-4}$ fluoroalkyl or hydrogen;

both instances of $R^4$ are simultaneously hydrogen or both instances of $R^4$, together with the carbon atom to which they are attached form a carbonyl group;

$J^D$ is hydrogen, halogen, methoxy or —CN p is 1 or 2; and each $J^C$ is independently hydrogen, halogen, $C_{1-4}$ aliphatic, $C_{1-4}$ alkoxy or —CN; wherein each said $C_{1-4}$ aliphatic and each said $C_{1-4}$ alkoxy is optionally and independently substituted by up to 3 instances of $C_{1-4}$ alkoxy, $C_{1-4}$ haloalkoxy, —OH or halogen.

2. The compound according to claim 1, wherein the compound is of Formula IA, Formula IB, Formula II, Formula IIA or Formula IIB:

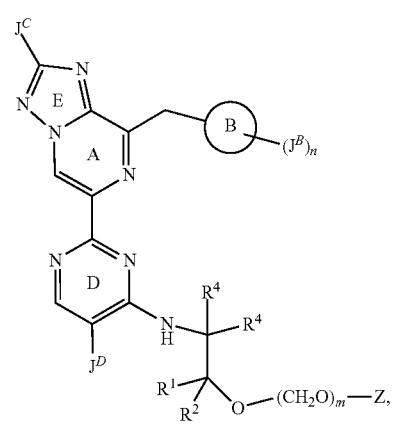

Formula IA

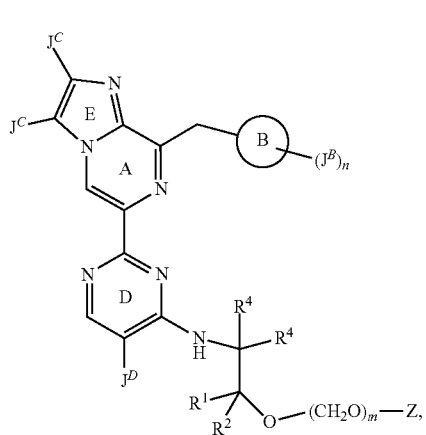

Formula IB

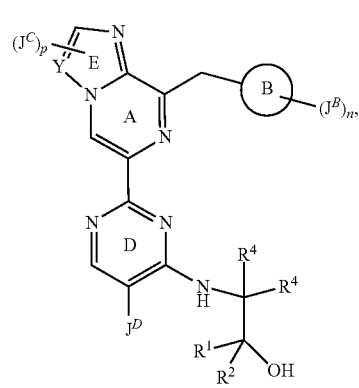

Formula II

Formula IIA

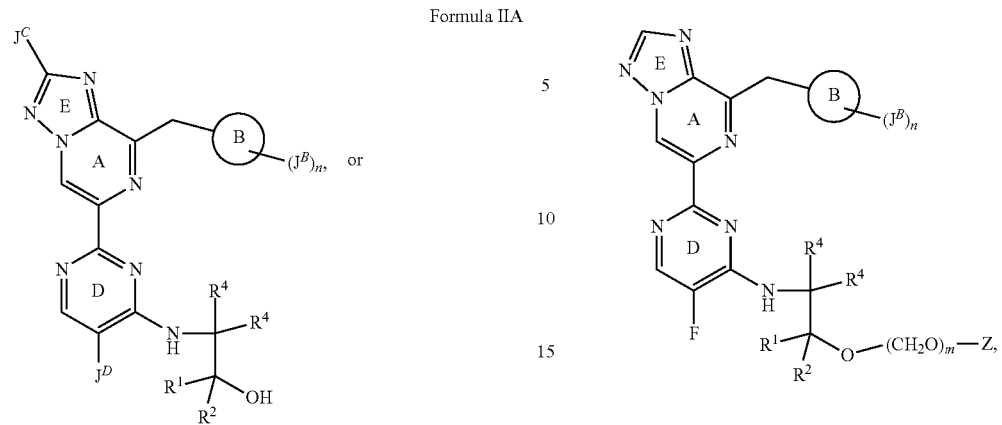

or

Formula IIB

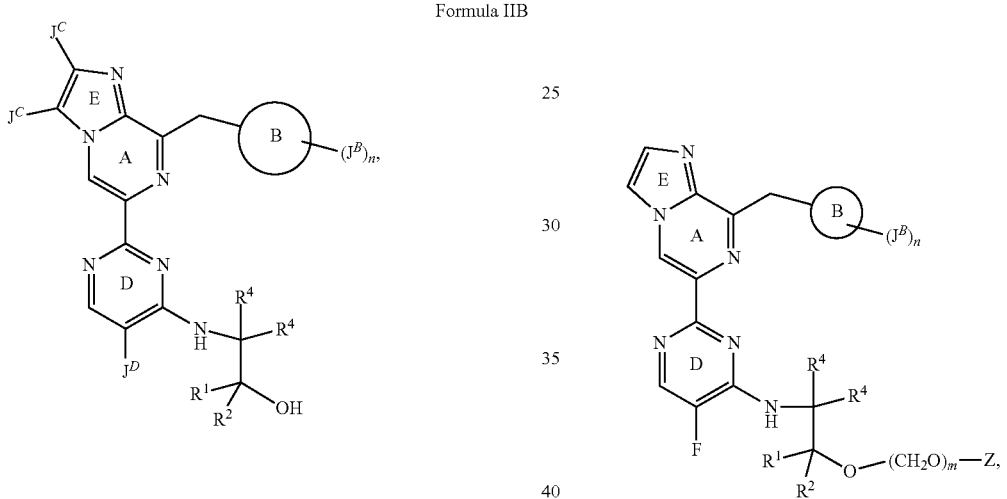

Formula IIIA

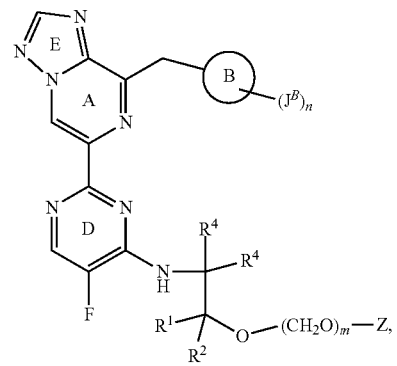

Formula IIIB

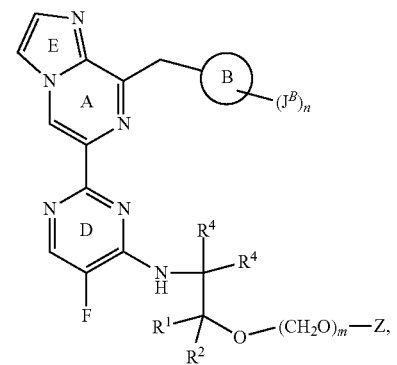

or a pharmaceutically acceptable salt thereof.

3. The compound according to claim 1, wherein (i) $J^D$ is hydrogen, chloro, fluoro, methoxy or —CN; (ii) $J^D$ is methoxy; (iii) $J^D$ is hydrogen, chloro, fluoro or —CN; (iv) $J^D$ is hydrogen, chloro or fluoro; (v) $J^D$ is fluoro or hydrogen; (vi) $J^D$ is hydrogen; (vii) $J^D$ is fluoro; (viii) $J^D$ is —CN; (ix) $J^D$ is chloro; (x) each $J^C$ is independently hydrogen, $C_{1-2}$ alkyl, $C_{1-2}$ alkoxy, $C_{1-2}$ fluoroalkyl, $C_{1-2}$ fluoroalkoxy, halogen or —CN, wherein each said $C_{1-2}$ alkyl and $C_{1-2}$ alkoxy is optionally and independently substituted by up to 3 instances of $C_{1-4}$ alkoxy, $C_{1-4}$ haloalkoxy, —OH or halogen; (xi) each $J^C$ is independently hydrogen, $C_{1-2}$ alkyl, $C_{1-2}$ alkoxy, $C_{1-2}$ fluoroalkyl, $C_{1-2}$ fluoroalkoxy, halogen or —CN; (xii) each $J^C$ is independently hydrogen or halogen; (xiv) each $J^C$ is hydrogen; or (xv) each $J^C$ is independently fluoro or chloro.

4. The compound according to claim 1, wherein the compound is of Formula IIIA, Formula IIIB, Formula IVA, Formula WB, Formula VA, Formula VIA, Formula VB or Formula VIB:

Formula IVA

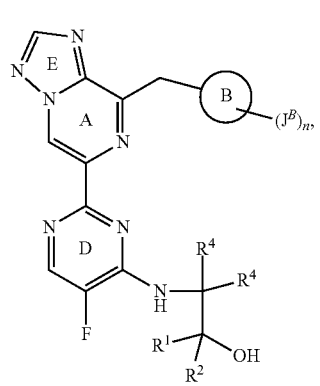

Formula IVB

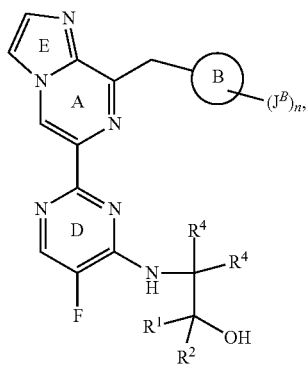

Formula VA

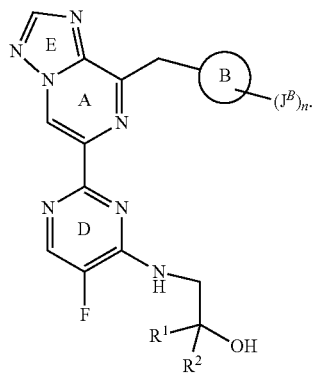

Formula VIA

Formula VB

Formula VIB

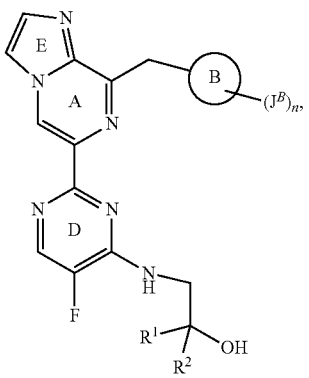

or a pharmaceutically acceptable salt thereof.

5. The compound according to claim 1, wherein (i) ring B is phenyl; (ii) ring B is a 5 or 6-membered heteroaryl ring, containing 1 or 2 ring heteroatoms independently selected from N, O and S; or (iii) ring B is a 6-membered heteroaryl ring, containing 1 to 2 ring nitrogen atoms.

6. The compound according to claim 1, wherein (i) n is 1, 2 or 3, and each $J^B$ is independently halogen or $C_{1-6}$ aliphatic; (ii) n is 1 or 2 and each $J^B$ is independently halogen or $C_{1-6}$ aliphatic; (iii) n is 1 or 2 and each $J^B$ is fluoro; (iv) n is 1 and $J^B$ is fluoro.

7. The compound according to claim 5, wherein the compound is of Formula VIIA, Formula VIIIA, Formula VIIB or Formula VIIIB:

Formula VIIA

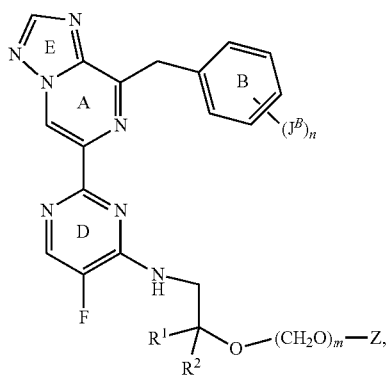

Formula VIIIA

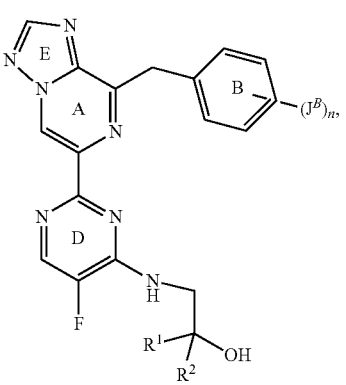

Formula VIIB

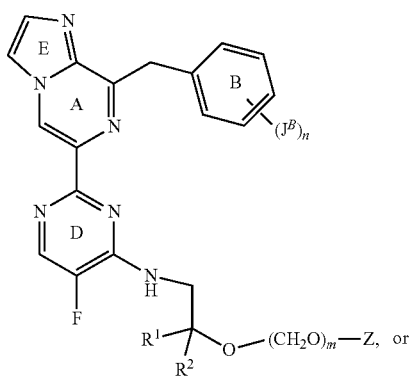

or

Formula VIIIB

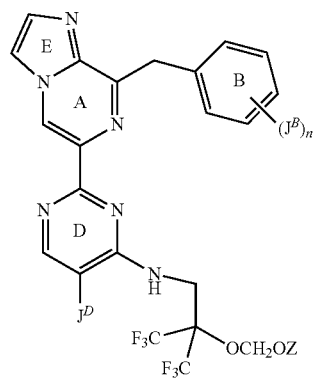

or a pharmaceutically acceptable salt thereof.

8. The compound according to claim 1, wherein (i) $R^1$ is $C_{1-2}$ alkyl, $C_{1-2}$ fluoroalkyl, hydrogen or —C(O)NH$_2$; (ii) $R^1$ is $C_{1-2}$ fluoroalkyl or —C(O)NH$_2$; (iii) $R^2$ is $C_{1-2}$ fluoroalkyl, $C_{1-2}$ alkyl or hydrogen; or (iv) $R^2$ is $C_{1-2}$ fluoroalkyl.

9. The compound of claim 8, wherein (i) $R^1$ is trifluoromethyl or —C(O)NH$_2$ and $R^2$ is trifluoromethyl; (ii) $R^1$ and $R^2$ are both hydrogen or $C_{1-2}$ alkyl; or one of $R^1$ and $R^2$ is hydrogen and the other is $C_{1-2}$ fluoroalkyl; (iii) $R^1$ and $R^2$ are both hydrogen; (iv) $R^1$ and $R^2$ are both methyl; or (v) one of $R^1$ and $R^2$ is hydrogen and the other is trifluoromethyl.

10. The compound of claim 1 selected from:

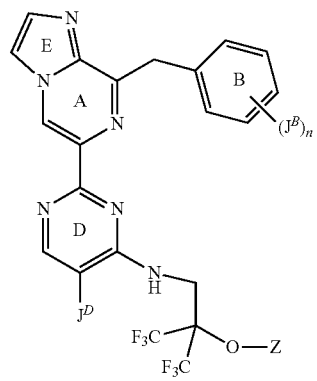

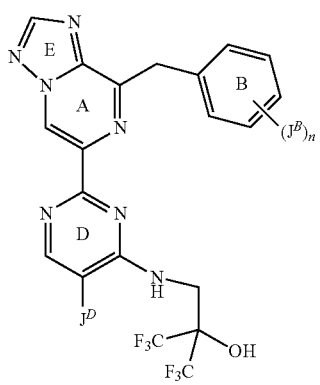

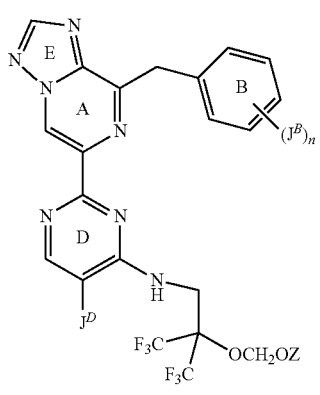

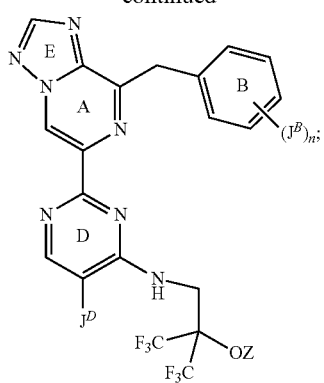

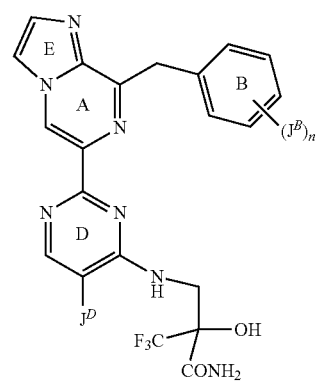

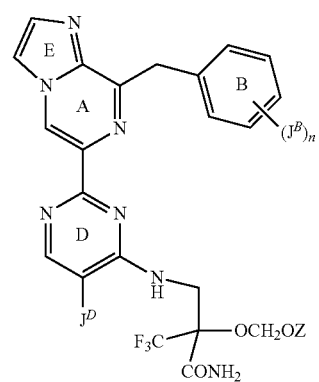

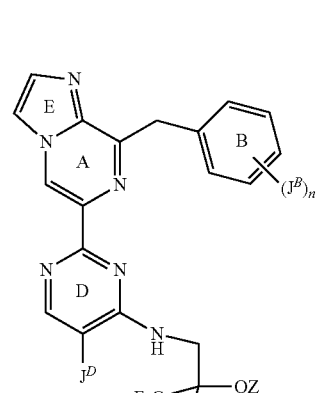

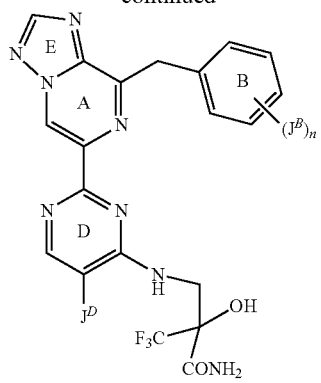

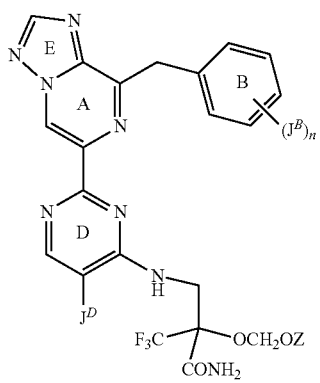

and

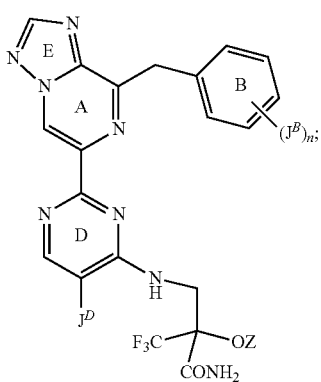

wherein $J^D$ is selected from hydrogen or fluoro.

11. The compound according to claim 1, wherein (i) Z is —P(O)(OH)$_2$; (ii) Z is —P(O)(OH)O$^-$M$^+$ or —P(O)(O$^-$)$_2$(M$^+$)$_2$; and M$^+$ is Na$^+$, K$^+$, Cs$^+$ or the monovalent cation of an organic amine; or (iii) Z is —P(O)(O$^-$)$_2$D$^{2+}$; and D$^{2+}$ is Ca$^{2+}$, Zn$^{2+}$, Mg$^{2+}$ or the divalent cation of an organic amine.

12. The compound according to claim 1 selected from the group consisting of

I-1 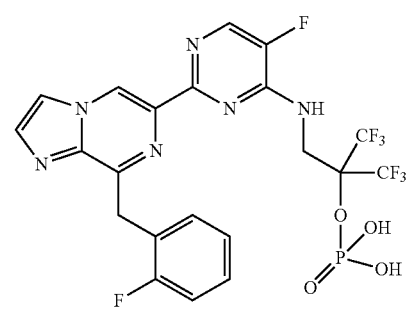
I-2 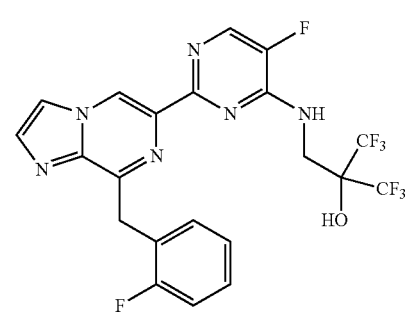
I-3 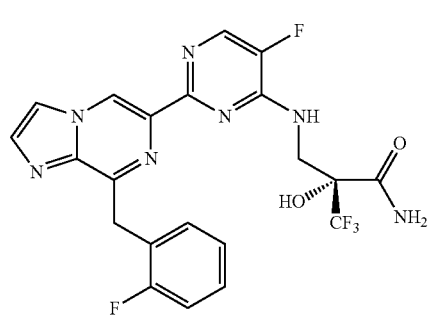
I-4 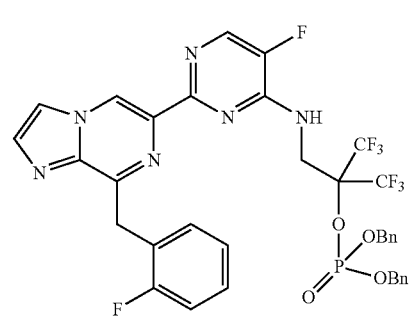
I-5 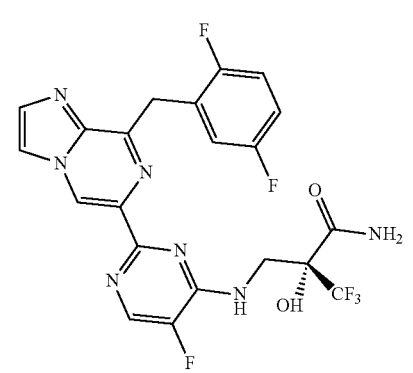
I-6 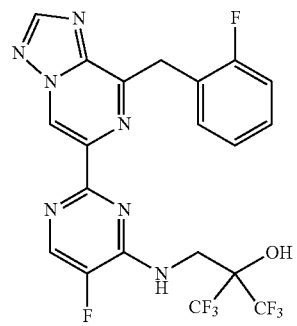
I-7 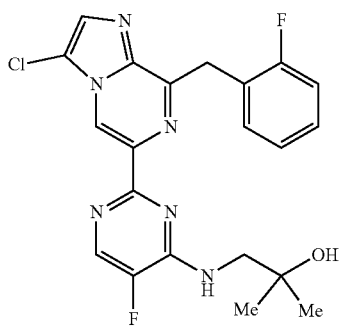
I-8 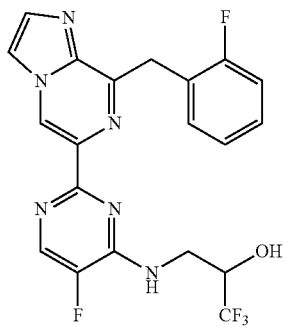
racemic
I-9 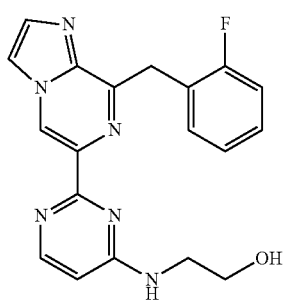
I-10 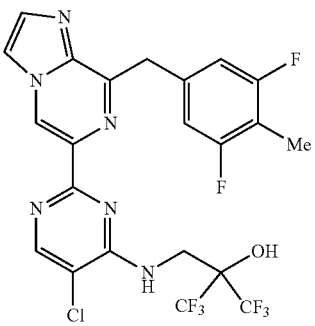

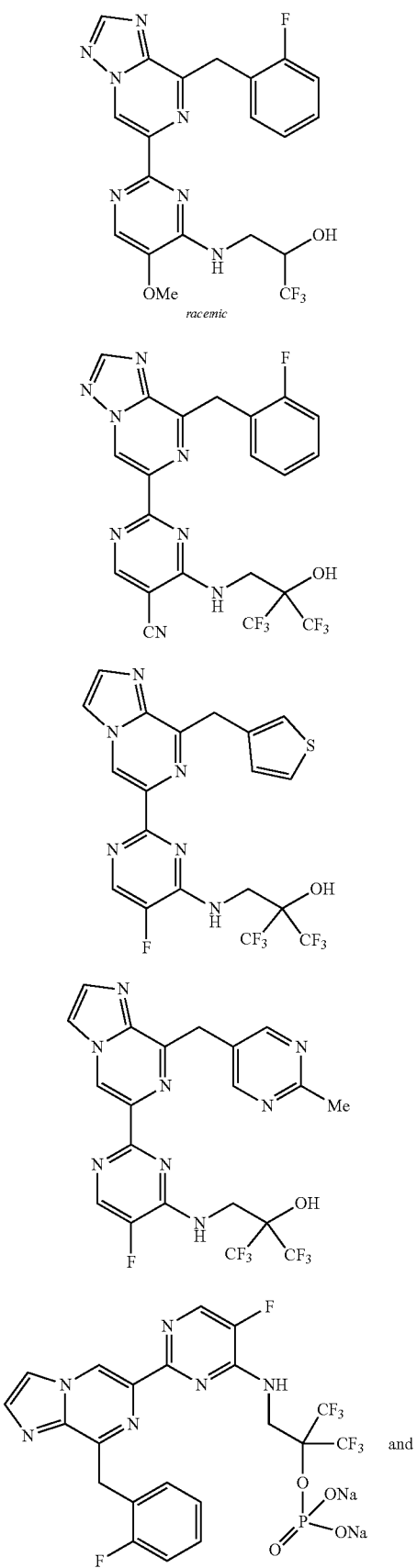

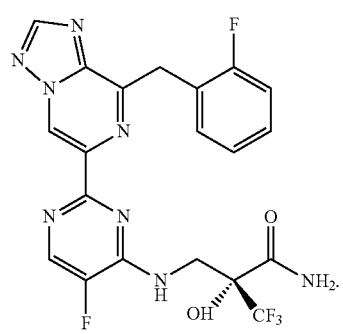

13. A pharmaceutical composition comprising a compound according to claim 1 and at least one pharmaceutically acceptable excipient or carrier.

14. A method of treating a disease in a subject in need thereof that would benefit from sGC stimulation or from an increase in the concentration of nitric oxide (NO) and/or cyclic guanosine monophosphate (cGMP), the method comprising administering a therapeutically effective amount of a compound of claim 1 to the subject in need of treatment.

15. The method according to claim 14, further comprising administering to the subject an effective amount of a suitable therapeutic agent.

16. A compound selected from:

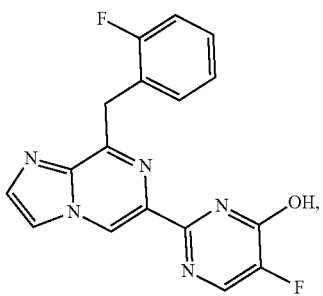

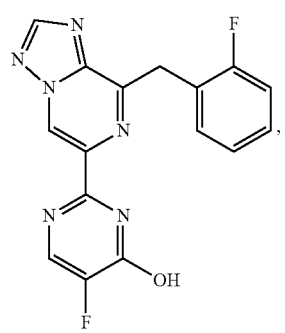

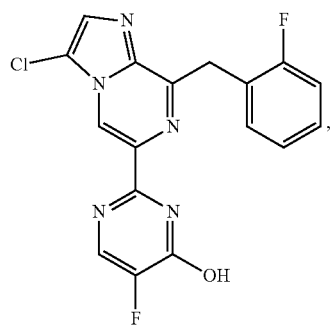
Int-2a
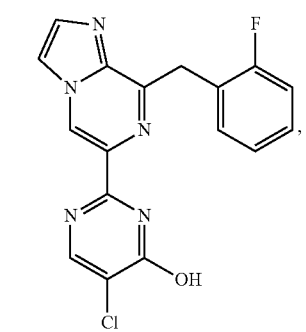
Int-12
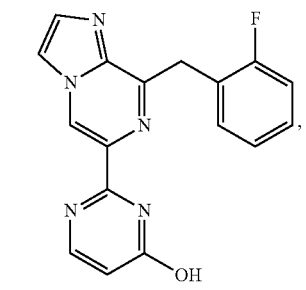
Int-14
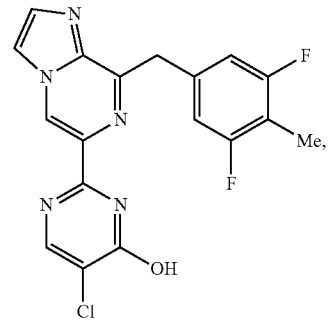
Int-18
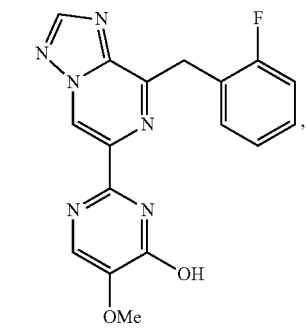
Int-20
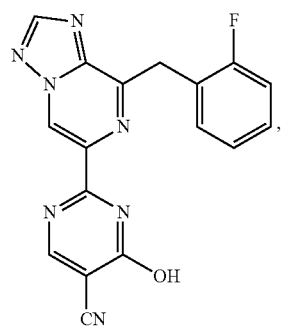
Int-22a
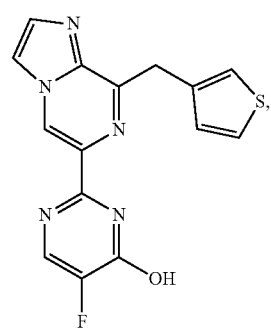
Int-25
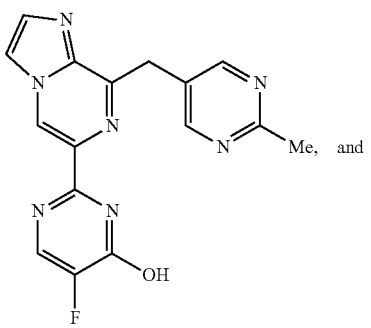
, and
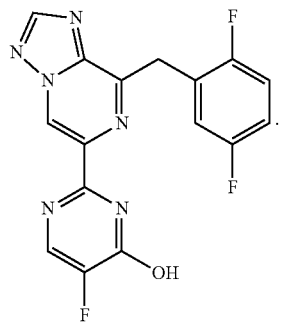
.

17. A compound represented by the following formula:

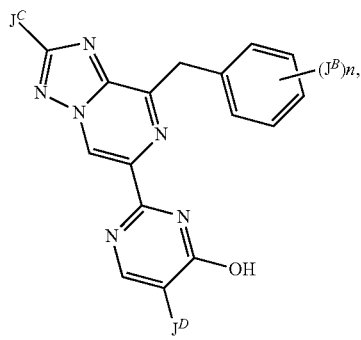

wherein:
n is an integer selected from 0 to 3; and each $J^B$ is independently halogen, —CN, a $C_{1-6}$ aliphatic or —$OR^B$;
wherein each $J^B$ that is a $C_{1-6}$ aliphatic is optionally and independently substituted with up to 3 instances of $R^3$;
each $R^B$ is independently hydrogen or a $C_{1-6}$ aliphatic; said $C_{1-6}$ aliphatic represented by $R^B$ is optionally and independently substituted with up to 3 instances of $R^{3a}$;
each $R^3$ and $R^{3a}$ is, in each instance, independently halogen, —CN, $C_{1-4}$ alkyl, $C_{1-4}$ haloalkyl, —O($C_{1-4}$ alkyl) or —O($C_{1-4}$ haloalkyl);
$J^C$ is independently hydrogen, halogen, $C_{1-4}$ aliphatic, $C_{1-4}$ alkoxy or —CN; wherein each said $C_{1-4}$ aliphatic and each said $C_{1-4}$ alkoxy is optionally and independently substituted by up to 3 instances of $C_{1-4}$ alkoxy, $C_{1-4}$ haloalkoxy, —OH or halogen; and
$J^D$ is hydrogen, halogen, methoxy or —CN.

18. The compound of claim 17, wherein (i) $J^D$ is hydrogen, chloro, fluoro, methoxy or —CN; or (ii) $J^D$ is fluoro.

19. The compound of claim 17, wherein (i) $J^C$ is hydrogen, $C_{1-2}$ alkyl, $C_{1-2}$ alkoxy, $C_{1-2}$ fluoroalkyl, $C_{1-2}$ fluoroalkoxy, halogen or —CN, wherein each said $C_{1-2}$ alkyl and $C_{1-2}$ alkoxy is optionally and independently substituted by up to 3 instances of $C_{1-4}$ alkoxy, $C_{1-4}$ haloalkoxy, —OH or halogen; (ii) $J^C$ is hydrogen or halogen; or (iii) $J^C$ is hydrogen.

20. The compound of claim 17, wherein (i) n is 1, 2 or 3, and each $J^B$ is independently halogen or $C_{1-6}$ aliphatic; (ii) n is 1 or 2 and each $J^B$ is independently halogen or $C_{1-6}$ aliphatic; (iii) n is 1 or 2 and each $J^B$ is fluoro; or (iv) n is 1 and $J^B$ is fluoro.

21. The compound of claim 10 selected from:

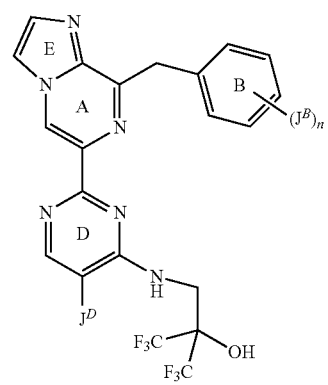

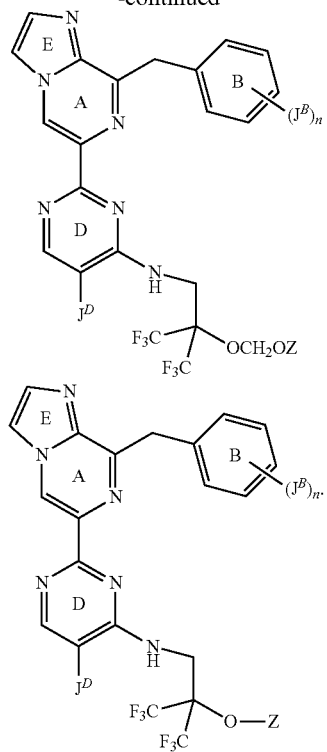

22. The compound of claim 21 represented by formula:

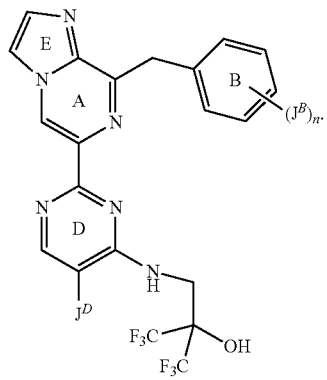

23. The compound of claim 12 represented by:

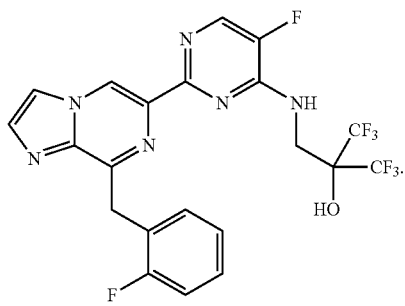

I-2

24. The compound of claim 12 represented by
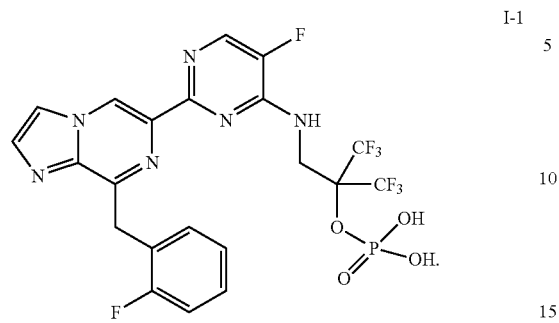
I-1

UNITED STATES PATENT AND TRADEMARK OFFICE
CERTIFICATE OF CORRECTION

PATENT NO. : 11,897,887 B2
APPLICATION NO. : 16/955494
DATED : February 13, 2024
INVENTOR(S) : Glen Robert Rennie et al.

Page 1 of 1

It is certified that error appears in the above-identified patent and that said Letters Patent is hereby corrected as shown below:

In the Claims

In Claim 4, Column 81, Line 66, please replace the term "Formula WB" with the term
-- Formula IVB --.

Signed and Sealed this
Twenty-third Day of April, 2024

Katherine Kelly Vidal
*Director of the United States Patent and Trademark Office*